United States Patent
Gellman et al.

(10) Patent No.: US 8,162,816 B2
(45) Date of Patent: *Apr. 24, 2012

(54) SYSTEM FOR IMPLANTING AN IMPLANT AND METHOD THEREOF

(75) Inventors: Barry N. Gellman, N. Easton, MA (US); Jianmin Li, Lexington, MA (US); Armand Morin, Berkley, MA (US); Jozef Slanda, Milford, MA (US); Richard C. Tah, Framingham, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 479 days.

This patent is subject to a terminal disclaimer.

(21) Appl. No.: 10/093,398

(22) Filed: Mar. 7, 2002

(65) Prior Publication Data

US 2002/0151909 A1    Oct. 17, 2002

Related U.S. Application Data

(60) Provisional application No. 60/274,843, filed on Mar. 9, 2001, provisional application No. 60/286,863, filed on Apr. 26, 2001.

(51) Int. Cl.
*A61F 2/00* (2006.01)
(52) U.S. Cl. ............ 600/37; 606/151; 606/193
(58) Field of Classification Search ........ 600/37, 600/29, 30; 606/205–208, 151, 191, 193
See application file for complete search history.

(56) References Cited

U.S. PATENT DOCUMENTS

| 246,648 A | 9/1881 | Wilcox |
|---|---|---|
| 1,030,530 A | 6/1912 | Palmer |
| 1,066,025 A | 7/1913 | Lieberknecht |
| 1,179,910 A | 4/1916 | Greenfield |
| 1,310,982 A | 7/1919 | Davis |
| 1,417,669 A | 5/1922 | Langworthy |
| 1,517,787 A | 12/1924 | Langbein |
| 1,612,697 A | 12/1926 | Cecil |
| 1,677,671 A | 7/1928 | Councill |
| 2,113,246 A | 4/1938 | Wappler |
| 2,199,025 A | 4/1940 | Conn |

(Continued)

FOREIGN PATENT DOCUMENTS

CA    2198778    3/1996

(Continued)

OTHER PUBLICATIONS

Adamiak et al., "The Efficacy and Safety of the Tension-Free Vaginal Tape Procedure Do Not Depend on the Method of Analgesia", European Urology, 2002, vol. 42, pp. 29-33.

(Continued)

*Primary Examiner* — Darwin Erezo
(74) *Attorney, Agent, or Firm* — Bingham McCutchen LLP

(57) ABSTRACT

A system for implanting an implant and method thereof is disclosed. In general overview, the system includes an implant, an envelope enclosing the implant, a delivery assembly and an attachment piece for attaching the envelope or implant to the delivery assembly. The envelope may include a drug coating, positioning aids, and means to ease envelope removal. In one embodiment, the delivery assembly is employed for implant and/or envelope delivery inside the patient's body. In another embodiment, the delivery assembly and an attachment piece are employed to deliver the implant or the envelope inside the patient's body.

16 Claims, 49 Drawing Sheets

U.S. PATENT DOCUMENTS

| | | | |
|---|---|---|---|
| 2,200,120 A | 5/1940 | Nauth | |
| 2,454,680 A | 11/1948 | Stephens | |
| 2,487,502 A | 11/1949 | Willinsky | |
| 2,556,783 A | 6/1951 | Wallace | |
| 2,635,238 A | 4/1953 | Garland | |
| 2,655,921 A | 10/1953 | Haboush | |
| 2,666,430 A | 1/1954 | Gispert | |
| 2,671,444 A | 3/1954 | Pease, Jr. | |
| 2,738,790 A | 3/1956 | Todt, Sr. et al. | |
| 2,751,903 A | 6/1956 | Ivory et al. | |
| 2,917,878 A | 12/1959 | Edwin et al. | |
| 2,973,859 A | 3/1961 | Schladermundt | |
| 3,003,155 A | 10/1961 | Mielzynski et al. | |
| 3,054,406 A | 9/1962 | Usher | |
| 3,124,136 A | 3/1964 | Usher | |
| 3,181,533 A | 5/1965 | Heath | |
| 3,212,502 A | 10/1965 | Myers | |
| 3,314,431 A | 4/1967 | Smith, Jr. | |
| 3,364,200 A | 1/1968 | Ashton et al. | |
| 3,388,847 A | 6/1968 | Kasulin et al. | |
| 3,551,987 A | 1/1971 | Wilkinson | |
| 3,580,313 A | 5/1971 | McKnight | |
| 3,593,903 A | 7/1971 | Astafiev et al. | |
| 3,596,656 A | 8/1971 | Kaute | |
| 3,620,212 A | 11/1971 | Fannon, Jr. et al. | 128/130 |
| 3,666,750 A | 5/1972 | Briskin et al. | |
| 3,699,969 A | 10/1972 | Allen | |
| 3,705,575 A | 12/1972 | Edwards | |
| 3,710,592 A | 1/1973 | Scow | |
| 3,710,795 A | 1/1973 | Higuchi et al. | |
| 3,739,784 A | 6/1973 | Itoh | 128/320 |
| 3,744,495 A | 7/1973 | Johnson | |
| 3,823,705 A | 7/1974 | Trimble | |
| 3,857,396 A | 12/1974 | Hardwick | |
| 3,866,611 A * | 2/1975 | Baumrucker | 128/885 |
| 3,875,937 A | 4/1975 | Schmitt et al. | |
| 3,877,434 A | 4/1975 | Ferguson et al. | |
| 3,890,977 A | 6/1975 | Wilson | 128/418 |
| 3,892,232 A | 7/1975 | Neufeld | |
| 3,918,455 A | 11/1975 | Coplan | |
| 3,937,223 A | 2/1976 | Roth | |
| 3,995,619 A | 12/1976 | Glatzer | |
| 4,006,747 A | 2/1977 | Kronenthal et al. | |
| 4,065,816 A | 1/1978 | Sawyer | |
| 4,085,756 A | 4/1978 | Weaver | |
| 4,159,716 A | 7/1979 | Borchers | |
| 4,172,458 A | 10/1979 | Pereyra | |
| 4,175,557 A | 11/1979 | Hung | |
| 4,193,137 A | 3/1980 | Heck | |
| 4,217,890 A | 8/1980 | Owens | 128/1 R |
| 4,347,847 A | 9/1982 | Usher | |
| 4,363,319 A | 12/1982 | Altshuler | |
| 4,367,816 A | 1/1983 | Wilkes | |
| 4,371,124 A | 2/1983 | Gifford et al. | |
| 4,391,869 A | 7/1983 | Cook et al. | |
| 4,392,495 A | 7/1983 | Bayers | |
| 4,400,833 A | 8/1983 | Kurland | |
| 4,409,974 A | 10/1983 | Freedland | |
| 4,414,967 A | 11/1983 | Shapiro | |
| 4,415,111 A | 11/1983 | McHarrie et al. | |
| 4,421,112 A | 12/1983 | Mains et al. | |
| 4,422,567 A | 12/1983 | Haynes | |
| 4,438,769 A | 3/1984 | Pratt et al. | |
| 4,445,898 A | 5/1984 | Jensen | |
| 4,452,245 A | 6/1984 | Usher | |
| 4,520,821 A | 6/1985 | Schmidt et al. | |
| 4,527,726 A | 7/1985 | Assell et al. | |
| 4,535,768 A | 8/1985 | Hourahane et al. | |
| 4,537,185 A | 8/1985 | Stednitz | |
| 4,545,374 A | 10/1985 | Jacobson | |
| 4,549,545 A | 10/1985 | Levy | |
| 4,569,469 A | 2/1986 | Mongeon et al. | |
| 4,576,167 A | 3/1986 | Noiles | |
| 4,592,339 A | 6/1986 | Kuzmak et al. | |
| 4,606,335 A | 8/1986 | Wedeen | |
| 4,606,343 A | 8/1986 | Conta et al. | |
| 4,614,187 A | 9/1986 | Mulhollan et al. | 128/303 R |
| 4,625,726 A | 12/1986 | Duthoy | 128/328 |
| 4,632,100 A | 12/1986 | Somers et al. | |
| 4,633,871 A | 1/1987 | Shinozuka | 128/321 |
| 4,633,873 A | 1/1987 | Dumican et al. | |
| 4,635,634 A | 1/1987 | Santos | |
| 4,652,264 A | 3/1987 | Dumican | |
| 4,655,219 A | 4/1987 | Petruzzi | 128/321 |
| 4,655,221 A | 4/1987 | Devereux | |
| 4,664,305 A | 5/1987 | Blake, III et al. | |
| 4,665,906 A | 5/1987 | Jervis | 128/92 YN |
| 4,669,473 A | 6/1987 | Richards et al. | |
| 4,688,555 A | 8/1987 | Wardle | 128/4 |
| 4,691,705 A | 9/1987 | Okada | 128/328 |
| 4,694,781 A | 9/1987 | Howe et al. | |
| 4,705,040 A | 11/1987 | Mueller et al. | |
| 4,738,255 A | 4/1988 | Goble et al. | |
| 4,739,751 A | 4/1988 | Sapega et al. | |
| 4,741,330 A | 5/1988 | Hayhurst | |
| 4,741,335 A | 5/1988 | Okada | 128/320 |
| 4,744,353 A | 5/1988 | McFarland | |
| 4,750,492 A | 6/1988 | Jacobs | |
| 4,763,669 A | 8/1988 | Jaeger | 128/751 |
| 4,768,505 A | 9/1988 | Okada et al. | 128/328 |
| 4,769,038 A | 9/1988 | Bendavid et al. | |
| 4,776,337 A | 10/1988 | Palmaz | |
| 4,784,126 A | 11/1988 | Hourahane | |
| 4,784,137 A | 11/1988 | Kulik et al. | |
| 4,784,138 A | 11/1988 | Sinnett | |
| 4,838,884 A | 6/1989 | Dumican et al. | |
| 4,854,316 A | 8/1989 | Davis | |
| 4,857,041 A | 8/1989 | Annis et al. | |
| 4,870,957 A | 10/1989 | Goble et al. | |
| 4,872,451 A | 10/1989 | Moore et al. | |
| 4,873,977 A | 10/1989 | Avant et al. | |
| 4,880,015 A | 11/1989 | Nierman | 128/751 |
| 4,883,048 A | 11/1989 | Purnell et al. | |
| 4,889,119 A | 12/1989 | Jamiolkowski et al. | |
| 4,898,156 A | 2/1990 | Gatturna et al. | |
| 4,899,743 A | 2/1990 | Nicholson et al. | |
| 4,905,692 A | 3/1990 | More | |
| 4,909,789 A | 3/1990 | Taguchi et al. | 604/107 |
| 4,911,165 A | 3/1990 | Lennard et al. | |
| 4,920,958 A | 5/1990 | Walt et al. | |
| 4,920,986 A | 5/1990 | Biswas | |
| 4,926,722 A | 5/1990 | Sorensen et al. | |
| 4,938,760 A | 7/1990 | Burton et al. | |
| 4,940,467 A | 7/1990 | Tronzo | |
| 4,944,741 A | 7/1990 | Hasson | 606/206 |
| 4,945,920 A | 8/1990 | Clossick | 128/751 |
| 4,946,468 A | 8/1990 | Li | |
| 4,957,498 A | 9/1990 | Caspari et al. | |
| 4,960,420 A | 10/1990 | Goble et al. | |
| 4,968,315 A | 11/1990 | Gatturna | |
| 4,969,892 A | 11/1990 | Burton et al. | |
| 4,973,300 A | 11/1990 | Wright | |
| 4,978,351 A | 12/1990 | Rozas | |
| 4,986,831 A | 1/1991 | King et al. | |
| 4,988,339 A | 1/1991 | Vadher | |
| 4,997,433 A | 3/1991 | Goble et al. | |
| 4,997,434 A | 3/1991 | Seedhom et al. | |
| 4,997,436 A | 3/1991 | Oberlander | |
| 5,002,550 A | 3/1991 | Li | |
| 5,002,551 A | 3/1991 | Linsky et al. | |
| 5,007,894 A | 4/1991 | Enhorning | |
| 5,012,822 A | 5/1991 | Schwarz | |
| 5,013,292 A | 5/1991 | Lemay | |
| 5,013,316 A | 5/1991 | Goble et al. | |
| 5,019,032 A | 5/1991 | Robertson | |
| 5,026,398 A | 6/1991 | May et al. | |
| 5,030,219 A | 7/1991 | Matsen, III et al. | |
| 5,036,867 A | 8/1991 | Biswas | |
| 5,040,715 A | 8/1991 | Green et al. | |
| 5,046,513 A | 9/1991 | Gatturna et al. | |
| 5,052,607 A | 10/1991 | Dutton | |
| 5,057,112 A | 10/1991 | Sherman et al. | |
| 5,057,114 A | 10/1991 | Wittich et al. | 606/127 |
| 5,059,199 A | 10/1991 | Okada et al. | 606/127 |
| 5,061,181 A | 10/1991 | Niznick | |
| 5,064,434 A | 11/1991 | Haber | |
| 5,078,730 A | 1/1992 | Li et al. | |

| Patent | Date | Name | Ref |
|---|---|---|---|
| 5,078,731 A | 1/1992 | Hayhurst | |
| 5,080,674 A | 1/1992 | Jacobs et al. | 623/20 |
| 5,084,058 A | 1/1992 | Li | |
| 5,085,661 A | 2/1992 | Moss | |
| 5,087,263 A | 2/1992 | Li | |
| 5,088,323 A | 2/1992 | Johnson et al. | |
| 5,089,013 A | 2/1992 | Bezwada et al. | |
| 5,098,440 A | 3/1992 | Hillstead | 606/108 |
| 5,100,417 A | 3/1992 | Cerier et al. | |
| 5,102,421 A | 4/1992 | Anspach, Jr. | |
| 5,108,397 A | 4/1992 | White | |
| 5,112,337 A | 5/1992 | Paulos et al. | |
| 5,112,344 A | 5/1992 | Petros | 606/148 |
| 5,116,338 A | 5/1992 | Poggie et al. | |
| 5,122,155 A | 6/1992 | Eberbach | |
| 5,123,924 A | 6/1992 | Sioshansi et al. | 623/16 |
| 5,129,902 A | 7/1992 | Goble et al. | |
| 5,133,723 A | 7/1992 | Li et al. | |
| 5,141,520 A | 8/1992 | Goble et al. | |
| 5,147,374 A | 9/1992 | Fernandez | |
| 5,149,329 A | 9/1992 | Richardson | |
| 5,152,279 A | 10/1992 | Wilk | 128/17 |
| 5,152,749 A | 10/1992 | Giesy et al. | |
| 5,152,790 A | 10/1992 | Rosenberg et al. | |
| 5,156,315 A | 10/1992 | Green et al. | |
| 5,163,942 A | 11/1992 | Rydell | 606/113 |
| 5,163,946 A | 11/1992 | Li | |
| 5,174,300 A | 12/1992 | Bales et al. | 128/751 |
| 5,176,692 A | 1/1993 | Wilk et al. | |
| 5,178,630 A | 1/1993 | Schmitt | |
| 5,180,388 A | 1/1993 | DiCarlo | |
| 5,188,636 A | 2/1993 | Fedotov | |
| 5,192,008 A | 3/1993 | Hwan | 222/391 |
| 5,192,303 A | 3/1993 | Gatturna et al. | |
| 5,195,542 A | 3/1993 | Gazielly et al. | |
| 5,197,968 A | 3/1993 | Clement | 606/115 |
| 5,203,784 A | 4/1993 | Ross et al. | |
| 5,203,787 A | 4/1993 | Noblitt et al. | |
| 5,207,679 A | 5/1993 | Li | |
| 5,209,747 A | 5/1993 | Knoepfler | 606/16 |
| 5,217,462 A | 6/1993 | Asnis et al. | |
| 5,217,486 A | 6/1993 | Rice et al. | |
| 5,222,508 A | 6/1993 | Contarini | |
| 5,224,946 A | 7/1993 | Hayhurst et al. | |
| 5,236,445 A | 8/1993 | Hayhurst et al. | |
| 5,242,457 A | 9/1993 | Akopov et al. | |
| 5,250,033 A | 10/1993 | Evans et al. | |
| 5,251,638 A | 10/1993 | Cottone, Jr. et al. | 128/751 |
| 5,254,130 A | 10/1993 | Poncet et al. | 606/206 |
| 5,254,133 A | 10/1993 | Seid | 606/215 |
| 5,256,133 A | 10/1993 | Spitz | |
| 5,256,150 A | 10/1993 | Quiachon et al. | |
| 5,257,692 A | 11/1993 | Heacox | |
| 5,258,000 A | 11/1993 | Gianturco | |
| 5,258,016 A | 11/1993 | DiPoto et al. | |
| 5,263,969 A | 11/1993 | Phillips | |
| 5,268,001 A | 12/1993 | Nicholson et al. | |
| 5,279,311 A | 1/1994 | Snyder | |
| 5,281,237 A | 1/1994 | Gimpelson | |
| 5,282,812 A | 2/1994 | Suarez, Jr. | |
| 5,289,963 A | 3/1994 | McGarry et al. | |
| 5,290,217 A | 3/1994 | Campos | |
| 5,290,294 A | 3/1994 | Cox et al. | 606/108 |
| 5,292,328 A | 3/1994 | Hain et al. | |
| 5,304,220 A | 4/1994 | Maginot | |
| 5,311,858 A | 5/1994 | Adair | 128/4 |
| 5,312,433 A | 5/1994 | Boebel et al. | 606/205 |
| 5,316,543 A | 5/1994 | Eberbach | |
| 5,328,077 A | 7/1994 | Lou | |
| 5,333,624 A | 8/1994 | Tovey | 128/897 |
| 5,334,208 A | 8/1994 | Soehendra et al. | 222/391 |
| 5,337,736 A | 8/1994 | Reddy | |
| 5,339,799 A * | 8/1994 | Kami et al. | 600/117 |
| 5,354,292 A | 10/1994 | Braeuer et al. | |
| 5,356,064 A | 10/1994 | Green et al. | |
| 5,362,294 A | 11/1994 | Seitzinger | |
| 5,364,002 A | 11/1994 | Green et al. | |
| 5,364,406 A | 11/1994 | Sewell, Jr. | |
| 5,366,460 A | 11/1994 | Eberbach | |
| 5,366,479 A | 11/1994 | McGarry et al. | |
| 5,368,595 A | 11/1994 | Lewis | |
| 5,368,602 A | 11/1994 | de la Torre | |
| 5,370,282 A | 12/1994 | Sedlmeier | 222/391 |
| 5,370,650 A | 12/1994 | Tovey et al. | |
| 5,370,662 A | 12/1994 | Stone et al. | |
| 5,372,146 A | 12/1994 | Branch | |
| 5,376,094 A | 12/1994 | Kline | 606/113 |
| 5,379,933 A | 1/1995 | Green et al. | |
| 5,381,943 A | 1/1995 | Allen et al. | |
| 5,383,477 A | 1/1995 | DeMatteis | |
| 5,383,928 A | 1/1995 | Scott et al. | 623/1 |
| 5,397,332 A | 3/1995 | Kammerer et al. | |
| 5,411,506 A | 5/1995 | Goble et al. | |
| 5,417,203 A | 5/1995 | Tovey et al. | 128/4 |
| 5,417,712 A | 5/1995 | Whittaker et al. | |
| 5,423,860 A | 6/1995 | Lizardi et al. | |
| 5,425,489 A | 6/1995 | Shichman et al. | |
| 5,425,737 A | 6/1995 | Burbank et al. | |
| 5,425,743 A | 6/1995 | Nicholas | 606/208 |
| 5,425,984 A | 6/1995 | Kennedy et al. | |
| 5,431,173 A | 7/1995 | Chin et al. | |
| 5,437,603 A | 8/1995 | Cerny et al. | |
| 5,441,502 A | 8/1995 | Bartlett | |
| 5,441,508 A | 8/1995 | Gazielly et al. | |
| 5,443,482 A | 8/1995 | Stone et al. | |
| 5,451,235 A | 9/1995 | Lock et al. | |
| 5,456,722 A | 10/1995 | McLeod et al. | |
| 5,474,543 A | 12/1995 | McKay | |
| 5,499,991 A | 3/1996 | Garman et al. | |
| 5,500,001 A | 3/1996 | Trott | |
| 5,501,683 A | 3/1996 | Trott | |
| 5,501,690 A | 3/1996 | Measamer et al. | |
| 5,507,754 A | 4/1996 | Green et al. | |
| 5,507,796 A | 4/1996 | Hasson | |
| 5,520,696 A | 5/1996 | Wenstrom, Jr. | |
| 5,520,700 A | 5/1996 | Beyar et al. | |
| 5,522,843 A | 6/1996 | Zang | |
| 5,522,845 A | 6/1996 | Wenstrom, Jr. | |
| 5,527,341 A | 6/1996 | Gogolewski et al. | |
| 5,538,427 A | 7/1996 | Hoffman et al. | |
| 5,540,703 A | 7/1996 | Barker et al. | |
| 5,544,664 A | 8/1996 | Benderev et al. | |
| 5,549,617 A | 8/1996 | Green et al. | |
| 5,549,619 A | 8/1996 | Peters et al. | |
| 5,562,689 A | 10/1996 | Green et al. | |
| 5,569,273 A | 10/1996 | Titone et al. | |
| 5,571,117 A | 11/1996 | Ahn | |
| 5,573,548 A | 11/1996 | Nazre et al. | |
| 5,578,057 A | 11/1996 | Wenstrom, Jr. | |
| 5,582,188 A | 12/1996 | Benderev et al. | |
| 5,584,695 A | 12/1996 | Lal Sachdeva et al. | |
| 5,584,835 A | 12/1996 | Greenfield | |
| 5,591,163 A | 1/1997 | Thompson | |
| 5,591,207 A | 1/1997 | Coleman | |
| 5,601,575 A | 2/1997 | Measamer et al. | |
| 5,607,432 A | 3/1997 | Fucci | |
| 5,611,515 A | 3/1997 | Benderev et al. | |
| 5,618,314 A | 4/1997 | Harwin et al. | |
| 5,620,012 A | 4/1997 | Benderev et al. | |
| 5,624,446 A | 4/1997 | Harryman, II | |
| 5,634,931 A | 6/1997 | Kugel | |
| 5,634,944 A | 6/1997 | Magram | |
| 5,637,112 A | 6/1997 | Moore et al. | |
| 5,639,274 A | 6/1997 | Fischell et al. | |
| 5,641,502 A | 6/1997 | Skalla et al. | |
| 5,641,566 A | 6/1997 | Kranzler et al. | |
| 5,643,288 A | 7/1997 | Thompson | |
| 5,643,320 A | 7/1997 | Lower et al. | |
| 5,643,596 A | 7/1997 | Pruss et al. | |
| 5,645,589 A | 7/1997 | Li | |
| 5,645,849 A | 7/1997 | Pruss et al. | |
| 5,645,915 A | 7/1997 | Kranzler et al. | |
| 5,647,836 A | 7/1997 | Blake, III et al. | |
| 5,649,940 A | 7/1997 | Hart et al. | |
| 5,653,373 A | 8/1997 | Green et al. | |
| 5,658,296 A | 8/1997 | Bates et al. | 606/127 |
| 5,660,854 A | 8/1997 | Haynes et al. | 424/450 |
| 5,662,654 A | 9/1997 | Thompson | |

| | | | |
|---|---|---|---|
| 5,662,658 A | 9/1997 | Wenstrom, Jr. | |
| 5,674,247 A | 10/1997 | Sohn | |
| 5,681,301 A | 10/1997 | Yang et al. | |
| 5,681,310 A | 10/1997 | Yuan et al. | |
| 5,681,352 A | 10/1997 | Clancy, III et al. | |
| 5,683,378 A | 11/1997 | Christy | 606/1 |
| 5,683,418 A | 11/1997 | Luscombe et al. | |
| 5,690,649 A | 11/1997 | Li | |
| 5,690,655 A | 11/1997 | Hart et al. | 606/148 |
| 5,690,677 A | 11/1997 | Schmieding et al. | |
| 5,697,931 A | 12/1997 | Thompson | |
| 5,700,266 A | 12/1997 | Harryman, II | |
| 5,700,286 A | 12/1997 | Tartaglia et al. | |
| 5,702,215 A | 12/1997 | Li | |
| 5,702,397 A | 12/1997 | Goble et al. | |
| 5,702,415 A | 12/1997 | Matthai et al. | |
| 5,707,647 A | 1/1998 | Dunn et al. | |
| 5,725,529 A | 3/1998 | Nicholson et al. | |
| 5,725,557 A | 3/1998 | Gatturna et al. | |
| 5,728,100 A | 3/1998 | Skiba | |
| 5,733,337 A | 3/1998 | Carr, Jr. et al. | |
| 5,742,943 A | 4/1998 | Chen | |
| 5,752,963 A | 5/1998 | Allard et al. | |
| 5,766,221 A | 6/1998 | Benderev et al. | |
| 5,769,864 A | 6/1998 | Kugel | |
| 5,776,184 A | 7/1998 | Tuch | |
| 5,782,834 A | 7/1998 | Lucey et al. | 606/22 |
| 5,782,862 A | 7/1998 | Bonutti | |
| 5,785,640 A | 7/1998 | Kresch et al. | 600/29 |
| 5,788,710 A | 8/1998 | Bates et al. | 606/127 |
| 5,807,403 A | 9/1998 | Beyar et al. | |
| 5,813,975 A | 9/1998 | Valenti | |
| 5,814,051 A | 9/1998 | Wenstrom, Jr. | |
| 5,814,071 A | 9/1998 | McDevitt et al. | |
| 5,814,072 A | 9/1998 | Bonutti | |
| 5,816,258 A | 10/1998 | Jervis | |
| 5,824,049 A | 10/1998 | Ragheb et al. | |
| 5,824,082 A | 10/1998 | Brown | |
| 5,827,291 A | 10/1998 | Fucci et al. | |
| 5,836,314 A | 11/1998 | Benderev et al. | |
| 5,836,315 A | 11/1998 | Benderev et al. | |
| 5,836,961 A | 11/1998 | Kieturakis | |
| 5,840,011 A | 11/1998 | Landgrebe et al. | 600/30 |
| 5,842,478 A | 12/1998 | Benderev et al. | |
| 5,849,004 A | 12/1998 | Bramlet | |
| 5,851,210 A | 12/1998 | Torossian | |
| 5,851,219 A | 12/1998 | Goble et al. | |
| 5,860,993 A | 1/1999 | Thompson et al. | |
| 5,868,747 A | 2/1999 | Ochoa et al. | |
| 5,868,789 A | 2/1999 | Huebner | |
| 5,871,503 A | 2/1999 | Bartlett | |
| 5,899,909 A * | 5/1999 | Claren et al. | 606/119 |
| 5,916,225 A | 6/1999 | Kugel | |
| 5,922,026 A | 7/1999 | Chin | |
| 5,934,283 A | 8/1999 | Willem et al. | |
| 5,935,122 A | 8/1999 | Fourkas et al. | |
| 5,935,138 A | 8/1999 | McJames, II et al. | |
| 5,954,057 A | 9/1999 | Li | |
| 5,957,932 A | 9/1999 | Bates et al. | 606/127 |
| 5,972,000 A | 10/1999 | Beyar et al. | |
| 5,989,180 A | 11/1999 | Norton | |
| 5,997,554 A | 12/1999 | Thompson | |
| 6,010,447 A | 1/2000 | Kardjian | 600/29 |
| 6,030,337 A | 2/2000 | Grant et al. | |
| 6,030,393 A | 2/2000 | Corlew | |
| 6,039,686 A | 3/2000 | Kovac | 600/30 |
| 6,042,534 A | 3/2000 | Gellman et al. | |
| 6,042,536 A | 3/2000 | Tihon et al. | |
| 6,042,583 A | 3/2000 | Thompson et al. | |
| 6,050,937 A | 4/2000 | Benderev | 600/37 |
| 6,053,935 A | 4/2000 | Brenneman et al. | |
| 6,056,687 A | 5/2000 | Polyak et al. | |
| 6,059,801 A | 5/2000 | Samimi | |
| 6,068,591 A | 5/2000 | Bruckner et al. | |
| 6,077,216 A | 6/2000 | Benderev et al. | 600/29 |
| 6,090,116 A | 7/2000 | D'Aversa et al. | |
| 6,095,969 A | 8/2000 | Karram et al. | |
| 6,099,538 A | 8/2000 | Moses et al. | |
| 6,099,547 A | 8/2000 | Gellman et al. | |
| 6,102,921 A | 8/2000 | Zhu et al. | |
| 6,110,101 A | 8/2000 | Tihon et al. | |
| 6,113,611 A | 9/2000 | Allen et al. | |
| 6,117,067 A | 9/2000 | Gil-Vernet | 600/30 |
| 6,135,945 A | 10/2000 | Sultan | |
| 6,168,801 B1 | 1/2001 | Heil, Jr. et al. | 424/426 |
| 6,200,261 B1 | 3/2001 | Deininger et al. | |
| 6,200,330 B1 | 3/2001 | Benderev et al. | 606/232 |
| 6,221,005 B1 | 4/2001 | Bruckner et al. | |
| 6,224,616 B1 | 5/2001 | Kugel | 606/151 |
| 6,231,581 B1 | 5/2001 | Shank et al. | 606/157 |
| 6,245,082 B1 | 6/2001 | Gellman et al. | |
| 6,264,676 B1 | 7/2001 | Gellman et al. | |
| 6,273,852 B1 * | 8/2001 | Lehe et al. | 600/30 |
| 6,299,607 B1 | 10/2001 | Osborn, III et al. | |
| 6,306,079 B1 | 10/2001 | Trabucco | |
| 6,312,448 B1 | 11/2001 | Bonutti | |
| 6,319,262 B1 | 11/2001 | Bates et al. | 606/127 |
| 6,319,272 B1 | 11/2001 | Brenneman et al. | |
| 6,322,492 B1 | 11/2001 | Kovac | |
| 6,328,686 B1 | 12/2001 | Kovac | |
| 6,328,758 B1 | 12/2001 | Tornier et al. | |
| 6,334,446 B1 | 1/2002 | Beyar | |
| 6,355,065 B1 | 3/2002 | Gabbay | |
| 6,382,214 B1 | 5/2002 | Raz et al. | |
| 6,387,040 B1 | 5/2002 | Grant et al. | |
| 6,387,041 B1 | 5/2002 | Harari et al. | |
| 6,391,060 B1 | 5/2002 | Ory et al. | |
| 6,402,767 B1 | 6/2002 | Nash et al. | |
| 6,406,234 B2 | 6/2002 | Frigg | |
| 6,406,423 B1 | 6/2002 | Scetbon | |
| 6,406,480 B1 | 6/2002 | Beyar et al. | |
| 6,416,462 B1 | 7/2002 | Tovey et al. | |
| 6,423,080 B1 | 7/2002 | Gellman et al. | |
| 6,428,562 B2 | 8/2002 | Bonutti | |
| 6,443,886 B2 | 9/2002 | Deininger et al. | |
| 6,447,524 B1 | 9/2002 | Knodel et al. | |
| 6,451,032 B1 | 9/2002 | Ory et al. | |
| 6,461,291 B1 | 10/2002 | Polyak et al. | |
| 6,475,139 B1 | 11/2002 | Miller | |
| 6,478,727 B2 * | 11/2002 | Scetbon | 600/30 |
| 6,478,763 B1 | 11/2002 | Simonsen et al. | |
| 6,491,703 B1 | 12/2002 | Ulmsten | |
| 6,494,879 B2 | 12/2002 | Lennox et al. | |
| 6,517,566 B1 | 2/2003 | Hovland et al. | |
| 6,530,879 B1 | 3/2003 | Adamkiewicz | |
| 6,582,442 B2 | 6/2003 | Simon et al. | |
| 6,589,277 B1 | 7/2003 | Fabiani et al. | |
| 6,595,911 B2 | 7/2003 | LoVuolo | |
| 6,596,002 B2 | 7/2003 | Therin et al. | |
| 6,612,977 B2 | 9/2003 | Staskin et al. | |
| 6,638,210 B2 | 10/2003 | Berger | |
| 6,638,211 B2 | 10/2003 | Suslian et al. | |
| 6,641,525 B2 | 11/2003 | Rocheleau et al. | |
| 6,648,921 B2 | 11/2003 | Anderson et al. | |
| 6,652,450 B2 | 11/2003 | Neisz et al. | |
| 6,685,629 B2 * | 2/2004 | Therin | 600/37 |
| 6,692,491 B1 | 2/2004 | Phan | |
| 6,702,827 B1 | 3/2004 | Lund et al. | |
| 6,755,781 B2 | 6/2004 | Gellman | |
| 6,802,807 B2 | 10/2004 | Anderson et al. | |
| 6,830,052 B2 | 12/2004 | Carter et al. | |
| 6,908,425 B2 | 6/2005 | Luscombe | |
| 6,991,597 B2 * | 1/2006 | Gellman et al. | 600/37 |
| 7,351,196 B2 | 4/2008 | Goldmann et al. | |
| 2001/0018549 A1 | 8/2001 | Scetbon | |
| 2001/0049467 A1 | 12/2001 | Lehe et al. | |
| 2002/0022841 A1 | 2/2002 | Kovac | |
| 2002/0028980 A1 | 3/2002 | Thierfelder et al. | |
| 2002/0052654 A1 | 5/2002 | Darois et al. | |
| 2002/0055748 A1 | 5/2002 | Gellman et al. | |
| 2002/0068948 A1 | 6/2002 | Stormby et al. | |
| 2002/0072694 A1 | 6/2002 | Snitkin et al. | |
| 2002/0077526 A1 | 6/2002 | Kammerer et al. | |
| 2002/0091298 A1 | 7/2002 | Landgrebe | |
| 2002/0091373 A1 | 7/2002 | Berger | |
| 2002/0099258 A1 | 7/2002 | Staskin et al. | |
| 2002/0099259 A1 | 7/2002 | Anderson et al. | |
| 2002/0107430 A1 | 8/2002 | Neisz et al. | |

| | | | |
|---|---|---|---|
| 2002/0116025 A1 | 8/2002 | Haab | |
| 2002/0128670 A1 | 9/2002 | Ulmsten et al. | |
| 2002/0138025 A1 | 9/2002 | Gellman | |
| 2002/0143234 A1 | 10/2002 | LoVuolo | |
| 2002/0147382 A1 | 10/2002 | Neisz et al. | |
| 2002/0151762 A1 | 10/2002 | Rocheleau et al. | |
| 2002/0151910 A1 | 10/2002 | Gellman et al. | |
| 2002/0156487 A1 | 10/2002 | Gellman et al. | |
| 2002/0161382 A1 | 10/2002 | Neisz et al. | |
| 2002/0165566 A1 | 11/2002 | Ulmsten | |
| 2002/0188169 A1 | 12/2002 | Kammerer et al. | |
| 2003/0004395 A1 | 1/2003 | Therin | |
| 2003/0004580 A1 | 1/2003 | Sump et al. | |
| 2003/0009181 A1 | 1/2003 | Gellman et al. | |
| 2003/0010929 A1 | 1/2003 | Priewe et al. | |
| 2003/0023135 A1 | 1/2003 | Ulmsten et al. | |
| 2003/0023136 A1 | 1/2003 | Raz et al. | |
| 2003/0023137 A1 | 1/2003 | Gellman | |
| 2003/0023138 A1 | 1/2003 | Luscombe | |
| 2003/0028075 A1 | 2/2003 | Ulmsten et al. | |
| 2003/0045774 A1 | 3/2003 | Staskin et al. | |
| 2003/0050530 A1 | 3/2003 | Neisz et al. | |
| 2003/0062052 A1 | 4/2003 | Carter et al. | |
| 2003/0065402 A1 | 4/2003 | Anderson et al. | |
| 2003/0100954 A1 | 5/2003 | Schuldt-Hempe et al. | |
| 2003/0130670 A1 | 7/2003 | Anderson et al. | |
| 2003/0171644 A1 | 9/2003 | Anderson et al. | |
| 2004/0015048 A1 | 1/2004 | Neisz et al. | |

FOREIGN PATENT DOCUMENTS

| | | |
|---|---|---|
| DE | 2 305 815 | 8/1974 |
| DE | 24 28 319 | 1/1976 |
| DE | 25 32 242 | 2/1977 |
| DE | 8203923 | 4/1983 |
| DE | 32 06 846 A1 | 9/1983 |
| DE | 33 40 581 C1 | 6/1985 |
| DE | 35 21 717 A1 | 12/1985 |
| DE | 34 40 889 C1 | 6/1986 |
| DE | 86 04 065 U1 | 7/1986 |
| DE | 36 03 344 A1 | 8/1986 |
| DE | 87 07 515 U1 | 9/1987 |
| DE | 37 09 706 A1 | 10/1987 |
| DE | 87 07 516 U1 | 10/1987 |
| DE | 37 14 560 A1 | 11/1987 |
| DE | 37 04 094 A1 | 8/1988 |
| DE | 37 09 067 A1 | 9/1988 |
| DE | 37 39 254 A1 | 6/1989 |
| DE | 40 24 636 A1 | 2/1992 |
| DE | 41 31 176 A1 | 4/1993 |
| DE | 42 12 430 A1 | 10/1993 |
| DE | 20204669 | 9/2003 |
| EP | 0 140 557 A3 | 5/1985 |
| EP | 0 153 831 A3 | 9/1985 |
| EP | 0 160 870 | 11/1985 |
| EP | 0 241 240 A2 | 10/1987 |
| EP | 0 281 763 A2 | 9/1988 |
| EP | 0 334 046 B1 | 9/1989 |
| EP | 0 337 918 B1 | 10/1989 |
| EP | 0 417 031 A2 | 3/1991 |
| EP | 0 437 063 A2 | 7/1991 |
| EP | 0 437 063 A3 | 7/1991 |
| EP | 0 450 608 A1 | 10/1991 |
| EP | 0 484 671 A2 | 5/1992 |
| EP | 0 538 984 B1 | 4/1993 |
| EP | 0555 103 A1 | 8/1993 |
| EP | 0 558 993 A2 | 9/1993 |
| EP | 0 565 049 A1 | 10/1993 |
| EP | 0 571 057 A1 | 11/1993 |
| EP | 0 598 607 A2 | 5/1994 |
| EP | 0 599 772 A1 | 6/1994 |
| EP | 0 686 373 A1 | 12/1995 |
| EP | 0 854 691 B1 | 7/1998 |
| EP | 0 778 749 B1 | 12/2000 |
| EP | 1 151 722 A2 | 7/2001 |
| EP | 1 159 921 A2 | 12/2001 |
| EP | 1 151 722 A3 | 1/2002 |
| EP | 1191902 B1 | 4/2002 |
| FR | 2 432 861 | 3/1980 |
| FR | 2 718 012 | 10/1995 |
| FR | 2 739 016 | 3/1997 |
| GB | 2 151 142 A | 7/1985 |
| GB | 2 214 814 A | 9/1989 |
| GB | 2 268 690 A | 1/1994 |
| GB | 2 353 220 | 2/2001 |
| GB | 2 359 256 | 8/2001 |
| JP | 61-9601 | 11/1983 |
| JP | 63 095945 | 4/1988 |
| JP | 63-197443 | 8/1988 |
| JP | 6-114067 | 4/1994 |
| SE | 503 271 | 3/1996 |
| SE | 506 164 | 4/1997 |
| SU | 990 220 A | 1/1983 |
| WO | 88/01853 | 3/1988 |
| WO | 89/04674 A | 6/1989 |
| WO | 89/10096 | 11/1989 |
| WO | 91/02493 | 3/1991 |
| WO | 92/05828 | 4/1992 |
| WO | 92/16152 | 10/1992 |
| WO | 92/21298 | 12/1992 |
| WO | 93/10715 | 6/1993 |
| WO | 93/10731 | 6/1993 |
| WO | 93/19678 | 10/1993 |
| WO | 94/04080 | 3/1994 |
| WO | 94/05223 | 3/1994 |
| WO | 94/19029 | 9/1994 |
| WO | 94/28799 | 12/1994 |
| WO | 95/05129 | 2/1995 |
| WO | 96/06567 | 3/1996 |
| WO | 96/25887 | 8/1996 |
| WO | 96/28100 | 9/1996 |
| WO | 97/06731 | 2/1997 |
| WO | 97/13465 | 4/1997 |
| WO | 97/30638 | 8/1997 |
| WO | 97/41792 | 11/1997 |
| WO | 97/43982 | 11/1997 |
| WO | 98/12971 | 4/1998 |
| WO | 98/35632 | 8/1998 |
| WO | WO-99/63907 | 12/1999 |
| WO | 00/66030 | 11/2000 |
| WO | 00/74594 | 12/2000 |
| WO | 00/74613 | 12/2000 |
| WO | 00/74633 | 12/2000 |
| WO | WO 00/74633 A2 | 12/2000 |
| WO | 01/52750 | 7/2001 |
| WO | WO-02/28315 | 4/2002 |

OTHER PUBLICATIONS

Agarwala et al., "Minimally invasive management of urinary incontinence", Current Opinion in Obstetrics and Gynecology, 2002, vol. 14, No. 4, pp. 429-433.

Araki et al., "The Loop-Loosening Procedure for Urination Difficulties after Stamey Suspension of the Vesical Neck," The Journal of Urology, Aug. 1990, vol. 144, pp. 319-323.

Bayer et al., "A New Approach to Primary Strengthening of Colostomy with Marlex® Mesh to Prevent Paracolostomy Hernia," Surgery, Gynecology & Obstetrics, Dec. 1986, vol. 163, pp. 579-580.

Beck et al., "A 25-Year Experience with 519 Anterior Colporrhaphy Procedures," Obstetrics & Gynecology, Dec. 1991, vol. 78, No. 6, pp. 1011-1018.

Blaivas, "Successful Pubovaginal Sling Surgery," Contemporary Urology, Jul. 1993, pp. 40-63.

Blaivas, "Pubovaginal Fascial Sling for the Treatment of Complicated Stress Urinary Incontinence," The Journal of Urology, Jun. 1991, vol. 145, pp. 1214-1218.

Benderev, "A Modified Percutaneous Outpatient Bladder Neck Suspension System," The Journal of Urology, Dec. 1994, vol. 152, pp. 2316-2320.

Benderev, "A New Endoscopic Bladder Neck Suspension for the Outpatient Treatment of Stress urinary Incontinence," The Journal of Urology, Apr. 1993, No. 4, videotape, V-40, p. 197A.

Benderev, "Anchor Fixation and Other Modifications of Endoscopic Bladder Neck Suspension," Urology, 1992, vol. 40, No. 5, pp. 409-418.

Brenner, "Mesh Materials in Hernia Repair," Expert Meeting on Hernia Surgery, St. Moritz, 1994. Basel Karger, 1995, pp. 172-179.

Cruikshank, "Reconstructive Procedures for the Gynecologic Surgeon," American Journal of Obstetrics and Gynecology, Feb. 1993, vol. 168, No. 2, pp. 469-475.

DeLancey, "Structural Support of the Urethra as it Relates to Stress urinary Incontinence: The Hammock Hypothesis," American Journal of Obstetrics and Gynecology, Jun. 1994, vol. 170, No. 6, pp. 1713-1723.

Falconer et al., "Clinical Outcome and Changes in Connective Tissue Metabolism after Intravaginal Slingplasty in Stress Incontinent Women," The International Urogynecology Journal, 1996, vol. 7, 133-137.

Forneret et al., "Cost-Effective Treatment of Female Stress Urinary Incontinence: Modified Pereyra Bladder Neck Suspension," Urology, Apr. 1985, vol. 25, No. 4, pp. 365-367.

Gittes et al., "No-Incision Pubovaginal Suspension for Stress Incontinence," The Journal of Urology, Sep. 1987, vol. 138, pp. 568-570.

Hancock et al., "Transpubic Suspension of the Bladder Neck for Urinary Incontinence," The Journal of Urology, May 1980, vol. 123, pp. 667-668.

Hoffman et al., "Transvestibular Retropubic Bladder Neck Suspension: A Pilot Study," The Journal of Reproductive Medicine, Mar. 1995, vol. 40, No. 3, pp. 181-184.

Iglesia et al., "The Use of Mesh in Gynecologic Surgery," International Urogynecology Journal, 1997, vol. 8, pp. 105-115.

Kovac et al., "Pubic Bone Suburethral Stabilization Sling for Recurrent Urinary Incontinence," Obstetrics & Gynecology, Apr. 1997, vol. 89, No. 4, pp. 624-627.

Leach et al., "Percutaneous Bladder Neck Suspension," Urologic Clincs of North America, Aug. 1996, vol. 23, No. 3, pp. 511-516.

Leach, "Bone Fixation Technique for Transvaginal Needle Suspension", Urology, May 1988, vol. 31, No. 5, pp. 388-390.

Leach et al., "Modified Pereyra Bladder Neck Suspension after Previously Failed Anti-Incontinence Surgery," Urology, Apr. 1984, vol. 23, No. 4, pp. 359-362.

Mascio, et al., "Therapy of Urinary Stress Incontinence in Women Using Mitek® GII Anchors," The Mitek Brochure, 1993.

Mattox et al., "Modification of the Miya Hook in Vaginal Colpopexy," The Journal of Reproductive Medicine, Oct. 1995, vol. 40, No. 10, pp. 681-683.

McGuire, "The Sling Procedure for Urinary Stress Incontinence" Profiles in Urology.

McKiel et al., Marshall-Marchetti Procedure: Modification, The Journal of Urology, 1966, vol. 96, pp. 737-739.

Mitchell, et al., "Hook Needle and Retractor for Posterior Urethroplasty," British Journal of Urology, 1970, vol. 42, pp. 599-600.

Nativ et al., "Bladder Neck Suspension Using Bone Anchors for the Treatment of Female Stress Incontinence," ASAIO Journal, 1997, pp. 204-208.

Nichols et al., "Identification of Pubourethral Ligaments and their Role in Transvaginal Surgical Correction of Stress Incontinence," American Journal of Obstetrics and Gynecology, Jan. 1973, vol. 115, No. 1, pp. 123-128.

Petros, "The Intravaginal Slingplasty Operation, a Minimally Invasive Technique for Cure of Urinary Incontinence in the Female," Aust. And N.Z. Journal of Obstetrics and Gynecology, 1996, vol. 4, pp. 453-461.

Petros, "Ambulatory Surgery for Urinary Incontinence and Vaginal Prolapse," The Medical Journal of Australia, Jul. 1994, vol. 161, pp. 171-172.

Pereyra, "A Simplified Surgical Procedure for the Correction of Stress Incontinence in Women," West. J. Surg. Obstetrics and Gynecology, Jul.-Aug. 1959, pp. 223-226.

Raz, "Modified Bladder Neck Suspension for Female Stress incontinence," Urology, Jan. 1981, vol. 17, No. 1, pp. 82-85.

Riachi et al., "Repeat Tension-Free Transvaginal Tape (TVT) Sling for the Treatment of Recurrent Stress Urinary Incontinence", International Urogynecology Journal, 2002, vol. 13, No. 2, pp. 133-135.

Richardson et al., "Treatment of Stress Urinary Incontinence Due to Paravaginal Fascial Defect," Obstetrics & Gynecology, Mar. 1981, vol. 57, No. 3, pp. 357-362.

Richmond et al., "Modification of the Bankart Reconstruction with a Suture Anchor," The American Journal of Sports Medicine, 1991, vol. 19, No. 4, pp. 343-346.

Robertson et al., "Soft Tissue Fixation to Bone," The American Journal of Sports Medicine, 1986, vol. 14, No. 5, pp. 398-403.

Schaeffer et al., "Endoscopic Suspension of Vesical Neck for Urinary Incontinence," Urology, May 1984; vol. 23, No. 5, pp. 484-494.

Schatzker et al., "The Rationale of Operative Fracture Care," 1987, pp. XIV-XV and 159.

Scheuer, "The Modified Pereyra Bladder Neck Suspension Procedure Using Mitek® GII Anchors," The Mitek Brochure, 1993.

Spencer et al., "A Comparison of Endoscopic Suspension of the Vesical Neck with Suprapubic Vesicourethropexy for Treatment of Stress Urinary Incontinence," The journal of Urology, Mar. 1987, vol. 137, pp. 411-415.

Stamey, "Endoscopic Suspension of the Vesical Neck for Urinary Incontinence in Females," Ann. Surg., Oct. 1980, vol. 192, No. 4, pp. 465-471.

Stamey, "Endoscopic Suspension of the Vesical Neck," 1986, pp. 115-132.

Stamey, "Endoscopic Suspension of the Vesical Neck for Urinary Incontinence," Surgery, Gynecology & Obstetrics, Apr. 1973, vol. 136, No. 4, pp. 547-554.

Trockman et al., "Modified Pereyra Bladder Neck Suspension: 10-Year Mean Follow Up Using Outcomes Analysis in 125 Patents," The Journal of Urology, Nov. 1995, vol. 154, pp. 1841-1847.

Ulmsten et al., "An Ambulatory Surgical Procedure Under Local Anesthesia for Treatment of Female Urinary Incontinence," International Urogynecology Journal, 1996, vol. 7, pp. 81-86.

Ulmsten et al., "Intravaginal Slingplasty (IVS): An Ambulatory Surgical Procedure for Treatment of Female Urinary Incontinence," Scandinavian Journal of Urology and Nephrology, Mar. 1995, vol. 29, No. 1, pp. 75-82.

Urken, "About Lifecell—Our Science," Lifecell, 2001.

Vasavada et al., "Incisionless Pubovaginal Fascial Sling Using Transvaginal Bone Anchors for the Treatment of Stress Urinary Incontinence," Digital Urology Journal, 2001.

Webster, "Female Urinary Incontinence," Urologic Surgery, 1983, Third Edition, pp. 665-679.

Webster et al., "Voiding Dysfunction Follow-up Cystourethropexy: Its Evaluation and Management," The Journal of Urology, Sep. 1990, vol. 44, pp. 670-673.

Winter, "Peripubic Urethropexy for Urinary Stress Incontinence in Women," Urology, Oct. 1982, vol. 20, No. 4, pp. 408-411.

Zimmern et al., "A Prospective Evaluation of Four-Corner Bladder Neck Suspension for Grade II/III Cystocele Repair," Neurology and Urodynamics, 1990, vol. 9, pp. 195 and 231.

Zimmern et al., "Transvaginal Closure of the Bladder Neck," Seminars in Urology, Feb. 1986, vol. 4, No. 1, pp. 30-32.

Zacharin, "Abdonimoperineal Urethral Suspension in the Management of Recurrent Stress Incontinence of Urine—A 15-Year Experience," Obstetrics & Gynecology, Nov. 1983, vol. 62, No. 5, pp. 644-654.

Falconer et al., "Clinical Outcome and Changes in Connective Tissue Metabolism after Intravaginal Slingplasty in Stress Incontinent Women", International Urogynecology Journal, 1996, vol. 7, pp. 133-137.

Fianu et al., "Absorbable Polyglactin Mesh for Retropubic Sling Operations in Female Urinary Stress Incontinence", Scandinavian Journal of Urology and Nephrology, Mar. 1985, vol. 29, No. 1, pp. 45-50.

Henriksson et al., "A Urodynamic Comparison between Abdominal Urethrocystopexy and Vaginal Sling Plasty in Female Stress Incontinence", Urologia Internationalis, 1978, vol. 33, No. 1-3, pp. 111-116.

Henriksson, et al., "A urodynamic evaluation of the effects of abdominal urethrocystopexy and vaginal sling urethroplasty in women with stress incontinence", American Journal of Obstetrics and Gynecology, 1978, vol. 131, No. 1, pp. 77-82.

Iosif et al., "Urodynamic studies of women with prolapse and stress incontinence before and after surgical repair", Zentralblatt für Gynäkologie, 1979, vol. 101, pp. 1433-1442.

Kersey, "The gauze hammock sling operation in the treatment of stress incontinence", British Journal of Obstetrics and Gynaecology, Oct. 1983, vol. 90, pp. 945-949.

Petros et al., "An Integral Theory and its Method for the Diagnosis and Management of Female Urinary Incontinence", Scandinavian Journal of Urology and Nephrology, 1993, Supplement No. 153.

Petros et al., "The Autogenic Ligament Procedure: A Technique for Planned Formation of an Artificial Neo-Ligament", Acta Obstetricia et Gynecologica Scandinavica, 1990, vol. 69, Supplement 153, pp. 43-51.

Petros, "The Intravaginal Slingplasty Operation, a Minimally invasive Technique for Cure of Urinary Incontinence in the Female", Aust. NZ Journal of Obstetrics & Gynaecology, 1996, 36:4, pp. 453-461.

Petros et al., "The Tuck Procedure: A Simplified Vaginal Repair for Treatment of Female Urinary Incontinence", Acta Obstetricia et Gynecologica Scandinavica, 1990, vol. 69, Supp. 153, pp. 41-42.

Petros et al., "Urethral Pressure Increase on Effort Originates from within the Urethra, and Continence from Musculovaginal Closure", Neurourology and Urodynamics, 1995, vol. 14, No. 4, pp. 337-350.

Rezapour et al., "Tension-Free Vaginal Tape (TVT) in Woman with Recurrent Stress Urinary Incontinence—A Long-term Follow up", International Urogynecology Journal, 2001, vol. 12 (Suppl 2), pp. S9-S11.

Ulmsten et al., "An Ambulatory Surgical Procedure Under Local Anesthesia for Treatment of Female Urinary Incontinence", International Urogynecology Journal, 1996, vol. 7, pp. 81-86.

Ulmsten et al., "A three-year follow up of tension free vaginal tape for surgical treatment of female stress urinary incontinence", British Journal of Obstetrics and Gynaecology, Apr. 1999, vol. 106, pp. 345-350.

Ulmsten et al., "Intravaginal Slingplasty", Zentralbl Gynakol, 116 (1994), pp. 398-404.

Ulmsten et al., "Intravaginal Slingplasty (IVS): An Ambulatory surgical Procedure for Treatment of Female Incontinence", Scand J Urol Nephrol, 1995, vol. 29, pp. 75-82.

Wang et al., "Tension-Free Vaginal Tape, A Minimally Invasive Solution to Stress Urinary Incontinence in Women", The Journal of Reproductive Medicine, May 1998, vol. 43, No. 5, pp. 429-434.

Patent Cooperation Treaty, International Search Report, International Application No. PCT/US02/07076, mailed on Oct. 17, 2002, 10 pages.

U.S. Appl. No. 10/092,872, filed Mar. 7, 2002, Gellman et al.
U.S. Appl. No. 10/093,498, filed Mar. 7, 2002, Gellman et al.
U.S. Appl. No. 10/093,450, filed Mar. 7, 2002, Gellman et al.
U.S. Appl. No. 10/093,371, filed Mar. 7, 2002, Gellman et al.
U.S. Appl. No. 10/094,352, filed Mar. 7, 2002, Gellman et al.
U.S. Appl. No. 10/093,424, filed Mar. 7, 2002, Gellman et al.

Tension-Free Support for Incontinence, 1, 2, 3, 4, 5 Years of Proven Performance, Lasting freedom for your SUI patients, Gynecare TVT, 6 pages (2002).

The essence of a contemporary synthetic sling self-anchoring complete adjustability elastic, Safyre™ Autofixation System, Promedon, 4 pages (2002).

The Tension-Free Solution to Female Incontinence, Gynecare TVT, 4 pages.

A Superior Approach to Tensionless Sling Placement, SPARC sling system for stress urinary incontinence, American Medical Systems, Inc., 4 pages (2001).

IVS Tunneller—A Universal Instrument for Intra-Vaginal Tape Placement, Tyco Healthcare UK Limited, 4 pages.

Falk et al., United States Statutory Invention Registration, Reg. No. H1028, Mar. 3, 1992, United States Patent Office, Washington D.C.

Mattox, T.F., et al., "Modification of the Miya Hook in Vaginal Colpopexy," The Journal of Reproductive Medicine, 40(10):681-683 (1995).

Urology, Mitchell, J.P., "Hook Needle and Retractor for Posterior Urethroplasty," British Journal of Urology, 42:599-600 (1970).

Amid, Parviz K., et al., "Experimental evaluation of a new composite mesh with the selective property of incorporation to the abdominal wall without adhering to the intestines", Journal of Biomedical Materials Research, vol. 28, pp. 373-375 (1994).

Carachi, R., et al., "Collagen-Coated Vicryl Mesh: A New Bioprosthesis in Pediatric Surgical Practice", Journal of Pediatric Surgery, vol. 30, No. 9 pp. 1302-1305 (1995).

DeLorme, "La bandelette trans-obturatrice: un procede mini-invasif pour trailer l'incontinence urinair d'effort de la femme", Progres en Urologie, vol. 11, pp. 1306-1313, 2001 (English summary therein).

Giesy et al., "Ureteral Instrumentation: A New System for Continued Access via a Safety Guidewire", The Journal of Urology, No. 4, Part 2, p. 282A, Apr. 1988.

Haab et al., "Feasibility of Outpatient Percutaneous Bladder Neck Suspension Under Local Anesthesia," Urology, vol. 50, pp. 585-587, 1997.

Jacquetin, B., "Utilisation du TVT dans la chirurgie de l'incontinence urinaire feminine", J. Gynecol Obste Biol Reprod 2000, vol. 29, pp. 242-247 (English summary therein).

Norris et al., "Use of Synthetic Material in Sling Surgery: A Minimally Invasive Approach", Journal of Endourology, vol. 10, No. 3, Jun. 1996.

Petros, P., "An Integral Theory of Bladder Neck Opening, Closure and Urinary Incontinence int he Female", International Journal of Gynecology & Obstetrics, XXIII World COngress of Gynaecology and Obstetrics (FIGO) 1991.

Petros, "Medium-term Follow-up of the Intravaginal Slingplasty Operation Indicates Minimal Deterioration of Urinary Continence With Time", Aust. And N.Z. Journal of Obstetrics and Gynecology, vol. 39, pp. 354-356, 1999.

Raz et al., "Fascial Sling to Correct Male Neurogenic Sphincter Incompetence: The McGuire/Raz Approach", The Journal of Urology, vol. 139, pp. 528-531, 1988.

Raz et al., "Vaginal Wall Sling", The Journal of Urology, vol. 141, No. 1, pp. 43-46, Jan. 1989.

Staskin, "Sling Surgery for the Treatment of Female Stress Incontinence", Problems in Urology, vol. 5, No. 1, pp. 106-122, Mar. 1991.

Staskin et al., "The Gore-tex sling procedure for female sphincteric incontinence: indications, technique, and results", World Journal of Urology, vol. 15, No. 5, pp. 295-299, 1997.

Sussman et al., "The Raz Bladder Neck Suspension: Five Year Experience", The Journal of Urology, vol. 145, p. 223A, 1993.

Ulmsten et al., "Connective Tissue Factors in the Aetiology of Female Pelvic Disorders", Ann. Med., vol. 22, No. 6, p. 3, Dec. 1990.

Ulmsten et al., "Surgery for Female Urinary Incontinence", Current Opinion in Obstetrics & Gynecology, vol. 4, No. 3, pp. 456-462, 1992.

Ulmsten et al., "A Multicenter Study of Tension-Free Vaginal Tape (TVT) for Surgical Treatment of Stress Urinary Incontinence", International Urogynecology Journal, vol. 9, No. 4, pp. 210-213, 1998.

Ulmsten, "An Introduction to Tension-Free Vaginal Tape (TVT)—A New Surgical Procedure for Treatment of Female Urinary Incontinence", International Urogynecology Journal, vol. 12, Suppl. 2, pp. S3-S4, 2001.

Ulmsten, "The Basic Understanding and Clinical Results of Tension-Free Vaginal Tape for Stress Urinary Incontinence", Der Urologe [A] Apr. 2001, pp. 269-273.

* cited by examiner

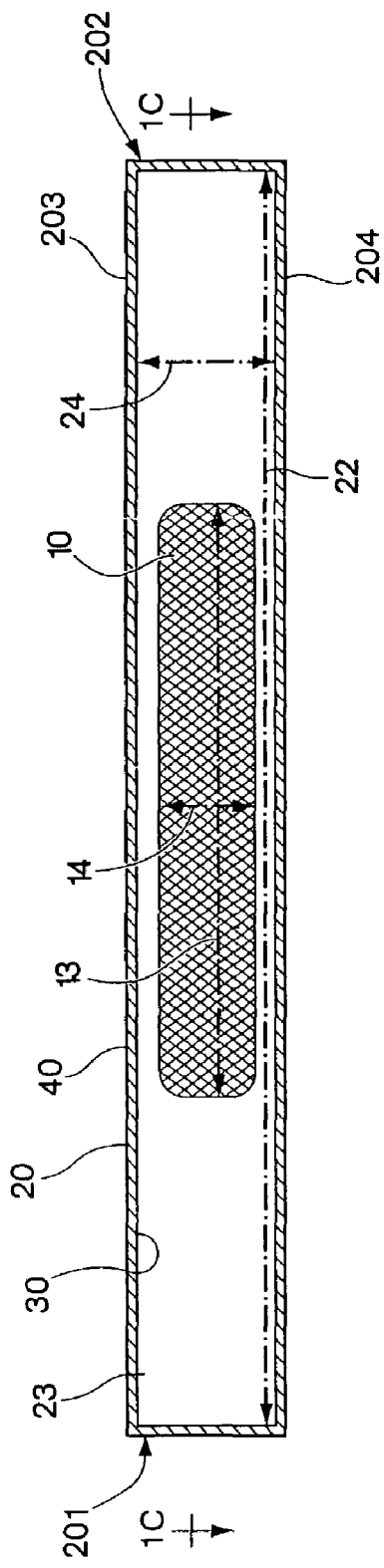
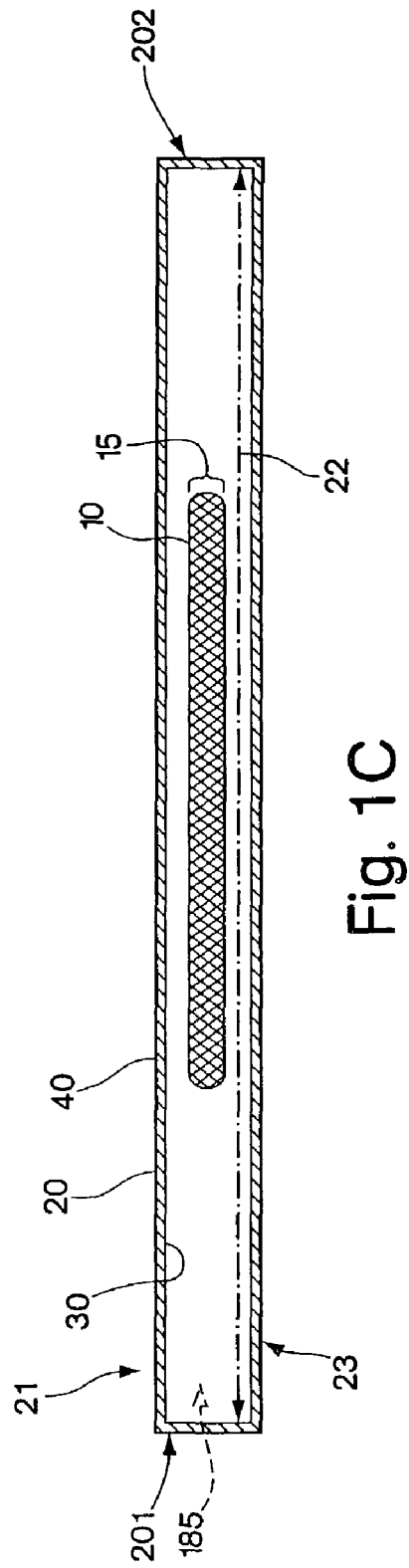
Fig. 1B
Fig. 1C

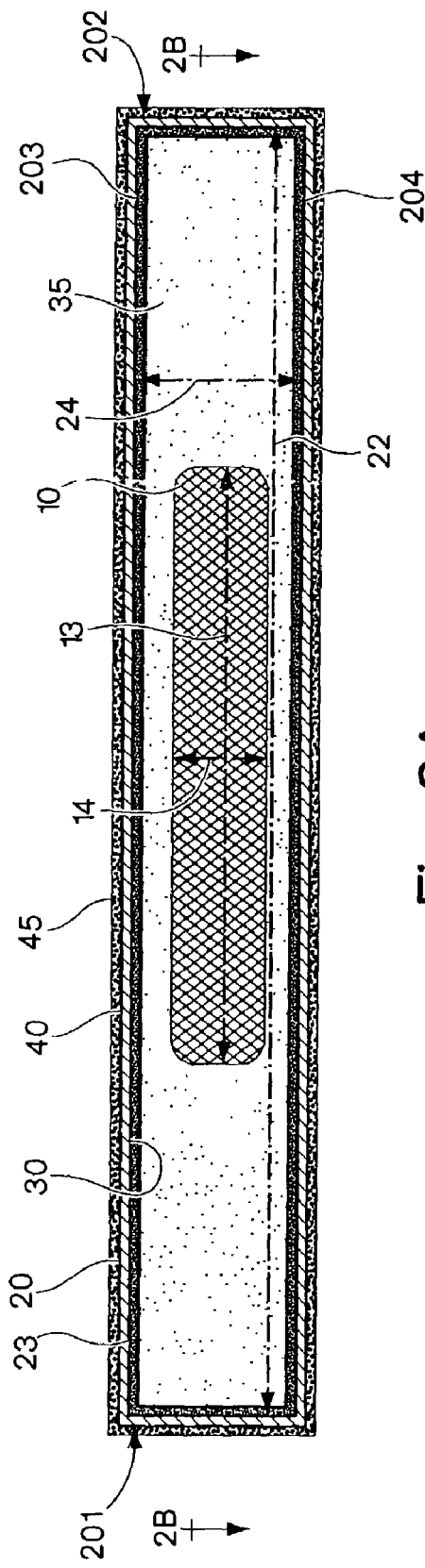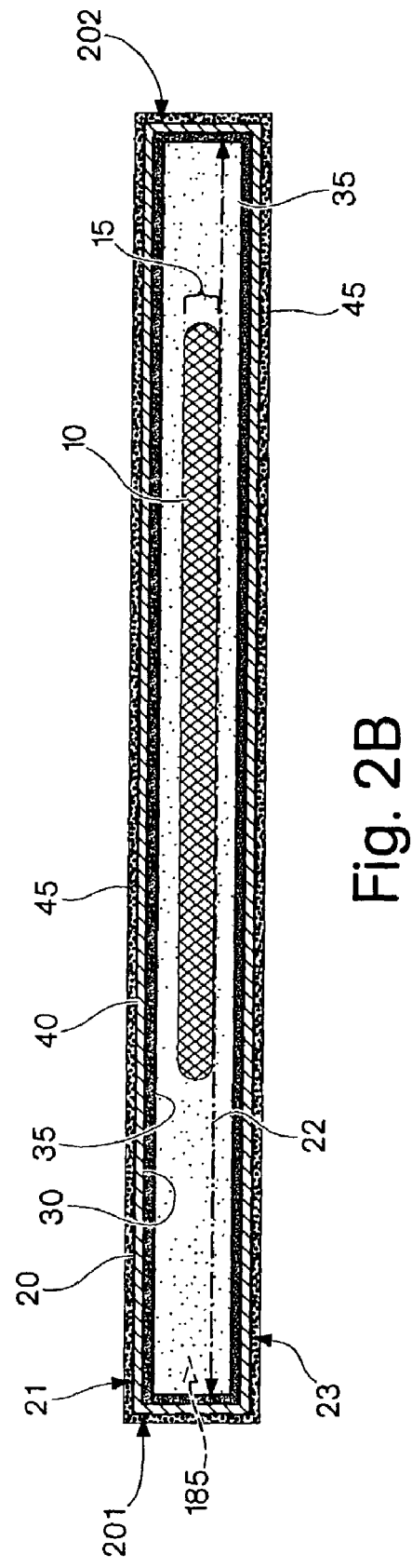
Fig. 2A
Fig. 2B

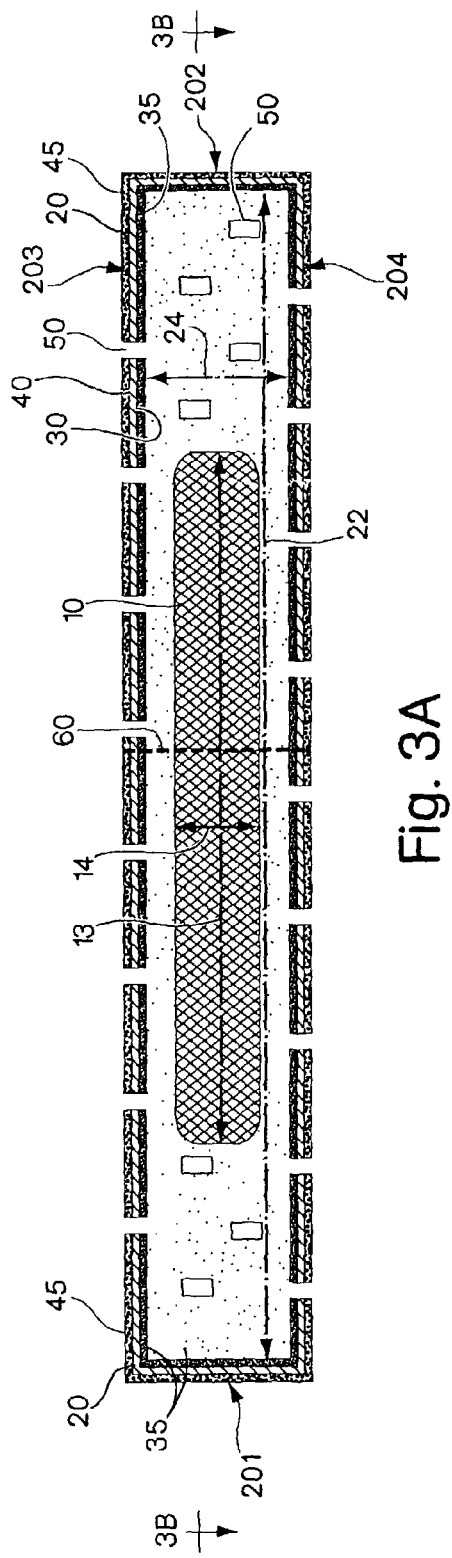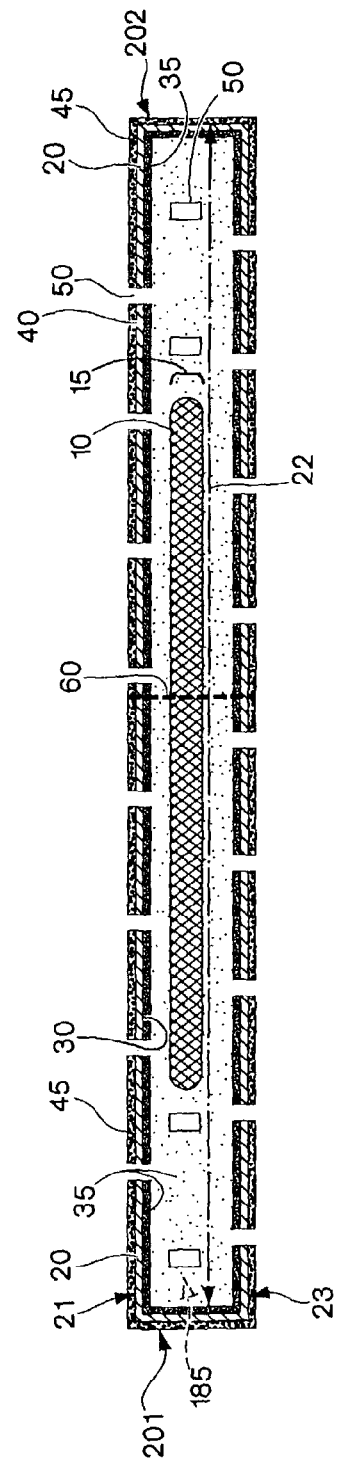
Fig. 3A
Fig. 3B

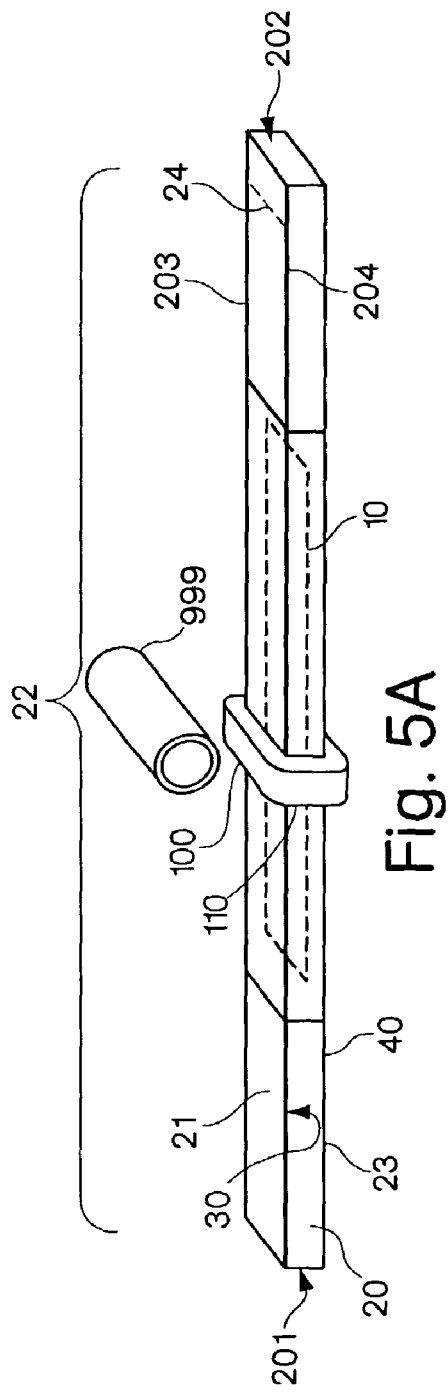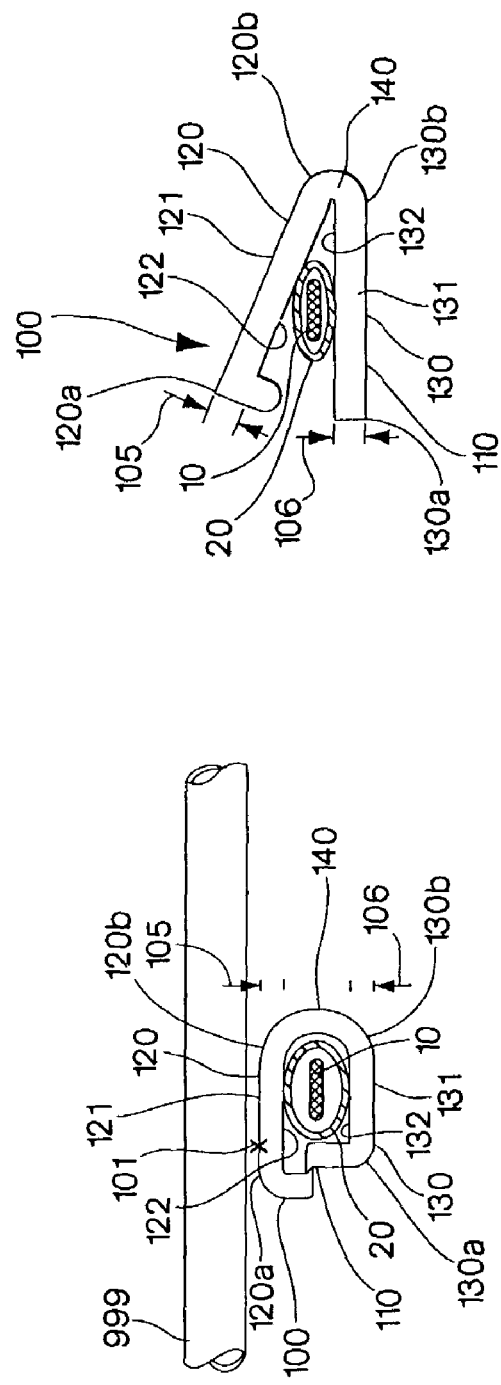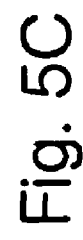

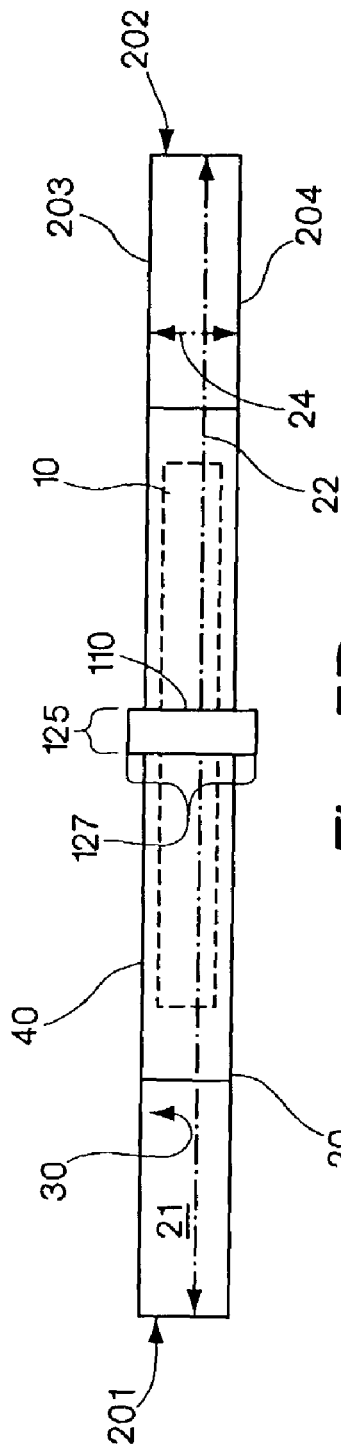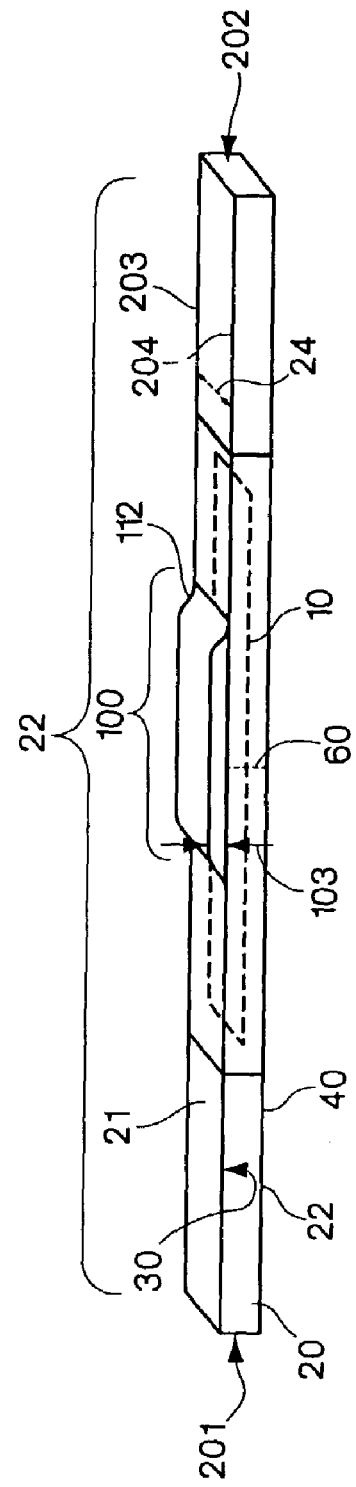

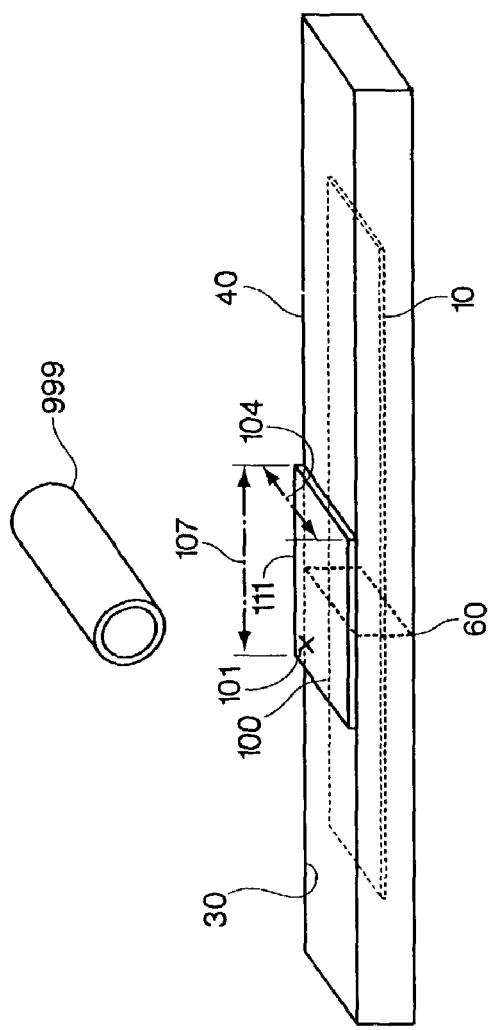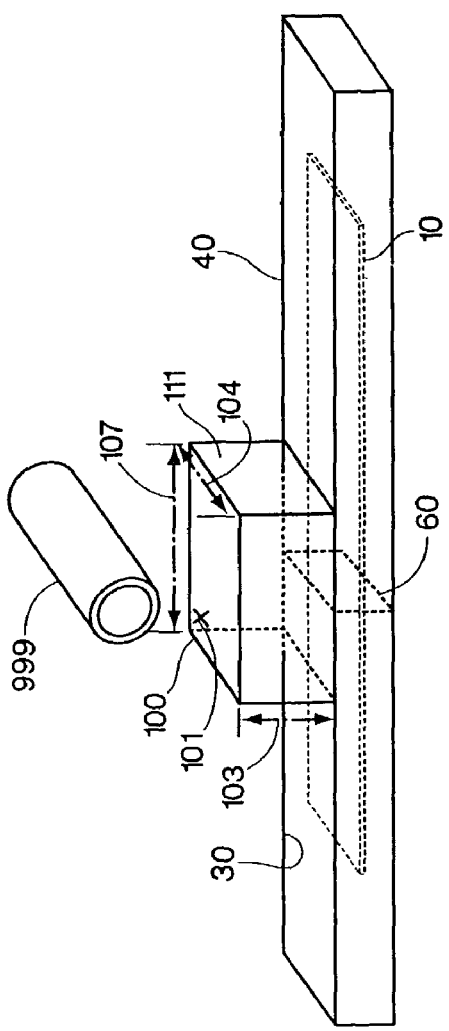

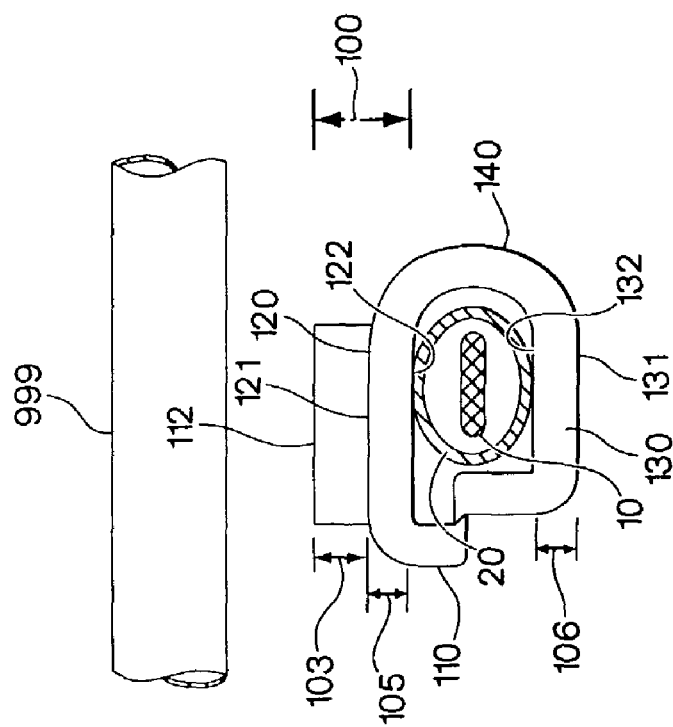
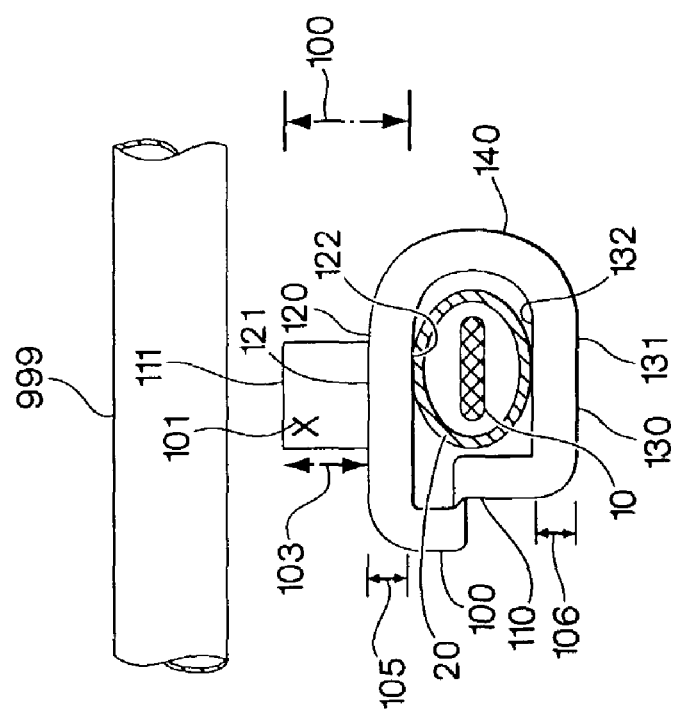

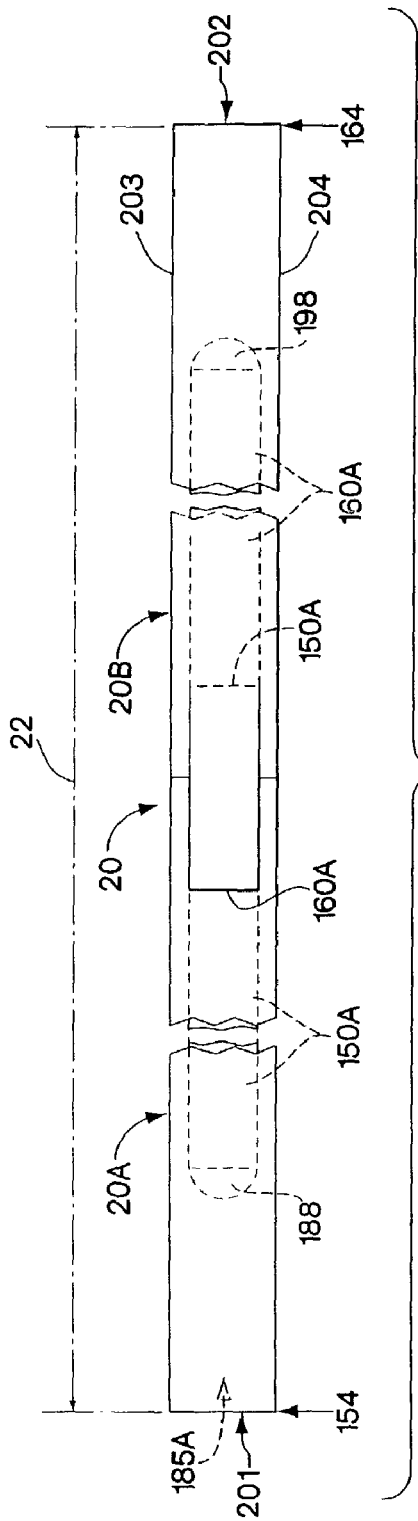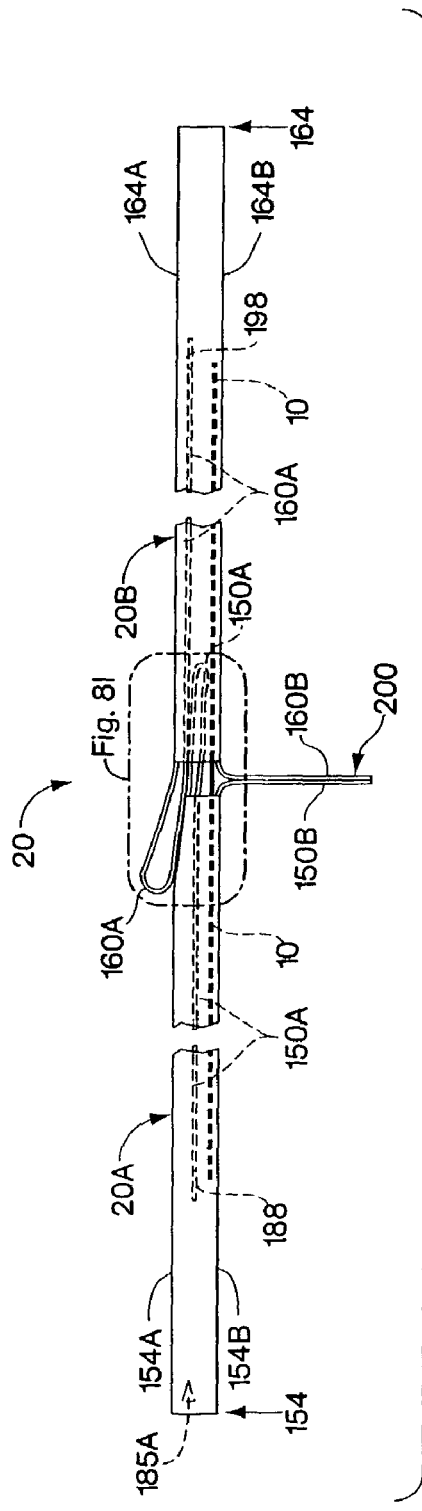

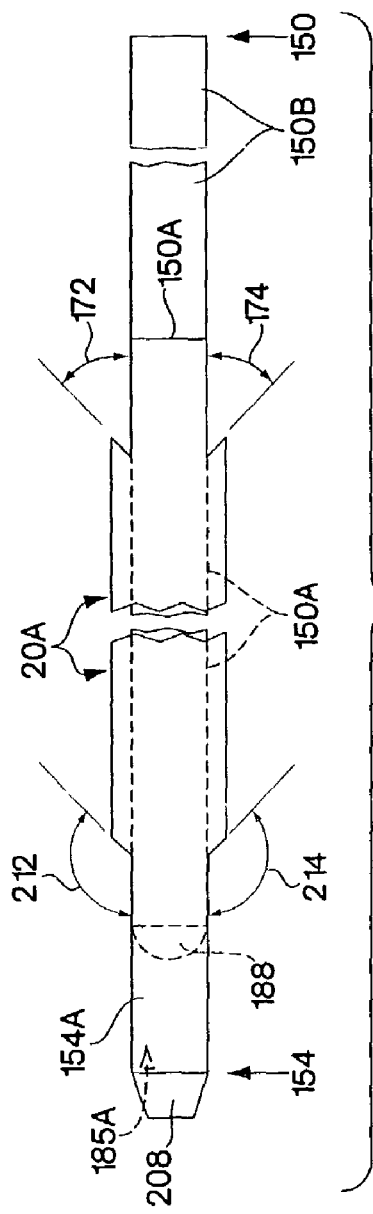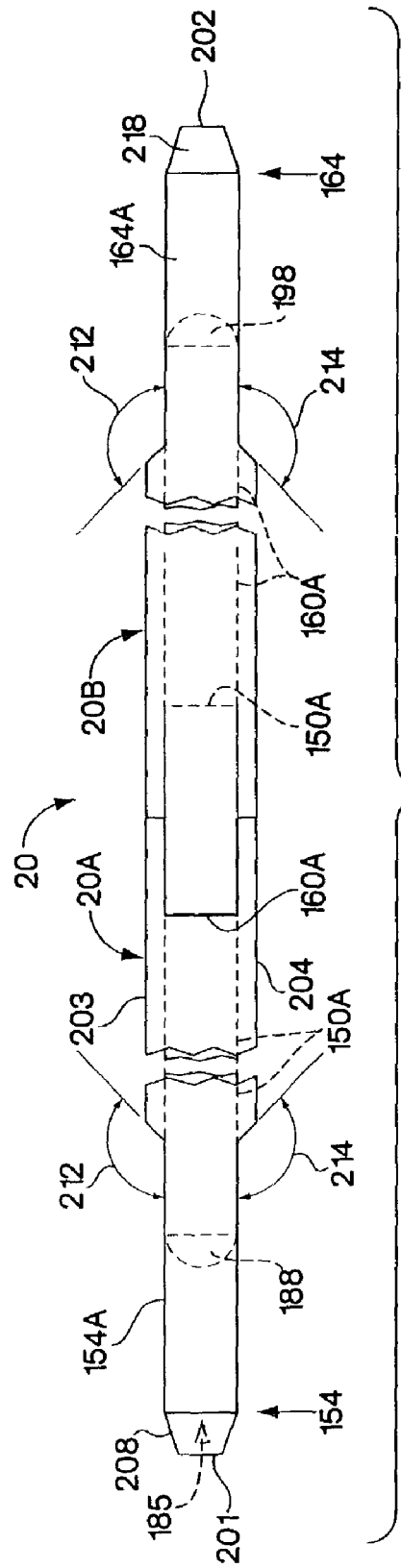

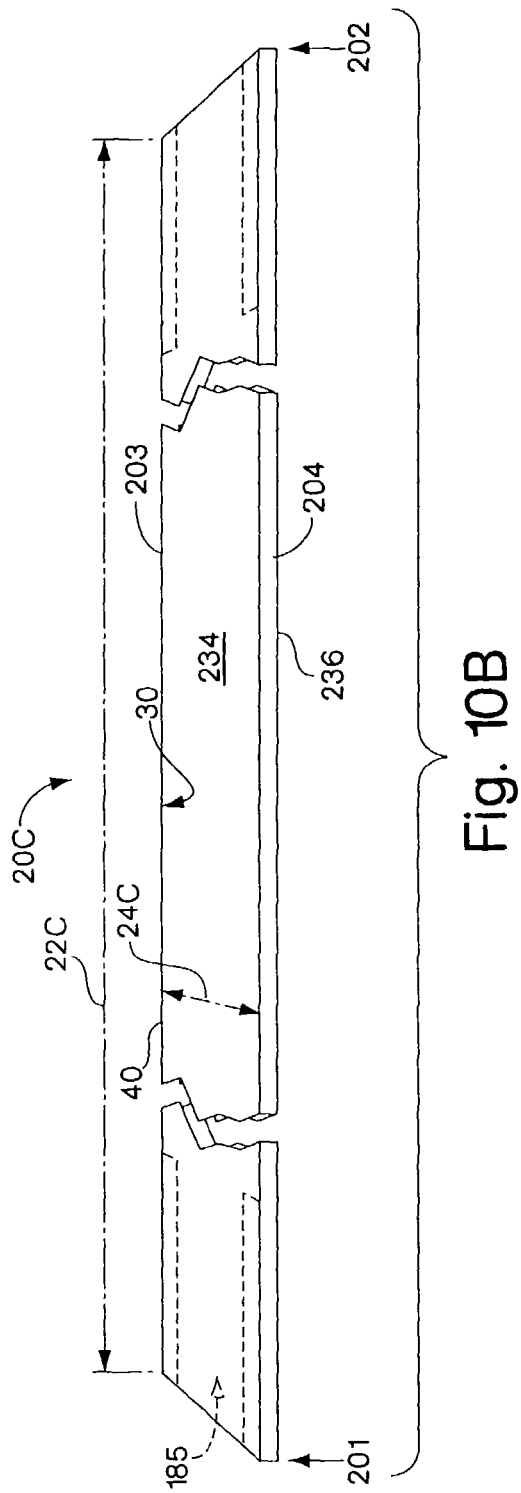
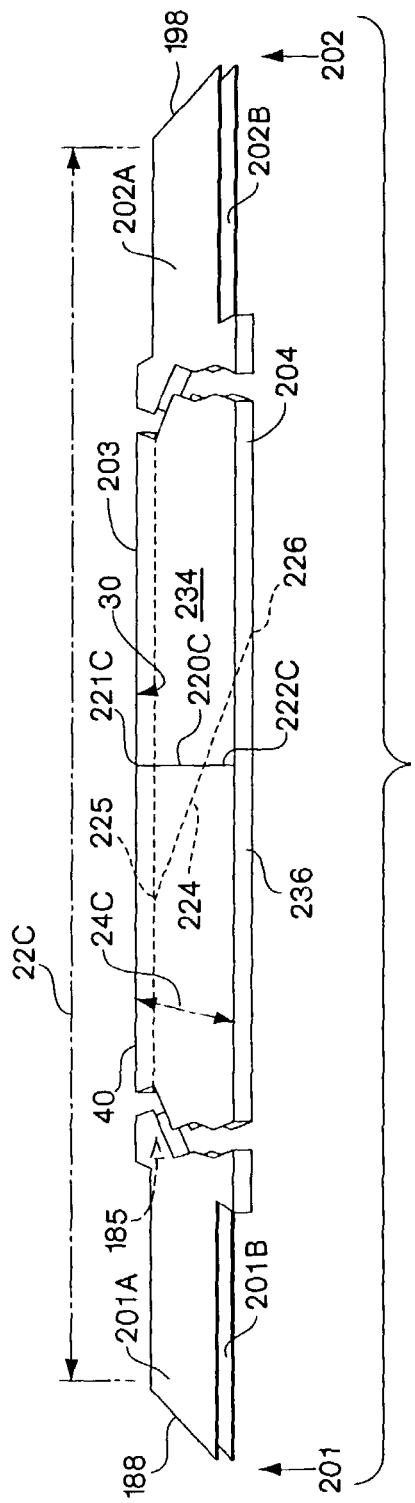
Fig. 10B
Fig. 10C

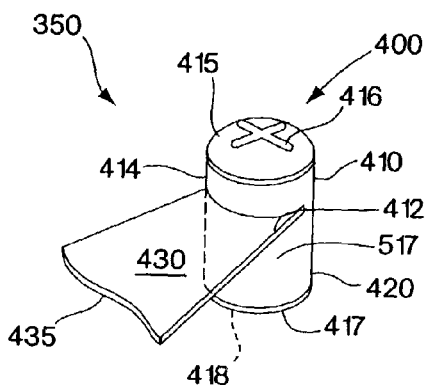
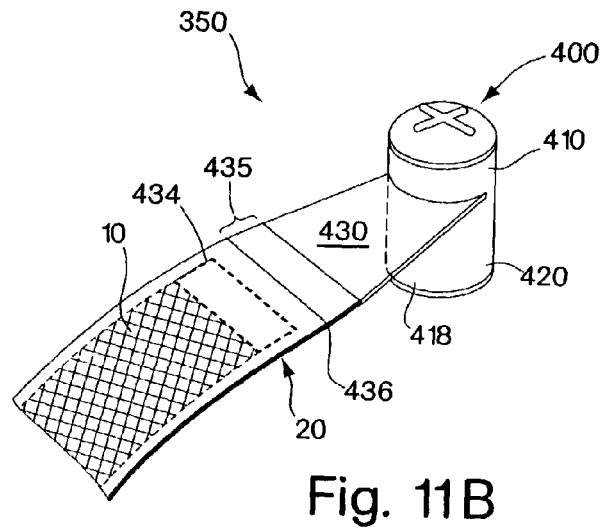
Fig. 11A　　　　　　　　　　Fig. 11B
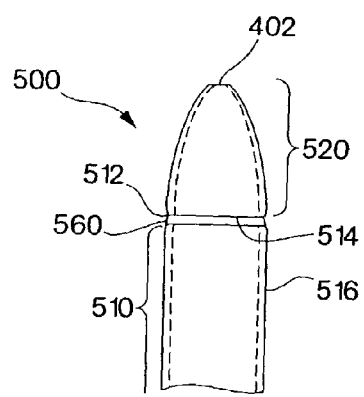
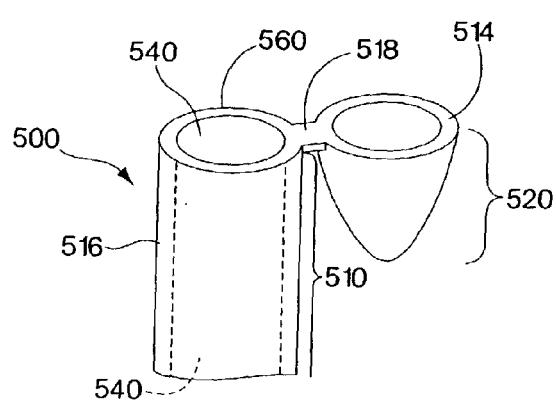
Fig. 12A　　　　　　　　　　Fig. 12B

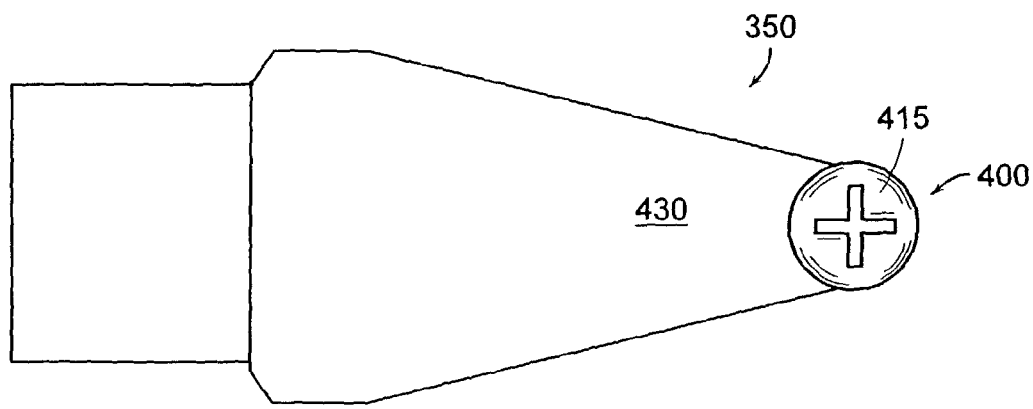
FIG. 11E
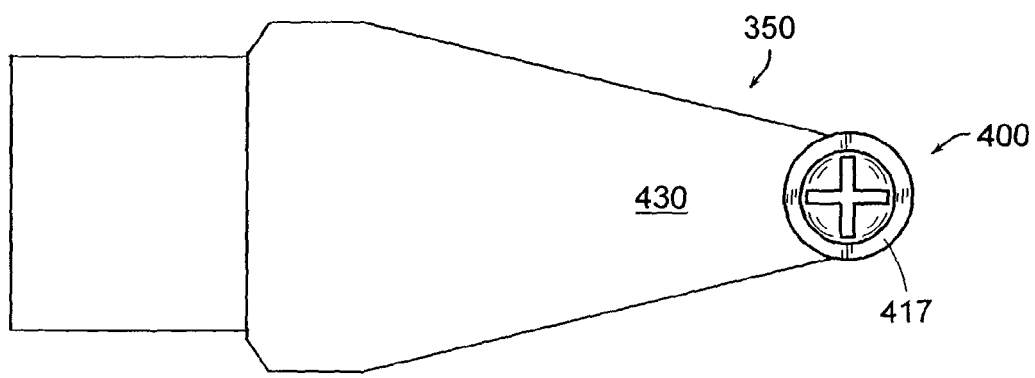
FIG. 11F
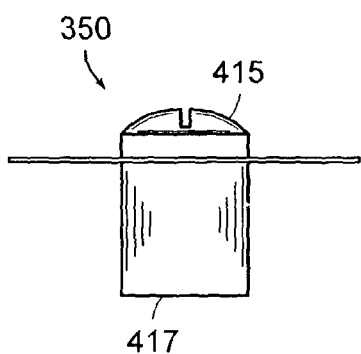 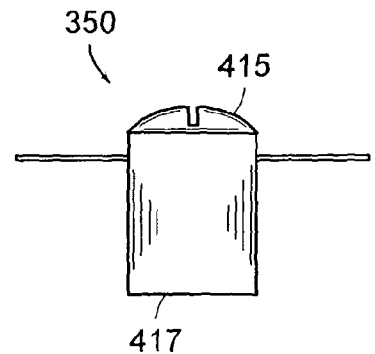
FIG. 11G  FIG. 11H

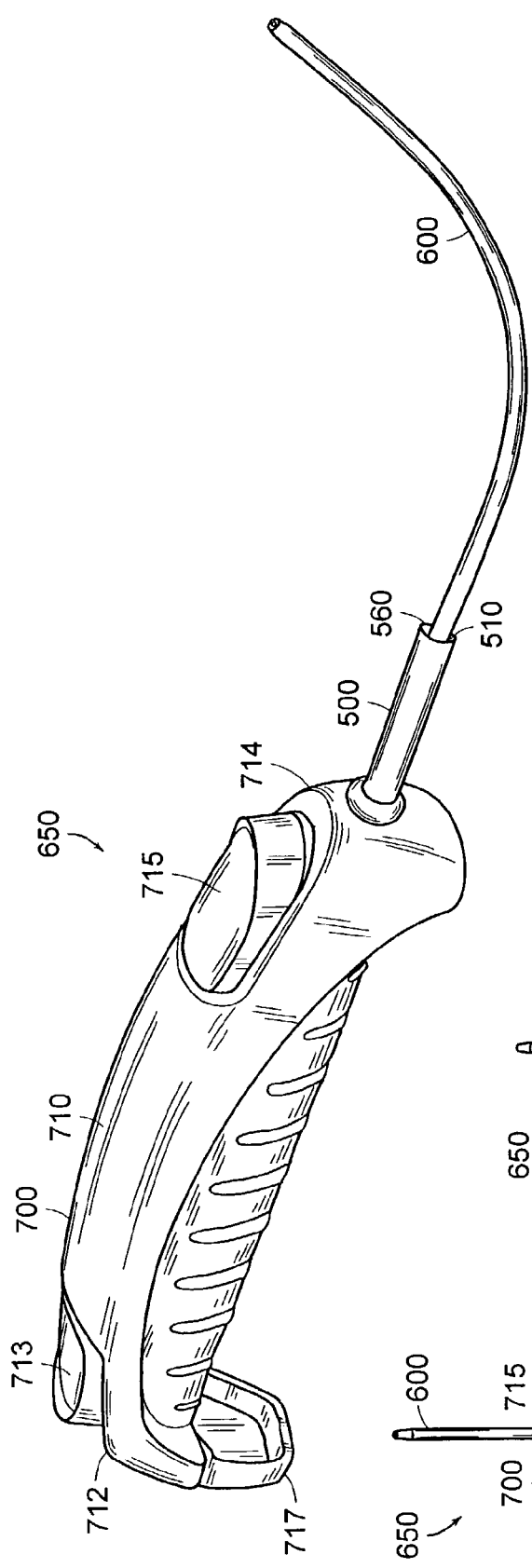
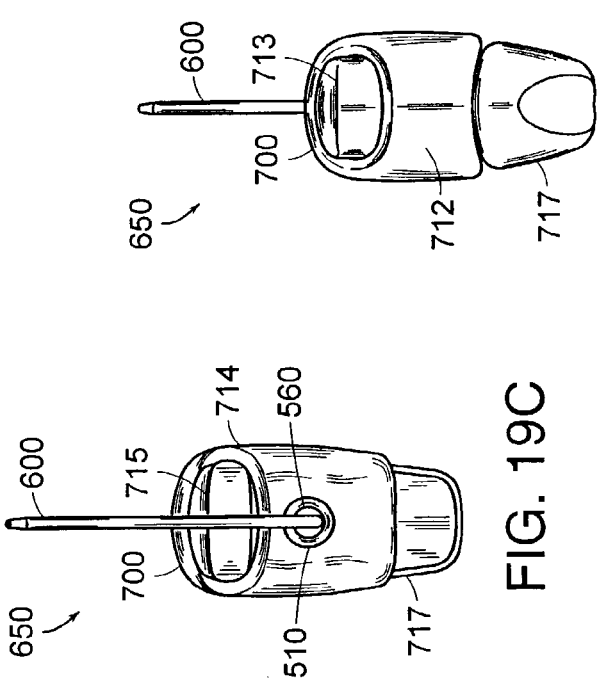
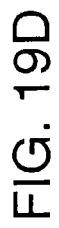
FIG. 19B
FIG. 19C
FIG. 19D

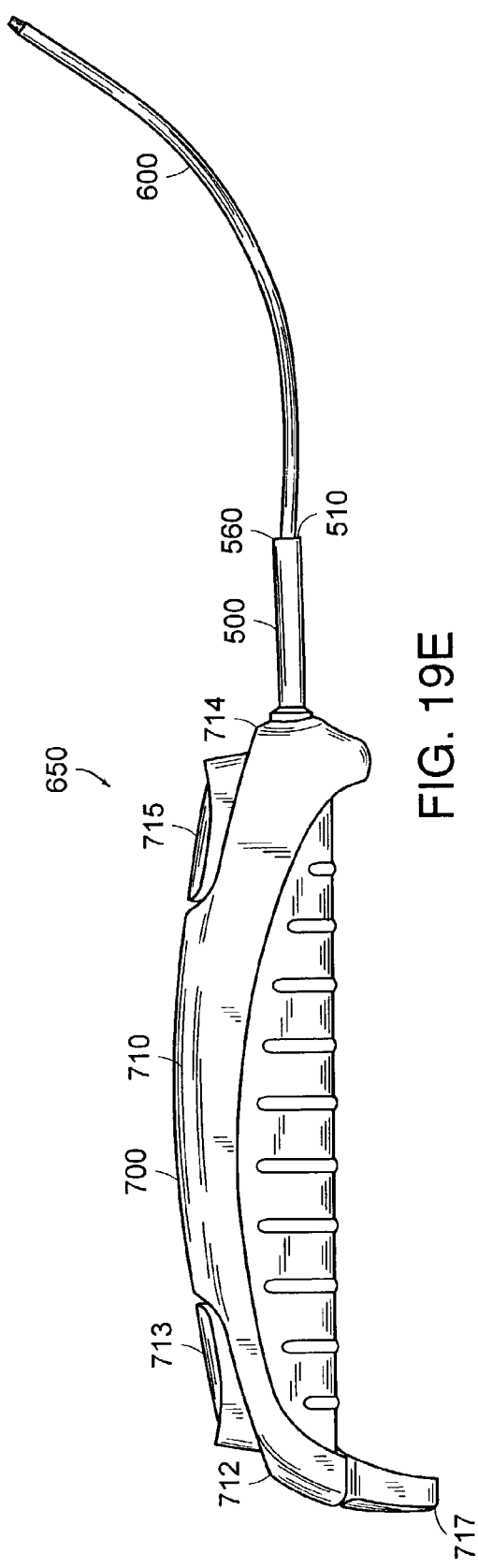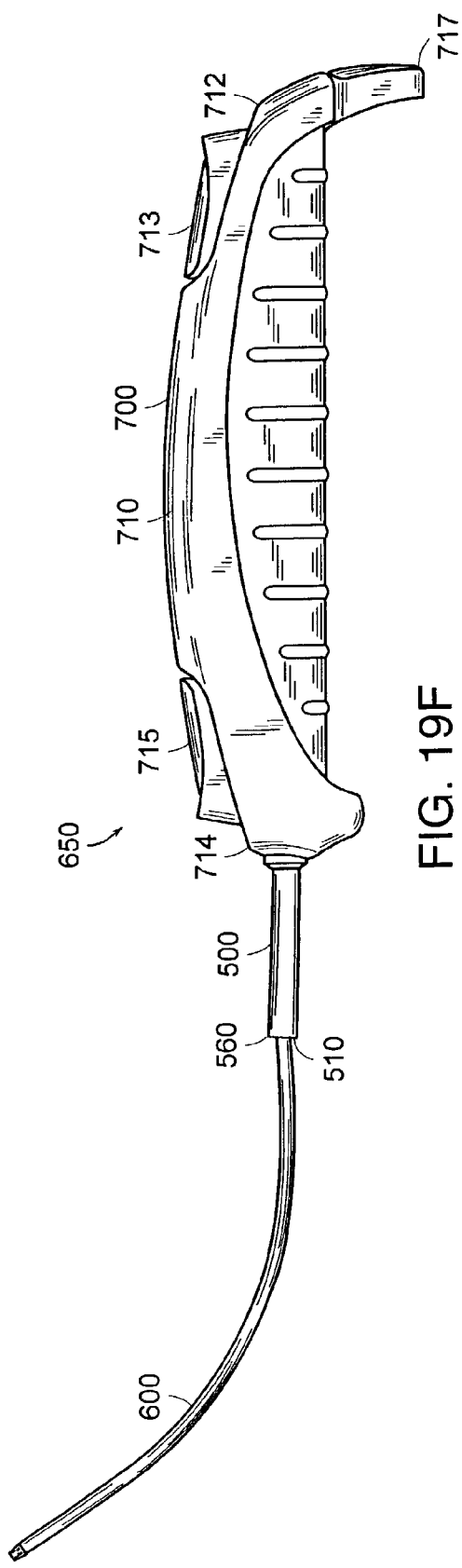
FIG. 19E
FIG. 19F

SYSTEM FOR IMPLANTING AN IMPLANT AND METHOD THEREOF

This application is based on and claims priority to provisional patent application Ser. No. 60/274,843 filed in the United States Patent Office on Mar. 9, 2001 and provisional patent application Ser. No. 60/286,863 filed in the United States Patent Office on Apr. 26, 2001, the entire contents of which are incorporated by reference herein.

TECHNICAL FIELD

The invention relates generally to a system for implanting a device such as a surgical mesh at an anatomical site in the body of a patient. More particularly, the invention relates to a surgical mesh enclosed within an envelope and a system for delivering the envelope and mesh to an anatomical site in the patient's body.

BACKGROUND INFORMATION

The use of a surgical mesh for the repair and restoration of living tissue is well known. For example, surgical mesh may be used to support and/or reinforce a damaged or weakened portion in the body of a patient. In this regard, the surgical mesh must additionally be sufficiently porous to allow for growth of tissue through the mesh after implantation. The healing tissue grows through porous openings in, for example, an implanted synthetic mesh, thereby assimilating the tissue with the mesh and adding structural integrity to the tissue.

Surgical meshes may be produced with yarns including monofilament and multifilament yarns. Multifilament yarns have small void areas or interstitial spaces between the yarn filaments. The yarns in the surgical mesh may be made of materials such as polypropylene, polyesters, and co-polymers thereof. Such polymeric materials typically do not have surface structures that are absorbent or adsorbent; thus, meshes made out of such materials are unable to absorb drugs.

The crevices and voids of the surgical mesh may harbor bacteria or other pathogens that contaminate the surgical mesh during implantation. Following implantation of the surgical mesh in the patient, the bacteria or other pathogens harbored in the mesh are introduced to the anatomical site where the surgical mesh is implanted. Typically, the anatomical site being repaired is poorly accessible to antimicrobial drugs applied intraoperatively to combat bacteria or other pathogens that may be picked up and introduced to the anatomical site during the surgery to implant the mesh.

SUMMARY OF THE INVENTION

The present invention relates to devices, delivery systems and methods for implanting an implant, such as a sling, at an anatomical site in the body of a patient, such as at the mid-urethra, and methods of making such devices and delivery systems. The devices and delivery systems are relatively inexpensive, provide effective therapy, and their use requires minimal training. In one embodiment of the invention, the devices, delivery systems, and methods of the invention can be used to treat female urinary incontinence, including stress incontinence. The benefits of the invention described herein include a delivery system that minimizes or prevents contamination of the implant and minimizes or prevents contamination of the patient's tissue while simultaneously introducing a therapeutic agent or drug such as an antibiotic to the patient's tissues during delivery of the implant to the anatomical site.

Moreover, the system according to the invention, allows the operator to adjust and position the implant at the anatomical site in the patient's body and to maintain the correct position of the implant at the anatomical site during and after removal of the delivery system. In addition, the system, according to the invention, provides a simple means for attaching the implant to a delivery assembly. The delivery assembly can be used for a plurality of surgical approaches to the urethra such as used for a transvaginal and a transabdominal approach (e.g., percutaneous) and assists the operator in accurate positioning of the implant at the anatomical site in the patient's body.

In one aspect, the invention includes a system for implanting an implant in a body. In one embodiment of the invention, the delivery system includes a delivery assembly and an attachment piece. In another embodiment, the delivery system further includes an envelope having an inner surface and an outer surface enclosing the implant. At least one of the inner or outer surface of the envelope includes at least one therapeutic agent, for example, an antimicrobial drug, such as an antibiotic. In one embodiment according to the invention, the material used to make the envelope is an absorbent material. Alternatively, the material used to make the envelope is selected from the group including polypropylene, polyethylene, polyester, polytetrafluoroethylene (e.g., TEFLON®), TYVEK®, MYLAR®, and co-polymers, thereof. In yet another embodiment, the envelope may be coated on the inner or the outer surface with a hydrophilic or a hydrophobic agent. The coating may be selected from the group consisting of synthetic coatings and natural coatings, one or more of which may be an absorbent coating.

In one embodiment according to the invention, the envelope includes a tearable region such as a region of the envelope having apertures, for example, slits or cuts. Alternatively, at least a portion of the envelope includes a tearable material, i.e., a material that may be pulled apart into pieces by application of some force, such as a material having a highly oriented molecular orientation, for example, a linear molecular orientation. In yet another embodiment, the envelope is a composite of a first material and a second material, for example, a composite of a tearable material and a material that does not tear. The tearable region may include a seam where a first material of a first side and a second material of a second side are coupled to form an envelope. Alternatively, the tearable region may include an external tab that is adjacent the envelope outer surface. When the tab is pulled the envelope tears. In another embodiment the tearable region includes an internal tab that is enclosed within the inner surface of the envelope. The internal tab tears the envelope when pulled.

In another embodiment of the invention, the envelope includes at least two sleeves. The two sleeves may include at least one pull tab. In one embodiment, the sleeves include at least one hinge section. In this embodiment of the invention, the hinge section of one sleeve may be coupled to the hinge section of the other sleeve. In another embodiment according to the invention, the system includes a spacer, such as a clamp, for joining two or more sleeves. The clamp may include a bulk material, a balloon or a pressure sensor.

In yet another embodiment, the envelope includes at least one positioning member for positioning the implant at the anatomical site in the body of the patient. In another embodiment, the envelope includes at least one attachment piece.

In one embodiment according to the invention, an antimicrobial drug, for example, an antibiotic, is disposed on the inner surface of the envelope. Alternatively, or in addition, an antimicrobial drug is disposed on the outer surface of the envelope. The envelope may be manufactured from absorbent materials and the drug may be absorbed through this absorbent material to both the inner and outer surfaces of the envelope.

In another embodiment according to the invention, the drug, such as an antibiotic, may be bonded to or may associate with the envelope material or with the one or more coatings applied to the inner or outer surface of the envelope. Alternatively, the one or more surface coatings may be absorbent and absorb the drug. The release and delivery of the drug from the envelope surface to the anatomical site of the patient's body will depend, in part, on the bonding affinity shared by the drug and the coating. When the bond is relatively weak, the drug will be released from the envelope more readily than when the bond is relatively strong.

In another aspect, the system according to the invention includes the envelope configured to enclose an implant, and a spacer disposed on at least one of said inner surface or outer surfaces of the envelope that is useful for positioning the implant at an anatomical site in the body of a patient. In one embodiment of the invention, the spacer includes a bulk material, such as a hydrogel, polyethylene, or cellulose. In another embodiment, the spacer includes a balloon that may be filled with a gas or liquid. In yet another embodiment, the spacer is a clamp including a first member and a second member. The thickness of, for example, the first member may provide the spacer thickness that is useful for positioning the implant. Alternatively, a balloon or a bulk material may be added to the exterior surface of the first member of the clamp to adjust the spacer thickness. In yet another embodiment, the system according to the invention includes a pressure sensor positioned, for example, at the spacer, for determining the amount of tension applied to the implant after the implant is positioned in the body. In addition, the pressure sensor may reveal the amount of tension applied to the envelope or alternatively the amount of tension applied to the implant.

In another aspect, the system according to the invention includes an envelope including two sleeves configured to enclose the implant, and a clamp for coupling together the two sleeves. The clamp includes a first member and a second member. In one embodiment of the invention, a portion of the sleeves overlaps and the clamp secures together the overlapping portions of the sleeves. The clamp may releasably couple the sleeves. In this embodiment, the sleeves may be the same or different lengths. In one embodiment the two or more sleeves are the same length.

In another aspect, the system according to the invention includes the envelope enclosing the implant, the envelope further includes at least one tab joined at a first or second end of the envelope for positioning the implant in the body. In one embodiment, the tab is a positioning member for positioning the implant in the body of the patient. The envelope may include two or more sleeves and a hinge. In another embodiment, the envelope having two or more sleeves and/or a hinge includes at least one attachment piece. In yet another embodiment, each sleeve may include a hinge section, the hinge sections of two sleeves may be coupled to one another.

In another aspect of the invention, an attachment piece is provided for joining an implant, such as a sling, to a delivery assembly. The attachment piece includes a first member bonded to the implant. The first member engageable with a second member wherein the first member is seated in the second member to join the implant to the delivery assembly. In another embodiment, the first member of the attachment piece includes an appendage to which the implant is bonded. The appendage and the first member may be manufactured from polyethylene and may be bonded to the implant by an adhesive, by suturing, or by heat bonding. In one embodiment, the appendage includes a free end that is bonded to the implant.

In another aspect of the invention, the system includes a delivery assembly for delivering an implant to an anatomical site in the body of a patient. In one embodiment, the delivery assembly includes a retractable point, a delivery handle including a proximal button, and a distal button. The proximal and distal buttons are operatively joined to the retractable point. Each of the proximal button and the distal button move the retractable point from a first position to a second position. In one embodiment of the invention, the delivery assembly further includes a cannula having a lumen. The cannula may include an arc. The retractable point of the delivery assembly may be positioned in the lumen of the cannula.

In yet another embodiment of this aspect of the invention, the delivery assembly may further include a dilator tube and an extender button positioned on the elongated body portion of the delivery handle. The extender button is operatively joined to the dilator tube and extends and retracts the dilator tube from the distal end of the elongated body portion of the delivery handle. The dilator tube includes a hollow member. In one embodiment, the hollow member further includes a rigid ring attached to the wall of the hollow member.

In another embodiment of the invention, the dilator tube includes a conical tip. The conical tip includes a hinge and the hinge may be a portion of the wall of the tube. In one embodiment according to the invention, the first member of the attachment piece is sized and shaped to fit within the lumen of the dilator tube. The first member includes a first and second portion enclosed by the dilator tube when the first member and dilator tube are anchored together. In one embodiment of the invention, the first member includes a first end having a slit. In one embodiment, when the first member is anchored in the dilator tube, the appendage is positioned between the conical tip and the tube. In another embodiment, the conical tip is sized and shaped to be seated on the first portion of the first member to anchor the first member to the dilator tube. In yet another embodiment, when the first member and the dilator tube are engaged, the first portion of the first member extends from the lumen of the dilator tube. The conical tip is positioned at the tissue piercing end of the delivery assembly and may also include an aperture. The aperture may provide an opening through which a cannula may emerge.

In another aspect, the invention relates to a method for positioning an implant at an anatomical site in the body of a patient. In this method, a system is provided that includes an implant and an envelope. The envelope is configured to enclose the implant and includes a drug disposed on at least one of an inner or an outer surface of the envelope. The system is inserted in the patient's body to an anatomical site to be treated. The drug is released from the envelope and delivered to the anatomical site in the patient's body. The implant is positioned at the anatomical site and the envelope is removed from the patient's body. After removal of the envelope, the implant remains where it was positioned at the anatomical site. In one embodiment of the method of the invention, the implant is positioned at the mid-urethra of the patient to treat, for example, female urinary incontinence. In a particular embodiment, the envelope has a visible indication mark on or at least visible from the envelope outer surface to assist the operator positioning the implant at the anatomical site in the body of the patient.

It is a further object of the method of the invention to provide an envelope enclosing an implant, such as a surgical mesh, to a damaged portion of a patient's body, wherein the envelope delivers drugs to the damaged area upon placement of the surgical mesh inside the patient's body. The surgical mesh may be, for example, a sling or other type of mesh that is shaped to fit the mid-urethra of a female patient.

In another aspect, the invention includes a method of positioning an implant at an anatomical site in the body of a patient. In one embodiment of the method, a system includes an envelope having at least two sleeves enclosing an implant, and a clamp that couples the sleeves together. The system is inserted into the patient's body and positioned at the anatomical site to be treated. Once the system enclosing the implant is positioned, the clamp is unfastened and removed from the patient's body followed by uncoupling and removal of the sleeves from the patient's body. The implant remains positioned at the anatomical site to be treated in the patient's body.

In another aspect, the invention is a method for positioning an implant at an anatomical site in the body of a patient. According to this method of the invention, a system is provided including an envelope having a lumen sized to enclose the implant and a tab disposed at each of a first end and a second end of the envelope. The operator inserts the system in the body of the patient, grasps the tabs disposed at each of the first and second ends of the envelope, positions the implant in the body, and removes the envelope from the body. In one embodiment the tab includes a positioning member for positioning the envelope enclosing an implant in the patient's body. The envelope may include a visual indication mark or a positioning mark for positioning the implant in the patient's body.

In another aspect, the invention is a method for delivering an implant to an anatomical site in the body of a patient. According to this method, the operator attaches the implant to the attachment piece, and the attachment piece is secured to the delivery assembly. In one embodiment where the attachment piece is pre-attached to the envelope, the operator attaches the pre-attached attachment piece and envelope onto the delivery assembly, to form the delivery system. In one embodiment, the delivery assembly includes a handle, a retractable point, a proximal button, and a distal button. Alternatively, the delivery assembly further includes a dilator tube and an extender button. The retractable point is extended by actuating or moving either the proximal or the distal button. In one embodiment, the implant attached to the delivery assembly provides the delivery system, and the delivery system is introduced into the body of the patient and positioned at the anatomical site. The implant is detached from the delivery assembly and the delivery assembly is withdrawn. In another embodiment, the delivery assembly is introduced into the body of the patient then the implant is attached to the delivery assembly and positioned at the anatomical site. Thereafter the implant is detached from the delivery assembly and the delivery assembly is withdrawn from the body of the patient. In another embodiment of the invention the method further includes grasping the tabs at the end of the envelope and tearing the envelope to remove it from the implant and then from the body.

The foregoing and other objects, aspects, features, and advantages of the invention will become more apparent from the following description and from the claims.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

FIG. 1B illustrates a top view of a longitudinal section of one embodiment of a system for implanting an implant in a body.

FIG. 1C illustrates a cross section at 1C-1C of the system for implanting an implant in a body, illustrated in FIG. 1A.

FIG. 2A illustrates a top view of a longitudinal section of another embodiment of the system for implanting an implant in a body where drugs are absorbed by a surface coating on the inside of an envelope.

FIG. 2B illustrates a cross section at 2B-2B of the system for implanting an implant in a body illustrated in FIG. 2A.

FIG. 3A illustrates another embodiment of the longitudinal section of the system illustrated in FIG. 2A including apertures to permit the inside surface of the envelope to contact a drug solution and a tear feature.

FIG. 3B illustrates a cross section at 3B-3B of the system for implanting an implant in a body illustrated in FIG. 3A.

FIG. 5A illustrates a side view of an embodiment of a system according to the invention including a clamp.

FIG. 5B illustrates a side view of one embodiment of a clamp according to the invention.

FIG. 5C illustrates a side view of another embodiment of a clamp according to the invention.

FIG. 5D illustrates a top view of an embodiment of a system according to the invention including a clamp illustrated in FIG. 5A.

FIG. 5E illustrates a side view of another embodiment of a system according to the invention for implanting an implant in a body including a bulk material disposed on the surface of the envelope.

FIG. 5F illustrates a side view of another embodiment of a system according to the invention for implanting an implant in a body including a balloon on the surface of the envelope.

FIG. 5G illustrates the system for implanting an implant in a body illustrated in FIG. 5F with the balloon filled.

FIG. 5H illustrates an embodiment of the clamp illustrated in FIG. 5A including a filled balloon.

FIG. 5I illustrates an embodiment of the clamp illustrated in FIG. 5A where the first member of the clamp includes a bulk material.

FIG. 8G illustrates a top view of a system for implanting an implant in a body illustrated in FIG. 8A.

FIG. 8H illustrates a side view of the system for implanting an implant in a body illustrated in FIG. 8A.

FIG. 8J illustrates another embodiment of the sleeve illustrated in FIG. 8D.

FIG. 8K illustrates another embodiment of the system for implanting an implant in a body illustrated in FIG. 8G.

FIG. 10B illustrates a sleeve for use in the system illustrated in FIG. 10A for implanting an implant in a body.

FIG. 10C illustrates a sleeve for use in the system illustrated in FIG. 10A for implanting an implant in a body.

FIG. 11A illustrates an embodiment of the attachment piece according to the invention.

FIG. 11B illustrates an embodiment of an implant secured to the attachment piece illustrated in FIG. 11A.

FIG. 11E illustrates a top plan view of the embodiment of FIG. 11C.

FIG. 11F illustrates a bottom plan view of the embodiment of FIG. 11C.

FIG. 11G illustrates a rear view of the embodiment of FIG. 11C.

FIG. 11H illustrates a front view of the embodiment of FIG. 11C.

FIG. 12A illustrates an embodiment of the dilator tube according to the invention.

FIG. 12B illustrates another embodiment of the dilator tube illustrated in FIG. 12A.

FIG. 19B illustrates a perspective view of an embodiment of a handle for delivering an implant to a body.

FIG. 19C illustrates a front view of the embodiment of FIG. 19B.

FIG. 19D illustrates a rear view of the embodiment of FIG. 19B.

FIG. 19E illustrates a side view of the embodiment of FIG. 19B.

FIG. 19F illustrates the opposing side view of the embodiment shown in FIG. 19E.

DESCRIPTION

Figure 1A:
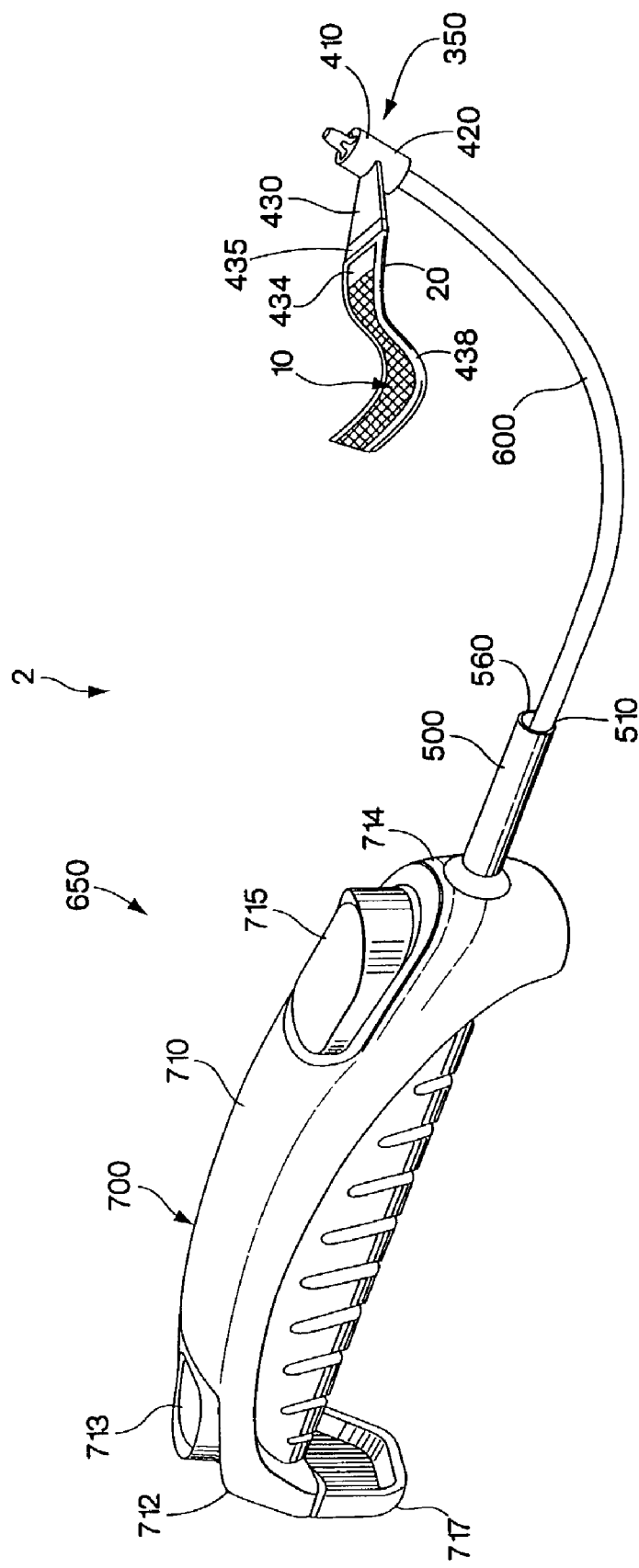
FIG. 1A illustrates a perspective view of a delivery system for implanting an implant in a body.

In general, the invention described herein is a system for implanting an implant into the body of a patient. Referring to FIG. 1A, in one aspect, the system includes an implant 10, an envelope 20 enclosing the implant, an attachment piece 350 for attaching the envelope 20 or implant 10 to a delivery assembly 650, and a delivery assembly 650 for delivering the implant 10 to an anatomical site in the body of a patient. In one embodiment, the delivery assembly 650 has a delivery handle 700, a dilator tube 500, and a cannula 600.

In one aspect, the invention relates to an envelope for enclosing the implant. The envelope includes a therapeutic drug, such as an antibiotic, on the outer surface, the inner surface, or both the outer and inner surface of the envelope.

In one embodiment of the invention illustrated in FIG. 1B, the system includes an implant 10, for example, a surgical mesh or a surgical sling, surrounded by or enclosed within an envelope 20. The envelope 20 may be likened to a pouch or a sleeve that surrounds the mesh 10.

Referring to FIG. 1C, in one embodiment, the envelope 20 has a lumen 185, and the envelope 20 is, for example, a tube that encloses the mesh 10. The envelope 20 has an inner surface 30 and an outer surface 40. Referring again to FIG. 1C, the width 24 of the envelope 20, as measured between the first side 203 and the second side 204 of envelope 20, may have a range from about 0.2 inches to 2.0 inches, preferably between about 0.5 inches and about 0.8 inches, and most preferably 0.6 inches. The longitudinal axis 22 of the envelope 20, measured from the first end 201 to the second end 202 of envelope 20, ranges from about 3.9 inches to about 27.6 inches, preferably between about 11.8 inches and about 23.6 inches, most preferably 19.7 inches. In one embodiment, the first and second ends 201 and 202 are opened. Alternatively, the first and second ends 201 and 202 may be closed by, for example, a heat sealed bond.

In one embodiment according to the invention, the implant is a surgical mesh 10. The surgical mesh 10 may be fabricated from one or more yarns and the yarns maybe made from one or more materials. Non-limiting materials that may be employed include polypropylene, polyesters, polyolefins, polytetrafluoroethylene, polyethylene, polyurethanes, nylons, and copolymers thereof as described in U.S. Pat. No. 6,042,592, the disclosure of which is incorporated by reference herein. The surgical mesh 10 may be a hybrid of synthetic materials and tissues; the implant 10 may be directed to slings described in, for example, U.S. Ser. No. 09/916,983, the entire disclosure of which is incorporated by reference herein. The surgical mesh 10 may also be made for absorbable materials, such as, polyglycolic acid, polylactic acid and other suitable absorbable materials.

The yarn may include a plurality of filaments, alternatively, a monofilament yarn may be employed. In one embodiment, the mesh is a polypropylene monofilament tricot mesh for use in surgical applications. Within a mesh 10, each yarn may have void areas between yarn filaments. The process used to fabricate the mesh 10 may create crevices in the mesh 10. Multifilament yarns have multiple voids or interstitial spaces between the yarn filaments. Mesh 10, according to the invention, may be produced according to a variety of fabrication processes known to the skilled artisan including, but not limited to, knitting, weaving, or braiding. Meshes fabricated using multifilament yarns may have both crevices and interstitial voids. In one embodiment according to the invention, the surgical mesh 10 is enclosed within the envelope 20 that surrounds the surgical mesh 10. The envelope 20 surrounding the mesh 10 reduces the likelihood that the mesh 10 will become contaminated with foreign matter such as bacteria during the procedure placing the mesh at an anatomical site in the body of the patient.

With continued reference to FIGS. 1B and 1C, in one embodiment according to the invention, the implant 10 is a sling, for example, the sling 10 described in U.S. patent application entitled "Medical Slings" by Gellman et al., attorney docket number (BSC-205), co-filed with the instant application, the entire disclosure of which is hereby incorporated by reference in its entirety.

The longitudinal axis 13 of the sling 10 may range from about 3.9 inches to about 24.0 inches, or between about 15.7 inches to about 19.7 inches, preferably about 17.7 inches. The width 14 of the sling 10 is between about 0.39 inches and about 1 inch, preferably about 0.43 inches. Referring still to FIG. 1C, the thickness 15 of the sling 10 ranges between about 0.0025 inch and about 0.1 inch, preferably between about 0.001 inch and 0.01 inch.

Referring still to FIGS. 1B and 1C, the thickness of the material used to make the envelope 20 may range from about 0.0001 inch to about 0.01 inch, preferably 0.0003 inch thick. As shown in FIG. 1C, the envelope has a first side 21 and a second side 23 opposite to first side 21. The distance between the first side 21 and the second side 23 of envelope 20 ranges between about 0.0027 inches to about 0.12 inches.

The envelope 20 may be used to assist in handling the sling 10 and/or to assist in adjusting the sling 10 during surgical placement. For example, the envelope 20 aides in preventing the sling 10 from stretching or becoming misshapen due to the sling 10's handling prior to placement of the sling 10 at the anatomical site within the body of the patient.

In one aspect, the invention provides a system for delivering the implant 10 having a drug delivery feature. The drug is delivered to the anatomical site in the patient's body and may be selected according to the physician's preference. Exemplary drugs are preferably soluble in water or other biologically inert solution, and include but are not limited to antimicrobials and antibiotics, such as neomycin and sulfa drugs, and anti-inflammatory agents such as steroidal or non-steroidal anti-inflammatory agents. The drug is released to the patient tissues upon contact with the tissues. Thus, the drugs that are delivered to the patient tissue surfaces when accessing and inserting the envelope 20 are active upon contact with the patient's tissue during implantation of the implant.

For example, referring again to FIGS. 1B and 1C, in one embodiment according to the invention, the drug delivery system includes the envelope 20 that is made from one or more absorbent material such as, for example, a sponge-like material. The envelope 20 may be pre-soaked in a solution containing a drug such as an antibiotic prior to surgical implantation of the implant 10 in a patient's body. Soaking the envelope 20 in a solution containing the drug just prior to surgery, coats the outer surface 40 of the envelope 20 with the drug. Pre-soaking the envelope in a solution of the drug is advantageous because the inside of the patient's body tissues are wiped with the drug-coated envelope 20 when the envelope 20 is inserted into the patient's body during surgical implantation of the implant 10. Alternatively, the drug in the drug solution in which the envelope is soaked, penetrates the absorbent material and coats the inner surface 30 of the absorbent envelope 20.

In another embodiment, according to the invention, the envelope 20 is made from a non-wettable material such as polypropylene, polyethylene, polyester, polytetrafluoroethylene, TYVEK®, MYLAR®, or co-polymers thereof. Polytetrafluoroethylene is suitable for use in accordance with the present invention is available from DuPont (Wilmington, Del., under the trade designation TEFLON®). These non-wettable materials do not uptake any liquids, for example, solutions of drugs. In order to permit drugs to bond or absorb to these non-wettable material surfaces, the inner surface 30 and/or the outer surface 40 of the envelope 20 is pretreated with a substance that is wettable such as, for example, a wettable coating composition. The wettable coating composition may be a synthetic coating such as, for example, polyvinylperilidone (PVP) or a natural coating such as, for example, collagen. The coating may be a physically absorbent material such as, for example, a cellulose sponge material. The wettable coating composition may be hydrophilic, which absorbs hydrophilic drugs. In one embodiment, the hydrophilic drug associates with the hydrophilic coating. Alternatively, a hydrophobic drug is disposed on an envelope 20, the envelope 20 including a hydrophobic coating. In some embodiments, a hydrophilic coating traps the hydrophobic drug on the surface of the envelope.

In another embodiment according to the invention, a hydrophobic coating may be applied to one or more surfaces of the envelope 20. Hydrophobic coatings may be used in conjunction with hydrophobic drugs. Where the association between the hydrophobic coating of the envelope 20 and the drug is weak, the drug will be readily released to the tissue surface contacted by the envelope 20. Alternatively, a stronger association between the coating and the drug, i.e., a stronger bonding affinity, may provide a slower release of the drug.

In a particular embodiment according to the invention, the coating applied to the surface of the envelope 20 may have an ionic charge. According to this embodiment of the invention, drugs having a complimentary charge will bond to the charged coating applied to the surface of envelope 20 when the coating and the drug are exposed to one another. The strength of bonding between the drug and the coating will influence how readily the drug is released from the surface of the envelope 20. Where the ionic bonding between the coating on the envelope 20 and the drug is weak, the drug will release more readily. Covalent bonding between the surface coating of the envelope 20 and the drug will diminish drug release.

In one embodiment according to the invention, shown, for example in FIG. 2B, the inner surface 30 of the envelope 20 has an inner surface coating 35 and the outer surface 40 of the envelope 20 has an outer surface coating 45. The inner surface coating 35 and the outer surface coating 45 may be selected from synthetic and natural coatings. The synthetic or natural coatings may be selected from the group consisting of a hydrophilic agent, a hydrophobic agent, and a physically absorbent material, for example, a cellulose sponge material.

In a particular embodiment of the invention, only one of the surfaces of the envelope 20 is coated, for example only the inner surface 30 of envelope 20 is coated. Alternatively, in another embodiment, the outer surface 40 of envelope 20 is coated. The envelope 20 with a coated surface may be dipped into a solution containing a drug, for example, a hydrophilic drug, just prior to surgery. The drug in solution bonds to the hydrophilic coating on envelope 20. In another embodiment, the hydrophilic coating and the hydrophilic drug are mixed to form a single coating. The hydrophilic coating may be disposed on the outer surface 40, the inner surface 30, or both the outer surface 40 and the inner surface 30 of the envelope 20. In one embodiment, the envelope contains a pre-loaded drug or drug and coating mixture. In yet another embodiment the envelope 20 is not coated, but when dipped into a drug solution just prior to the surgery the drug coats the surface of the envelope 20 and/or a sufficient amount of drug, for example, between about 0.5 ml to about 3 ml, is trapped within the envelope 20.

Referring again to FIGS. 2A and 2B, in one embodiment of the invention, the inner surface coating 35 of the envelope 20 may be hydrophobic. In another embodiment, the hydrophobic coating is mixed with a drug that is also hydrophobic. Thereafter the premixed hydrophobic coating and hydrophobic drug combination mixture is disposed on the inner surface 30 of the envelope 20. FIG. 2B is a cross section of the embodiment of the system including an implant 10 illustrated FIG. 2A. FIG. 2B illustrates that inner surface coating 35 is disposed on the inner surfaces 30 of the first side 21 and the second side 23 of envelope 20, in another embodiment a drug and coating combination may dispose thereon.

In an alternative embodiment (not shown), the outer surface 40 of the envelope 20 is coated with the hydrophobic coating and drug combination mixture.

Hydrophilic coatings may be water soluble and suitable water soluble hydrophilic coatings are available from Boston Scientific Corp., Natick, Mass., under the trade designations HydroPlus and HydroPass. Hyoscymine sulfate may be used in accordance with the invention that is available under the trade designation CYTOSPAZ from Polymedica (Woburn, Mass.). Ketrolac tromethamine is available under the trade designation Toradol from Roche Pharmaceuticals (Nutley, N.J.). Hydrophilic drugs that may be employed in accordance with the invention include oxybutynin chloride, lidocaine, ketorolac, and hyoscymine sulfate. Suitable hydrophobic drugs include ibuprofen, ketoprofen, and diclofenac. Hydrophobic coatings that may be employed in accordance with the invention include polytetrafluoroethylene, silicon, and Pyrelene.

In another embodiment according to the invention illustrated in FIGS. 3A and 3B, one or more apertures 50 are introduced into the envelope 20. The apertures 50 may be for example, cuts or slits. The apertures 50 extend through the envelope 20 and are disposed through at least the first side 21 of the envelope 20. In another embodiment, the apertures 50 are introduced on all sides of the envelope 20. The apertures 50 allow drug access to the inner surface 30 of envelope 20. For example, when the envelope 20 is soaked in a solution containing a drug, the drug enters the lumen 185 of the envelope 20 via the apertures 50 and associates with the inner surface coating 35.

Referring still to FIGS. 3A and 3B, in another embodiment according to the invention, the outer surface 40 and inner surface 30 of the envelope 20 are coated with an ionic coating composition. Alternatively, only one of the outer surface 40 or inner surface 30 of the envelope 20 is coated with the ionic coating composition. When the envelope 20 having apertures 50 is soaked in a solution containing a drug bearing a charge complementary to the charge of the ionic coating composition, both the outer surface coating 45 and the inner surface coating 35 bond with the drug. FIG. 3B shows that in one embodiment, the inner surface 30 of the first side 21 of the envelope 20 includes an inner surface coating 35 and the first side 21 outer surface 40 includes an outer surface coating 45. Similarly, FIG. 3B also shows that the second side 23 of the envelope 20 inner surface 30 includes an inner surface coating 35 and the second side 23 outer surface 40 includes an outer surface coating 45.

In one embodiment of the invention illustrated in FIGS. 3A and 3B, apertures 50 are present on at least the first side 21 of envelope 20. In this embodiment, a drug contacts the inner surface 30 of the envelope 20 when it flows through the apertures 50 into the lumen 185 of envelope 20. The drug associates with the inner surface coating 35. In a particular embodiment, the outer surface coating 45 bonds with the drug when, for example, the envelope 20 is submerged in a solution containing the drug.

The one or more apertures 50 disposed on the envelope 20 are, for example, slits disposed through the envelope 20. The apertures 50 are disposed in the envelope 20 to provide an opening on envelope 20 to permit drugs to enter the lumen 185 of envelope 20 and contact the inner surface 30 of the envelope 20. In one embodiment, the apertures 50 range in size from about 1/16 inch to about 1/4 inch in greatest dimension and permit fluid exchange in and out of the lumen 185 of the envelope 20. In one embodiment, the material used to manufacture the envelope 20 is porous, for example, polytetrafluoroethylene or polyethylene material and may be stretched so that the pores measure about 1 micron or greater.

In one embodiment, the one or more apertures 50 may be disposed so as to permit a solution to flow into the lumen 185 of the envelope 20 but not flow out, i.e., a one way channel. In another embodiment, the one or more apertures 50 disposed through the envelope 20 may be pores or slits. Such apertures 50 may range in size from about 1 micron to about 1/4 inch in largest dimension. A relatively large aperture 50, for example, between about 1/16 inch and about 1/4 inch in largest dimension enables the drug containing solution to readily enter into and contact the inner surface 30 of the envelope 20 when the envelope 20 is soaked in the solution containing the drug. Some of the solution also escapes from the envelope 20. In another embodiment, the one ore more apertures 50 are too small, i.e. about 5 microns, to permit the solution to escape from the envelope 20.

Shown in FIGS. 3A, and 3B, in another embodiment according to the invention the envelope 20 may also include a tear feature 60. The tear feature 60 assists the operator in opening the envelope 20 for placement of the mesh 10 enclosed by the envelope 20 inside the patient's body. The tear feature 60 may be a series of perforations through the envelope 20. The series of perforations through the envelope 20 weakens the portion of the envelope 20 where the tears are disposed such that the tear feature 60 permits the operator to open the envelope 20 by applying minimal force to the envelope 20. In a particular embodiment, the tear feature 60 is disposed about the entire perimeter of the envelope 20. Alternatively, the tear feature 60 may be disposed along only a portion of the perimeter of the envelope 20.

In yet another embodiment of the invention, the tear feature 60 perforations may double as the apertures 50 that permit the solution in which the envelope 20 is immersed to enter the lumen 185 of the envelope 20 and to contact the inner surface 30 of the envelope 20. For example, where the tear feature 60 is a series of apertures 50 through the envelope 20, the apertures 50 permit the drug solution to penetrate through the envelope 20 to the lumen 185 to contact the inner surface 30 of the envelope 20 when the envelope 20 is soaked in the drug solution.

Alternatively, the tear feature 60 includes a material that may be easily torn open. Such easily torn materials include, but are not limited to, for example, a material with a molecular orientation such as a linear low density polyethylene or linear polytetrafluoroethylene (e.g. TEFLON®). The entire envelope 20 may be manufactured from these materials. Alternatively, only one or more portions of the envelope 20 are manufactured from such "tearable" materials and/or construction methods, i.e., sections comprising linear low density polyethylene and/or a series of perforations or apertures 50 over a region of the envelope. In another embodiment, according to the invention, the tear feature 60 also includes an envelope 20 with tabs 188 and 198 that may be torn away, as described in detail below in accordance with, for example, FIGS. 8A-8K and 9A-9E. In yet another embodiment, the tear feature 60 is a strip of material disposed about the entire perimeter of the width 24 of envelope 20. The strip of material may be positioned, for example, against the inner surface 30 of the envelope. This strip of material protrudes from one or more areas of the envelope 20 where it may be accessed and torn away, unraveling at least a portion of the perimeter of envelope 20.

Figure 4A:
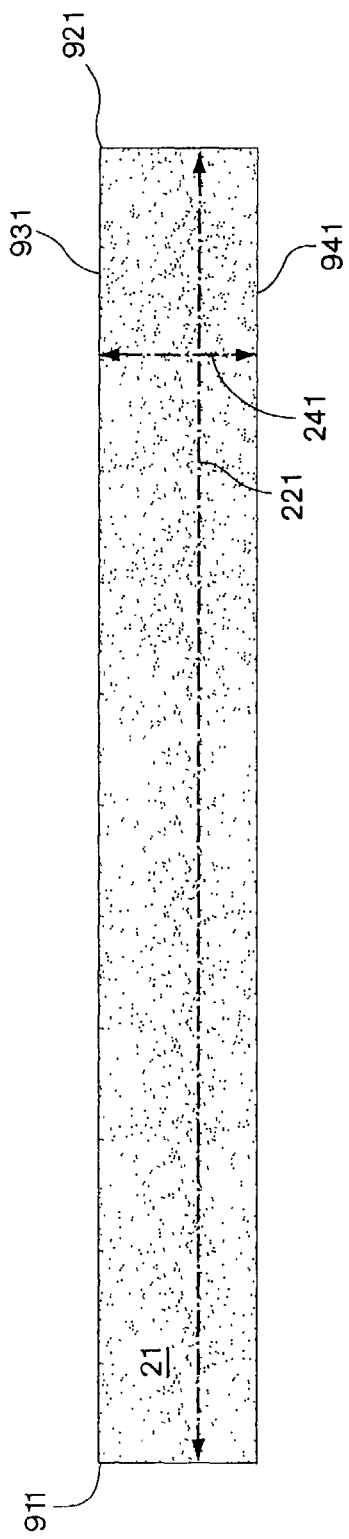
FIG. 4A illustrates a first side of a system for implanting an implant.
Figure 4B:
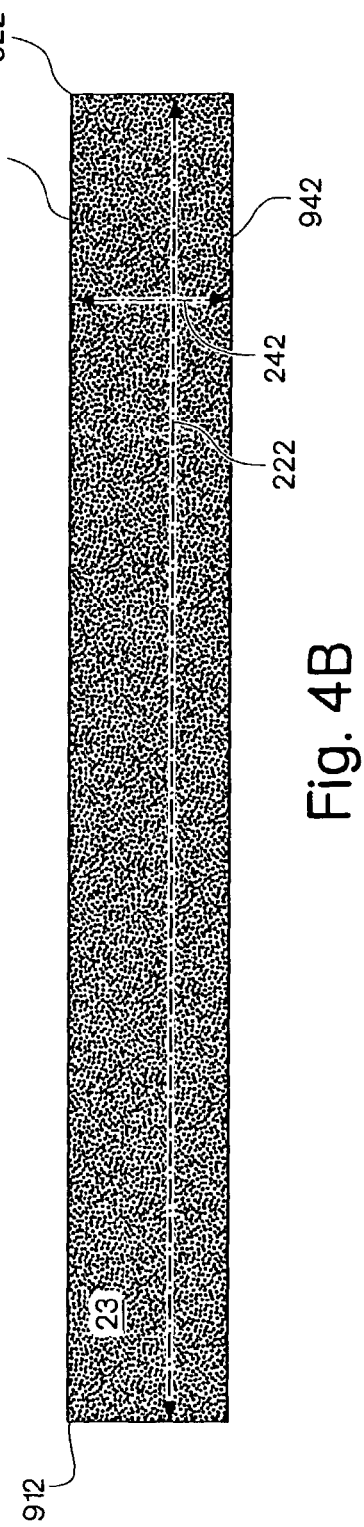
FIG. 4B illustrates a second side of a system for implanting an implant.
Figure 4C:
FIG. 4C illustrates the side view of a system for implanting an implant in a body including the first side illustrated in FIG. 4A and the second side illustrated in FIG. 4B.

In yet another embodiment of the invention, the envelope is a composite of two or more materials. Referring now to FIGS. 4A, 4B, and 4C, the first side 21 of envelope 20 includes a first material and the second side 23 of envelope 20 includes a second material that is different from the first material. FIG. 4C illustrates a side view of an envelope 20 wherein the first side 21 includes a first material and the second side 23 includes a second material and the sides, 21 and 23, are aligned and coupled at a seam 27 to form envelope 20.

In one embodiment, the first material of the first side 21 of envelope 20 is selected from the group of tearable materials, that includes, for example, polypropylene, nylon, a material with a molecular orientation such as a linear low-density polyethylene or other available flexible films. In another embodiment, the second material on the second side 23 of envelope 20 may be a material that does not tear, for example, polytetrafluoroethylene, TYVEK®, MYLAR® or other materials such as, for example, thermoplastics. According to the invention, the composite envelope 20 may be formed of two different materials that do not tear, for example, a first side 21 having TYVEK® and a second side 23 having MYLAR®. Alternatively, the composite envelope 20 may be formed of two materials that tear, such as a first side 21 of polyethylene and a second side 23 of polypropylene.

FIG. 4A illustrates a first side 21 and FIG. 4B illustrates a second side 23 of the envelope 20 illustrated in FIG. 4C. Referring again to FIG. 4A, width 241 of the first side 21 measured from the upper side 931 to the lower side 941, ranges from about 0.2 inches to about 2.0 inches, or between about 0.5 inches and about 0.8 inches and, preferably, 0.6 inches. The longitudinal axis 221 of the first side 21, measured from the first end 911 to the second end 921, as illustrated in FIG. 4A, ranges in length from about 3.9 inches to about 27.6 inches, or between about 11.8 inches and about 23.6, preferably 19.7 inches. Referring again to FIG. 4B, the width 242 of the second side 23, measured from the upper side 932 to the lower side 942, ranges from about 0.2 inches to about 2.0 inches, or between about 0.5 inches and about 0.8 inches, preferably, 0.6 inches. The longitudinal axis 222 of the second side 23, measured from the first end 912 to the second end 922, ranges from about 3.9 inches to about 27.6 inches, or between about 11.8 inches and about 23.6 inches preferably, 19.7 inches.

Referring again to FIGS. 4A, 4B and 4C, in one embodiment the first side 21 and the second side 23 of the envelope 20 may be cut to the same dimensions and the first side 21 may be placed on top of and aligned with the second side 23. When the first side 21 and the second side 23 are aligned, the first side 21 upper side 931 and the second side 23 upper side 932 are adjacent (not shown), the first side 21 lower side 941 and the second side 23 lower side 942 are adjacent, the first side 21 first end 911 and the second side 23 first end 912 are adjacent and the first side 21 second end 921 and the second side 23 second end 922 are adjacent. An envelope 20 may be formed by, for example, heat bonding around the perimeter of the aligned first side 21 and second side 23, to form seam 27 around the four sides of the aligned first side 21 and second side 23. Referring still to FIG. 4C, in another embodiment, to form a tubular envelope 20 a first seam (not shown) is formed between the first side 21 upper side 931 and the second side 23 upper side 932 and a second seam 27 is formed between the first side 21 lower side 941 and the second side 23 lower side 942, thereafter the interior of envelope 20 includes a lumen 185 with an open first end 201 and an open second end 202.

Alternatively, when the first side 21 is placed on top of the second side 23, the second side 23 that is adjacent to the first side 21 may include a melt liner. A melt liner is a layer or a portion of a layer that when added to the first side 21 and/or the second side 23 aids in forming the seam 27 between the first side 21 and the second side 23, when, for example, the sides 21 and 23 are exposed to a desirable temperature range. Suitable melt liners that may be employed include, for example, low density polyethylene, polyurethane, and polyester. In one embodiment, the second side 23 includes a material that cannot tear, for example, TYVEK®. In one embodiment, at least the side of the TYVEK® adjacent the first side 21 is coated with a melt liner, the melt liner enables the first side 21 and the second side 23 to heat seal to form seam 27 of envelope 20. In yet another embodiment of the envelope 20 shown in FIG. 4C, the first side 21 and the second side 23 are coupled with an adhesive to form seam 27. Suitable adhesives include, for example, urethane based and polyester based (i.e., elastomeric) adhesives. In one embodiment seam 27 forms the tearable region of the composite envelope 20. In another embodiment, illustrated in FIGS. 4D and 4E, the second side 23 is larger in dimension than the first side 21. In one embodiment, the dimensions of the second side 23 width 242 measures about 0.8 inches and the second side 23 longitudinal axis 222 measure about 27.6 inches. The dimensions of the first side 21 width 241 measures about 0.5 inches and the longitudinal axis 221 measures about 27 inches. The first side 21 has a top side 21a and a bottom side 21b (not shown) and the first side 21 is placed on top of the second side 23. In another embodiment, the first side 21 is placed in the center of the second side 23. The second side 23 has a top side 23a and a bottom side 23b.

Figure 4D:
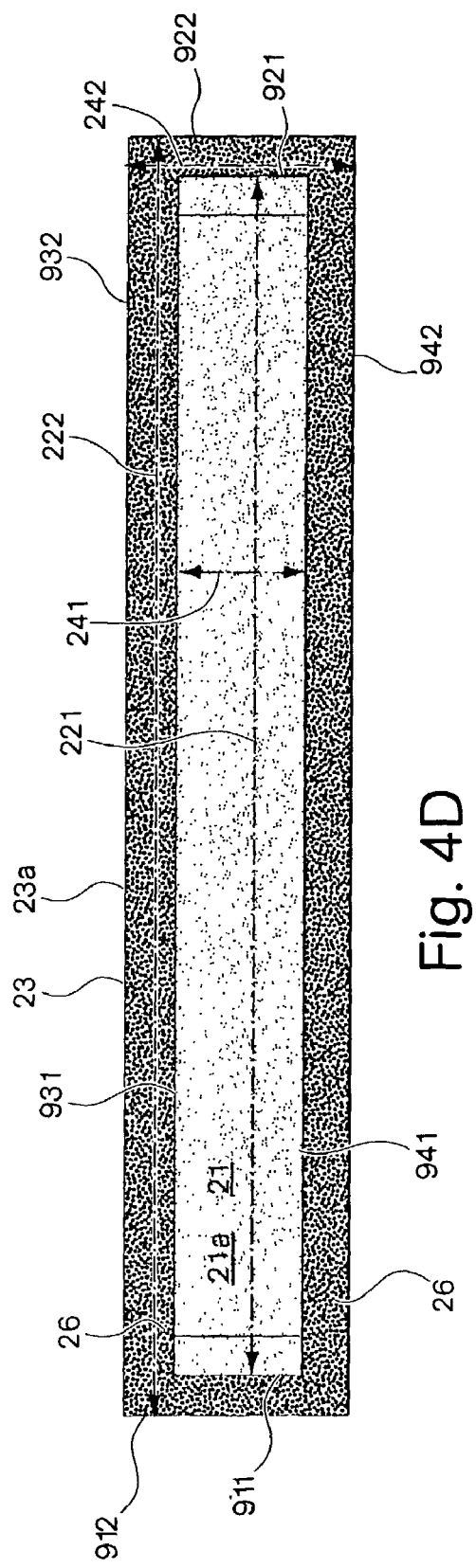
FIG. 4D illustrates a system for implanting an implant in a body including the first side illustrated in FIG. 4A and the second side illustrated in FIG. 4B.
Figure 4E:
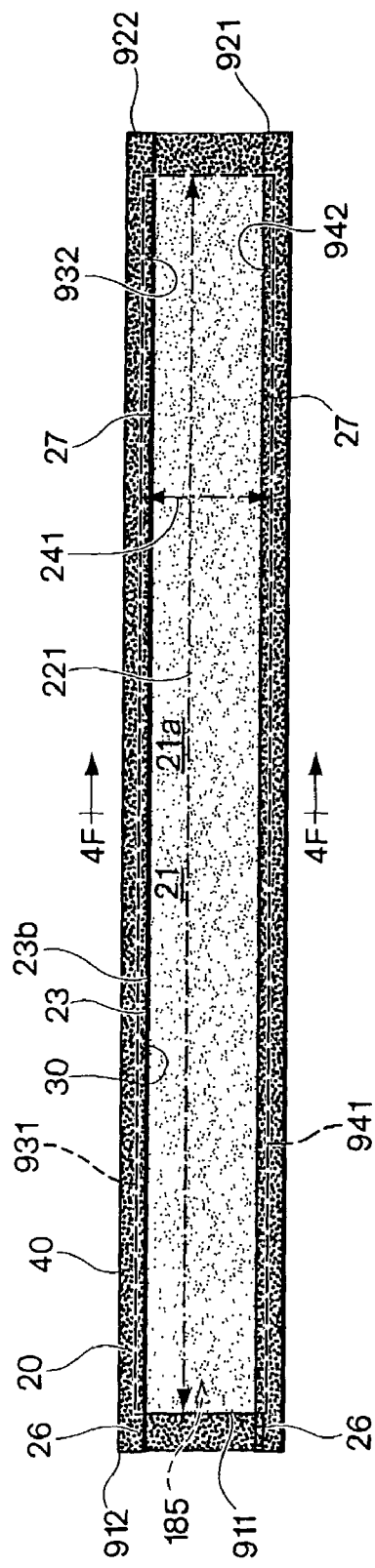
FIG. 4E illustrates another embodiment of a system for implanting an implant in a body including the first side illustrated in FIG. 4A and the second side illustrated in FIG. 4B.
Figure 4F:
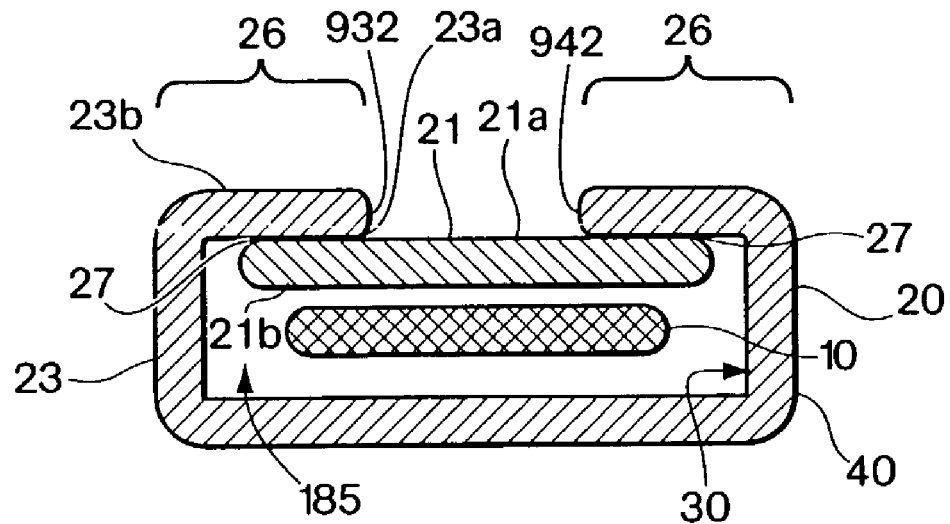
FIG. 4F illustrates a cross section at 4F-4F of the system for implanting an implant in a body illustrated in FIG. 4E.

FIGS. 4E and 4F shows that a portion of the excess material along the width 242 of the second side 23, shown in FIG. 4D, is folded to lie on the top side 21 a of the first side 21. The folded portion 26 of the upper side 932 of the second side 23 is coupled to the top side 21 a of the first side 21 to form a first seam 27, and the folded portion 26 of the lower side 942 of the second side 23 is also coupled to the top side 21a of the first side 21, to form a second seam 27. The folded portion 26 of the second side 23 folded on the top side 21a of the first side 21 includes adhesive, which couples the second side 23 top side 23a to the first side 21 top side 21a, to form an envelope 20 having a lumen 185. Alternatively, the second side 23 top side 23a, that is adjacent to the first side 21 top side 21a, contains a melt liner. When the portion of the second side 23 is folded over the first side 21 the melt liner joins the folded portions 26 of the second side 23 to the first side 21, by, for example, introducing heat to the folded portions 26 to bond the second side 23 to the first side 21 top side 21a, to form the seam 27. In yet another embodiment, the first material of the first side 21 and the second material of the second side 23 are coupled by heat bonding in the folded portions 26, to form a seam 27.

In a particular embodiment, referring again to FIGS. 4D and 4E, the first material of the first side 21 is tearable, i.e., a linear low density polyethylene, and the second material of the second side 23 is not tearable, for example, MYLAR®. Referring now to FIGS. 4E and 4F, the folded portion 26 of the second side 23 top side 23a is coupled to the first side 21 top side 21a at the upper side 932, to form a first seam 27, and at the lower side 942 of the second side 23, to form a second seam 27. Once the first and second seams 27 are formed, the first side 21 and the second side 23 form envelope 20, the envelope 20 having a lumen 185. When the first end 911 of the first side 21 of the lumen 185 is pulled toward the second end 921, the tearable material of the first side 21 coupled at about the upper side 932 and the lower side 942 of the second side 23 at folded portions 26, is torn at the seams 27 and separated from the second side 23. Thus, the tearable region may include the area of the envelope where a material that does not tear is coupled to a material that does tear.

Figure 4G:
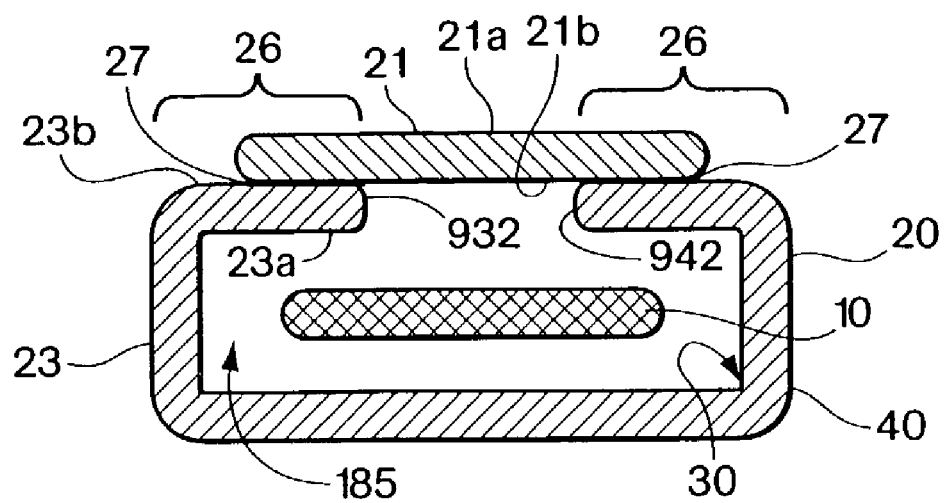
FIG. 4G illustrates a cross section of another embodiment of a system for implanting an implant in a body including the first side illustrated in FIG. 4A and the second side illustrated in FIG. 4B.

FIG. 4G illustrates an embodiment where the first side 21 bottom side 21b is coupled to the second side 23 bottom side 23b at about the folded portions 26 to form a first seam 27 and a second seam 27 of envelope 20. In an embodiment where the first material on the first side 21 is not tearable and the second material on the second side 23 is tearable, the second side 23 tears at the seams 27 when the first side 21 is separated from the second side 23.

In another aspect, referring now to FIGS. 5A-5E, the invention features an envelope 20 having a spacer 100, the envelope 20 enclosing the implant 10. The spacer 100 is a protrusion on at least one external surface of the envelope 20, having one or more pre-selected dimensions to aid in positioning the implant 10 at an anatomical site in the body of a patient. In one embodiment illustrated in FIG. 5A, the envelope 20 encloses an implant 10 such as a mid-urethral sling 10. The spacer 100 is used to adjust the placement of the sling 10 inside the patient's body. For example, where the sling 10 is employed to treat stress urinary incontinence by anchorless mid-urethral sling stabilization methods, the spacer 100 having pre-selected dimensions, is used to provide a reference distance between the envelope 20, which encloses the sling 10 and the patient's urethra 999. The operator is able to reference the relative distance between the envelope 20 surrounding the sling 10 and the patient's urethra 999 by the known pre-selected dimensions of the spacer 100. The operator may also adjust the sling 10 relative to the tension that is applied to the spacer 100. In one embodiment, an envelope 20 including a tear feature 60, such as described in relation to FIGS. 3A-3B, also has a spacer 100, the spacer may provide tension adjustment. The tear feature 60 simplifies removal of the envelope 20 after the sling 10 is positioned.

In one embodiment according to the invention, the spacer 100 illustrated in FIG. 5A is fastened around the perimeter of envelope 20. In one embodiment, illustrated in FIGS. 5B and 5C, the spacer 100 is a clamp 110 that may be fastened around the envelope 20. The clamp 110 spacer 100 may be releasably coupled to the envelope 20. The clamp 110 has a first member 120 and a second member 130. The first member 120 has a proximal end 120a and a distal end 120b, and at least a first exterior face 121 extending therebetween and a first thickness 105. The clamp 110 also has a first interior face 122. The second member 130 has a proximal end 130a and a distal end 130b, and at least a second exterior face 131 extending therebetween and a second thickness 106. In one embodiment, (not shown), the proximal end 120a of the first member 120 and the proximal end 130a of the second member 130 are engageable such as by coupling, and the distal end 120b of the first member 120 and the distal end 130b of the second member 130 are engageable by coupling.

In a particular embodiment, shown in FIGS. 5B and 5C, the clamp 110 further includes a hinge 140. Hinge 140 of clamp 110 joins the first member 120 and the second member 130 of clamp 110. The proximal end 120a of first member 120 and the proximal end 130a of second member 130 couple by coupling mechanisms such as a tongue and groove, peg and hole, or other mechanisms for coupling known to the skilled person. The clamp 110 is sized to encircle the envelope 20. The length of the first interior face 122 of the first member 120 of clamp 110 and the length of the second interior face 132 of the second member 130 of clamp 110 ranges from about 0.2 inches to 2.0 inches. The dimensions of interior face 122 of clamp 110 and interior face 132 of clamp 110, are selected in accordance with the dimensions of the envelope 20.

Referring now to FIG. 5D, the width 125 of the first member 120 and the width of the second member 130 of the clamp 110 (not shown) may range between about 0.2 inches and about 0.8 inches, preferably between about 0.4 inches and about 0.6 inches. The length 127 of the first member 120 of the clamp 110 may range from about 0.2 inches to 2.0 inches. Referring again to FIGS. 5B and 5C, the thickness 105 of the first member 120 of clamp 110 may range between about 0.007 inches and about 0.12 inches.

In one embodiment, referring still to FIGS. 5A and 5B, the spacer 100 includes the first member 120. The thickness 105 of the first member 120 of spacer 100 establishes the distance between the envelope 20 enclosing the sling 10 and the patients urethra 999 or the patients bladdemeck. Where the first member 120 is the spacer, the thickness 105 of spacer 100 may measure between about 0.007 inches and about 0.8 inches, preferably between about 0.2 inches to about 0.6 inches. In an embodiment where the spacer 100 is placed adjacent the patients urethra 999, the length of the first member 120, measured by the distance between the proximal 120a and distal ends 120b of the first member 120, may be sized to complement the length of the patients urethra 999, generally between about 0.2 inches and 1.2 inches.

As shown in the embodiment illustrated in FIG. 5E, the spacer 100 may include a bulk material 112 disposed on the first side 21 of the envelope 20. The bulk material 112 may be, for example, polyethylene or a hydrogel, such as, sodium carboxymethylcellulose, phosphate buffered saline (PBS), or combinations thereof. In one embodiment, the bulk material 112 may be disposed on the entire surface of the first side 21 of envelope 20.

Alternatively, as shown in FIG. 5E, the bulk material 112 may be disposed on only a portion of the first side 21 of envelope 20. For example, in one embodiment, the bulk material 112 is disposed at the midpoint between the first end 201 and the second end 202 of the longitudinal axis of the first side 21 of envelope 20. The bulk material 112 may be disposed between about 0.1 inches to about 0.4 inches, preferably between about 0.2 inches to about 0.3 inches to each side of the midpoint of the longitudinal axis. With continued reference to FIG. 5E, the bulk material 112 of the spacer 100 may be disposed across the width 24 of the first side 21 of the envelope 20, i.e., between the top side 203 and the bottom side 204 of the envelope 20. Referring again to FIG. 5A, when the envelope 20 enclosing the sling 10 is employed to treat stress urinary incontinence by anchorless mid-urethral sling stabilization methods, the width 24 of the envelope 20 is adjacent the urethra 999 or the bladderneck. A spacer 100 provides a reference distance between the envelope 20 and the patient's urethra 999 or the patient's bladderneck. The bulk material 112 should be disposed about between about 0.2 inches to about 1.2 inches along the width 24 of envelope 20, because the spacer 100 should be equal to or smaller than the length of the female urethra, and generally, the maximum length of the female urethra is 1.2 inches. The thickness 103 of the bulk material 112 disposed on the first side 21 may range from about 0.007 inches to about 0.8 inches, preferably between about 0.2 inches to about 0.6 inches.

In yet another embodiment, illustrated in FIGS. 5F-5G, the spacer 100 includes a balloon 111. In one embodiment, the balloon 111 is part of and integral with the envelope 20. In another embodiment, the spacer 100, balloon 111, is joined to the envelope, for example, by adhesives.

In one embodiment, the balloon 111 is positioned on the inner surface 30 of the first side 21 of envelope 20. In another embodiment, the balloon 111 is positioned on the outer surface 40 of the first side of envelope 20. The balloon 111 may be disposed along the entire length of the first side 21 of envelope 20. Alternatively, as shown in FIGS. 5F-5G, the balloon 111 may be disposed on only a portion of the first side 21 of envelope 20. For example, in one embodiment, the longitudinal axis 107 of balloon 111 is between about 1.2 inches to about 4.0 inches about the midpoint of the longitudinal axis 22 of the envelope 20. The width 104 of the balloon 111 measures between about 0.4 inches to about 1.2 inches. In a particular embodiment, the longitudinal axis 107 of balloon 111 is between about 0.2 inches to about 0.8 inches, preferably between about 0.4 inches and 0.6 inches, about the midpoint of the longitudinal axis 22 of the envelope 20, and the width 104 of the balloon 111 is between about 0.4 inches to about 1.2 inches. In one embodiment, the width 104 of balloon 111 is equal to or smaller than the length of the female urethra, generally equal to or less than 1.2 inches. In another embodiment, the width 104 of the balloon 111 is the same as the width 24 of the envelope 20.

The balloon 111 may be made from the same materials as the envelope 20. These materials include, but are not limited to, for example, an absorbent material, such as a sponge-like material, or polypropylene, polyethylene, polyester, polytetrafluoroethylene or copolymers thereof. Alternatively, the balloon 111 may be made of a different material than the material used to make the envelope 20. The balloon 111 may be placed on the envelope 20 according to methods known to the skilled person, for example, by gluing, sewing, tying, or melting onto a surface of envelope 20. In one embodiment, the balloon 111 is filled with a fluid or a gas and then joined to the exterior surface 40 of the first side 21 of the envelope 20. Alternatively, the balloon 111 may be filled with a gas or liquid after the balloon 111 is joined to the envelope 20. In yet another embodiment, the balloon 111 is integral with, i.e., fabricated in the envelope 20 when the envelope 20 is fabricated.

The balloon 111 may be filled with a gas or a fluid, for example, water, sterilized water, saline, or a bulk material such as, for example, polyethylene or a hydrogel, such as, sodium carboxymethylcellulose, PBS phosphate buffered saline, or combinations thereof. In another embodiment, the balloon 111 may be filled to a thickness 103 between about 0.08 inches to about 0.8 inches, preferably about 0.2 inches to about 0.6 inches. The extent of inflation of the balloon 111 may vary according to operator preference, the size of the patient, the anatomical location where the balloon is positioned, or other factors. In one embodiment, the balloon 111 is filled by the operator prior to commencing the surgical procedure. Alternatively, the balloon 111 is filled after the envelope 20 enclosing the implant 10 is introduced into the anatomical site of the patient's body.

In one embodiment, according to the invention, the balloon 111 may be filled by inserting a needle coupled to a syringe into the balloon 111 and injecting the contents of the syringe, e.g., air, water, sterilized water, saline, bulk material, or a combination thereof, into the balloon 111. Alternatively, the balloon 111 may include a valve and the balloon is subsequently filled by injecting the contents of the syringe into the balloon 111. In one embodiment, the balloon 111 is pre-filled and pre-attached to envelope 20.

In another embodiment, shown in FIGS. 5H and 5I, the clamp 110 includes a balloon 111 or a bulk material 112. For example, shown in FIG. 5H, the first exterior face 121 of the first member 120 includes a balloon 111. In this embodiment, the thickness of spacer 100 includes a combination of the thickness 105 of the first member 120 and the thickness 103 of the balloon, bulk material, or other spacer device. The thickness of the spacer 100 includes the first member 120 thickness 105 and the balloon 111 thickness 103 or the first member 120 thickness 105 and the bulk material 112 thickness 103, respectively, as shown in FIGS. 5H and 5I. The spacer 100 thickness measures between about 0.007 inches to about 0.8 inches, preferably between 0.08 inches and 0.7 inches, preferably between about 0.2 inches to about 0.6 inches.

Referring to FIG. 5H, the balloon 111 may be disposed on the first exterior face 121 of the first member. Similarly, as shown in FIG. 5I the bulk material 112 may be disposed on the first exterior face 121 of the first member 120. In one embodiment, the balloon or bulk material entirely covers the first member 120 first exterior face 121. Referring again to FIG. 5A, where the spacer 100 is employed in mid-urethral sling procedures, the spacer 100 is positioned adjacent to the urethra 999 or bladderneck. The urethra length is generally up to 3 cm, about 1.2 inches. Thus, where the balloon or the bulk material together with the first member 120 of the clamp 110 form the spacer 100, the length of the spacer 100 will be sized accordingly. Referring again to FIG. 5D, the balloon or the bulk material are positioned to cover between about 0.2 inches and about 1.2 inches of the length 127 of the first member 120 to form spacer 100. In one embodiment, the balloon 111 and the bulk material 112 are positioned to cover between about 0.2 inch and about 0.8 inch of the width 125 of first member 120. In a particular embodiment, the balloon 111 or the bulk material 112 covers the width 125 of the first member 120.

In another embodiment, the clamp 110 includes a pressure sensitive mechanism, i.e., a pressure sensor 101. In one embodiment, illustrated in FIG. 5B, the clamp 110 includes the pressure sensor 101 on the exterior face 121 of the first member 120. In another embodiment, as shown in FIG. 5H, the first exterior face 121 of the first member 120 includes the spacer 100, such as, a balloon 111, and the pressure sensor 101. The pressure sensor 101 indicates the pressure applied to the spacer 100. Alternatively, the spacer 100 disposed on envelope 20 as shown in FIG. 5G includes the pressure sensor 101.

Referring again to FIGS. 5A and 5B, the pressure sensor 101 is employed during the surgical procedure to measure and/or indicate the pressure applied to the urethra 999 or bladderneck by the spacer 100. The spacer 100 is adjacent (i.e., disposed on or joined to) the envelope 20 enclosing the implant 10. When implanting the envelope 20 enclosing the sling 10, tension is applied to the envelope 20 to adjust the distance between the urethra 999 or bladderneck and the sling 10. A target pressure range may be set in the pressure indicator or pressure gauge. The pressure sensor 101 may be, for example, a tube that is connected at one end of the tube to the spacer 100 and at the other end of the tube to a pressure indicator. When the appropriate level of tension is applied to the spacer 100, the pressure sensor 101 indicates that the targeted pressure range is achieved. The pressure sensor 101 may indicate that this pressure is achieved by various indicator means, such as, for example, sound, digital readout, mechanical indicators, and fluid displacement (i.e., a manometer). When the pressure sensor 101 indicates the pressure range has been met and the envelope 20 placement is properly adjusted, then the spacer 100 and the envelope 20 are removed leaving the sling 10 correctly positioned and at the appropriate tension at the anatomical site in the patient's body. In another embodiment, after the spacer 100 and envelope 20 are removed, a gap created by the spacer 100 is left between the sling 10 and the urethra 999 and there is no load present between the sling 10 and the urethra 999. In an embodiment where the spacer 100 is a clamp 110 fastened around the perimmeter of envelope 20, the clamp 110 is released from envelope 20 prior to removing the envelope 20 from the anatomical site in the patient's body.

In another embodiment according to the invention the envelope 20 and/or the clamp 110 are tinted. In one embodiment, only a portion of the envelope 20 is tinted, for example, about the longitudinal axis 22 of envelope 20. The envelope 20 and the clamp 110 may be the same color or alternatively, they may be tinted differently. In yet another embodiment, a pattern or design is applied to on the envelope 20 and/or the clamp 110. In a preferred embodiment, the envelope 20 is tinted blue which is visible under the light from a cytoscope that is used when implanting the sling 10 into the body of the patient. In another embodiment, the envelope 20 is tinted black. In yet another embodiment, a spacer, a clamp, a tinted area or other indication mark provides a visual indication of the placement of the sling 10. The visual indication may be employed to inform the operator about the orientation of the sling 10, for example, whether the sling 10 is facing up, facing down or is twisted. In one preferred embodiment, the visual indication mark is on the center of the envelope 20 enclosing the sling 10. In one preferred procedure, with continued reference to FIG. 5A, a visual indication of clamp 110 is aligned with the urethra 999.

Figure 6:
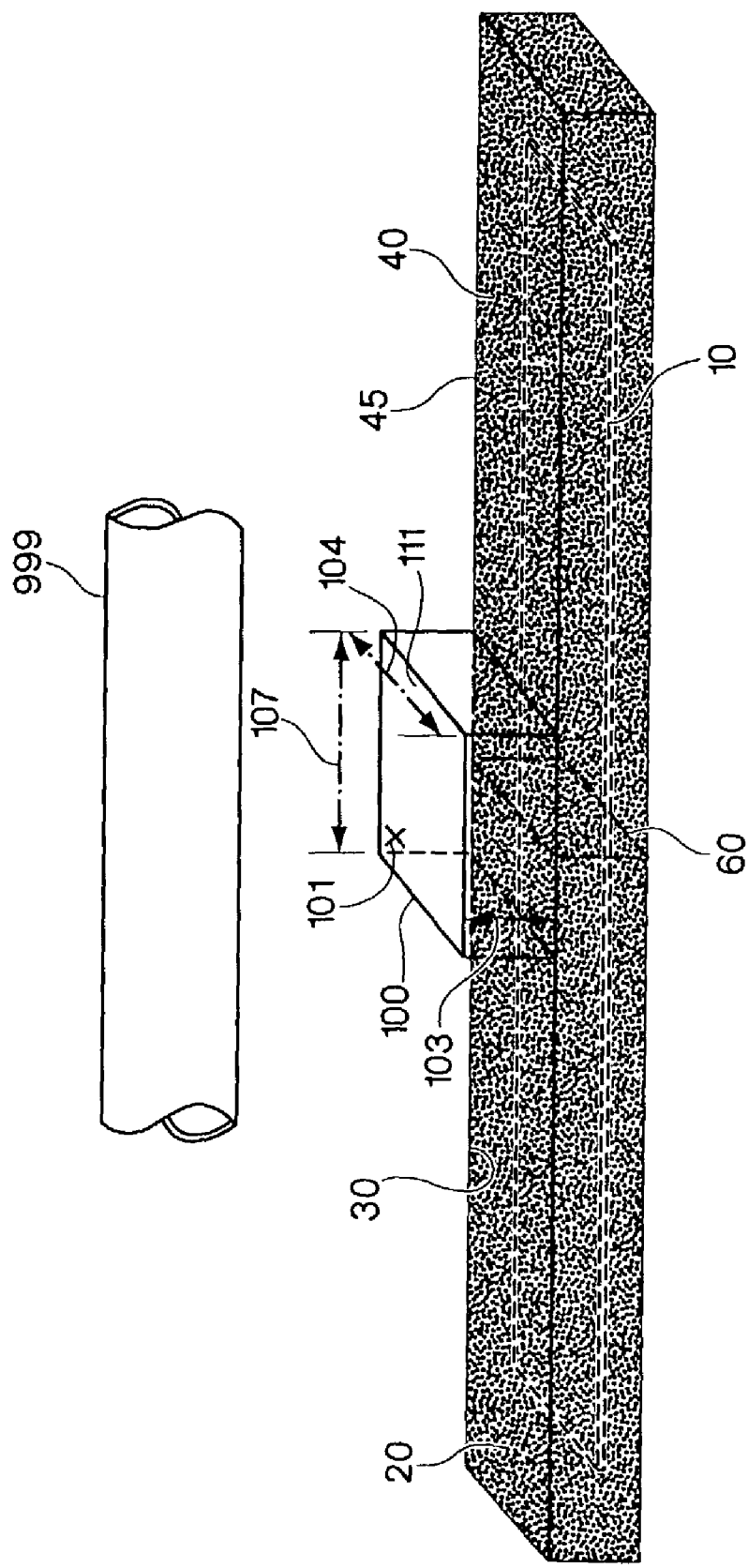
FIG. 6 illustrates an embodiment of the system illustrated in FIGS. 5F-5G for implanting an implant in a body.

In yet another embodiment, as shown, for example, in FIG. 6, the envelope including a balloon 111 includes an outer surface coating 45 on the outer surface 40 of the envelope 20. A therapeutic drug may be associated such as, for example, bonded with the outer surface coating 45. The envelope 20 with the spacer 100 may further include one or more drugs and/or one or more coatings as described above (see FIGS. 1A, 1B, 2A, 2B, 3A, and 3B and corresponding text).

Figure 7A:
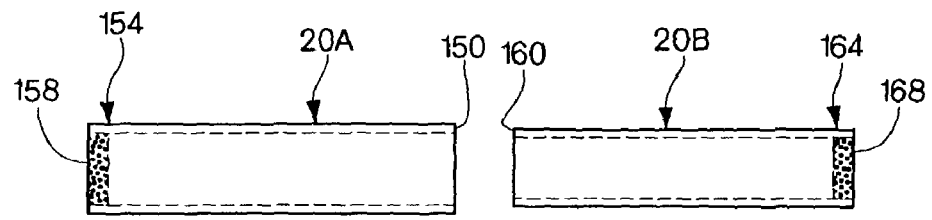
FIG. 7A illustrates another embodiment of the system for implanting an implant in a body.

In another aspect, the invention is a system for delivering an implant enclosed in an envelope. In one embodiment, according to the invention, the envelope 20 has two or more sleeves 20A, 20B that are positioned such that one end of the first sleeve 20A overlaps an adjacent end of the second sleeve 20B. The two sleeves 20A, 20B enclose the implant 10. For example, referring to FIG. 7A, first sleeve 20A has a proximal end 154 including a tab 158 and a distal end 150. In one embodiment, the tab 158 seals the proximal end 154 of the first sleeve 20A. In another embodiment, the tab 158 is a positioning member for positioning the envelope 20 at the anatomical site in the body of the patient. Referring still to FIG. 7A, the distal end 150 of first sleeve 20A is adjacent to the proximal end 160 of second sleeve 20B. The distal end 164 of second sleeve 20B includes a tab 168. In one embodiment, tab 168 seals the distal end 164 of second sleeve 20B. In another embodiment, the tab 168 is a positioning member for positioning the envelope 20 at the anatomical site in the body of the patient.

Figure 7B:
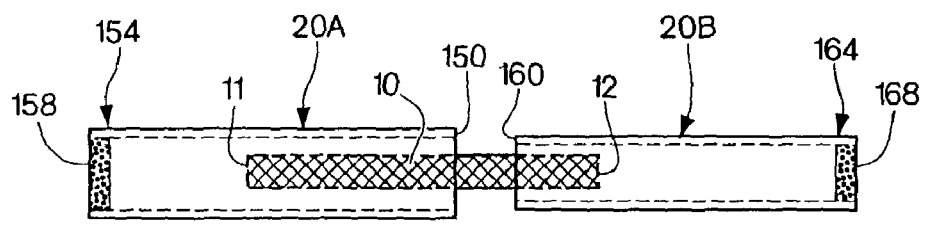
FIG. 7B illustrates the system shown in FIG. 7A including a surgical mesh.

The length of first sleeve 20A, measured from the distal end 150 to the proximal end 154, may range from about 2.0 inches to about 15.4 inches, preferably 11.0 inches. The length of second sleeve 20B, measured from the proximal end 160 to the distal end 164, may range from about 2.0 inches to about 15.4 inches, preferably 11.0 inches. In one embodiment, the first and second sleeves 20A and 20B, are of equal length from their distal end to proximal end. FIG. 7B shows an implant 10, for example, a mid-urethral sling, a portion of which is placed into the distal end 150 of first sleeve 20A and a portion of which is placed into the proximal end 160 of second sleeve 20B. The length of the sling 10, i.e., the distance from the proximal end 11 to the distal end 12 of the sling 10, may range from about 4.0 inches to about 24.0 inches, or between about 16.0 inches to about 20.0 inches, preferably about 18.0 inches.

Figure 7C:
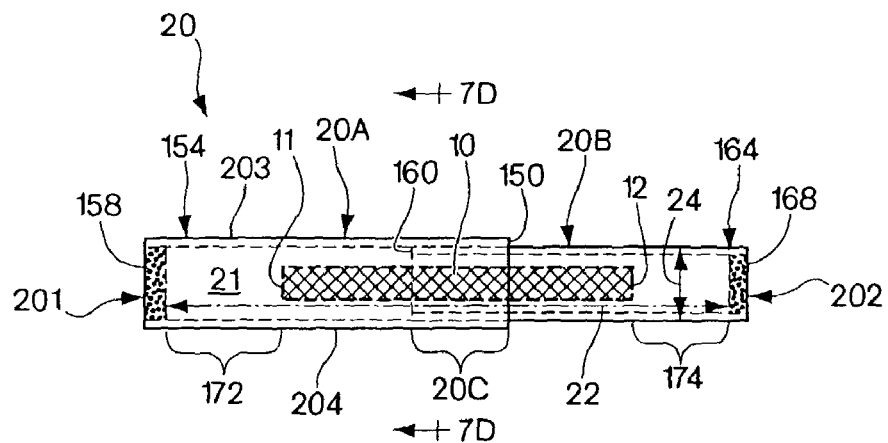
FIG. 7C illustrates the system shown in FIG. 7B.
Figure 7D:
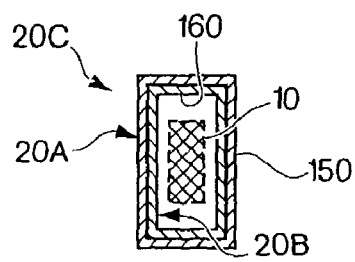
FIG. 7D illustrates a cross-section at 7D-7D of the embodiment of the system illustrated in FIG. 7C.

FIG. 7C shows one embodiment of the envelope 20 including first sleeve 20A and second sleeve 20B enclosing the implant 10. As shown in 7C, the proximal end 160 of sleeve 20B is inserted into the distal end 150 of sleeve 20A to form an overlap region 20C of the first and second sleeves 20A, 20B. The overlap region 20C of first sleeve 20A and second sleeve 20B may range in length from about 0.4 inches to about 3.2 inches, preferably between 0.8 inches and 1.6 inches. FIG. 7D illustrates one embodiment of a cross section of region 20C of the envelope 20 where the proximal end 160 of second sleeve 20B is enclosed by the distal end 150 of first sleeve 20A. Referring again to FIG. 7C, the length of the overlap region 20C, the length of the sling 10, and the length of first sleeve 20A and second sleeve 20B are selected to provide a section 172 of the sleeve 20A, from the proximal end 11 of the sling 10 to the proximal end of the 154 of sleeve 20A, that is at least 1 inch in length. Similarly, the section 174 of the sleeve 20B, from the distal end 12 of sling 10 to the distal end 164 of sleeve 20B, is at least 1 inch in length. The sections 172 and 174 are grasped by the operator and assist in removal of the envelope 20 from the patient's body without disturbing the position of the implant of sling 10, as described below.

The longitudinal axis 22 of the envelope 20, measured between the first side 201 and the second side 202, ranges from about 3.6 inches to about 30.4 inches, or between about 11.8 inches and about 23.6 inches in length, preferably 19.7 inches. The width 24 of the envelope 20 measured between the top side 203 and the bottom side 204 of envelope 20 may range from about 0.2 inches to about 2.0 inches, or between about 0.5 inches and about 0.8 inches, preferably 0.6 inches.

Figure 7F:
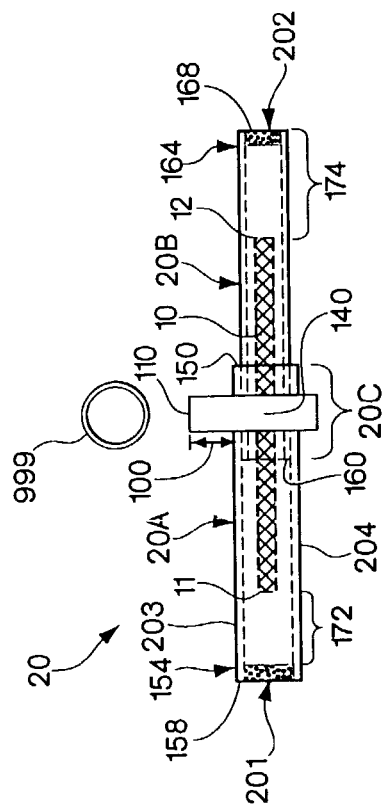
FIG. 7F is a side view of another embodiment of the system for implanting an implant in a body.
Figure 7E:
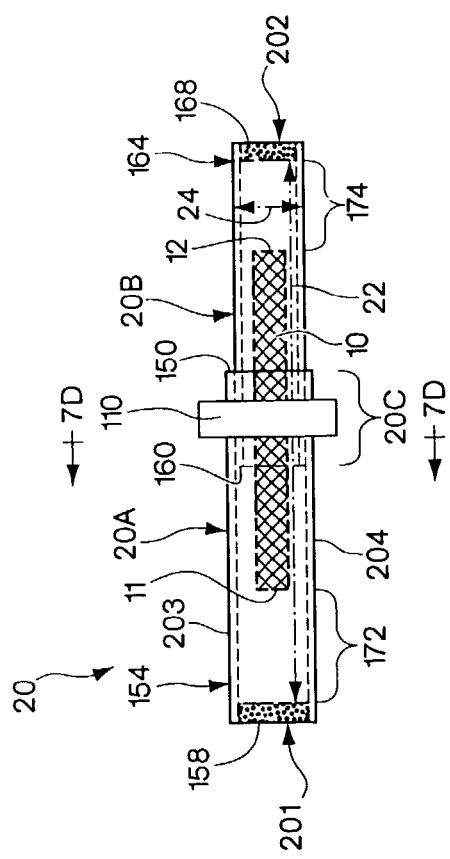
FIG. 7E illustrates another embodiment of the system illustrated in FIG. 7C for implanting an implant in a body.
Figure 7G:
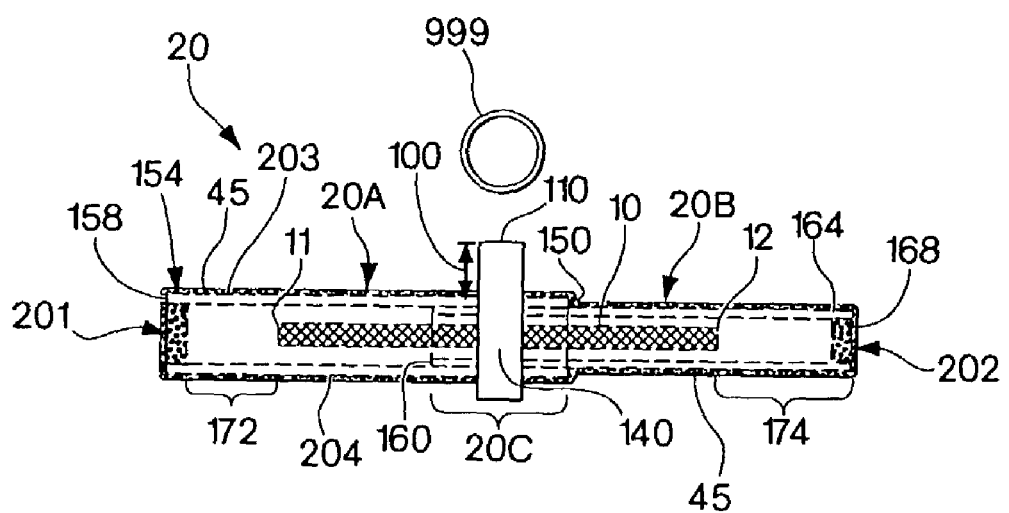
FIG. 7G illustrates another embodiment of the system illustrated in FIG. 7F for implanting an implant in a body.

In another embodiment according to the invention illustrated in FIGS. 7E, 7F, and 7G, the clamp 110 is used to fasten the sleeves 20A and 20B in the overlap region 20C such that the sleeves 20A and 20B are secured in place and the implant 10 remains inside the envelope 20. In this embodiment, the clamp 110 is positioned and secured about the perimeter of the overlap region 20C of envelope 20. As shown in FIGS. 7E and 7F, the first member 120 and the second member 130 of clamp 110 are closely aligned and positioned to provide enough compressive force to secure the region 20C and prevent separation of first sleeve 20A and second sleeve 20B during a procedure in which the envelope 20 is positioned at the anatomical site in the patient's body. In one embodiment, the clamp 110 or other fastener releasably couples sleeves 20A and 20B and after the envelope 20 including clamp 110 is positioned in the patient's body, the clamp 110 is unfastened and removed. Thereafter sleeves 20A and 20B are removed and sling 10 remains positioned at the anatomical site in the patient's body. Alternative fasteners, not shown, may be employed to secure the implant inside the sleeves of the envelope such as, for example, hemostats, needle graspers, and spring loaded clamps.

FIG. 7F shows a sideview of the envelope 20 illustrated in FIG. 7E. The envelope 20 includes two sleeves 20A and 20B and a clamp 110. The clamp 110 is employed to couple the sleeves 20A and 20B, enclosing the implant 10. As shown in FIG. 7F, the proximal end 160 of sleeve 20B inside the distal end 150 of sleeve 20A forms overlap region 20C. The clamp 110 is placed around the perimeter of the overlap region 20C. In this view, a hinge 140 of clamp 110 is visible from the side view of the envelope 20.

In another aspect, the invention includes a method for positioning the sling 10 at an anatomical site in a patient's body, for example, positioning a mid-urethral sling for the treatment of female urinary incontinence. In one embodiment of the method according to the invention, the clamp 110 is placed at about the mid point of the sling 10, for example, as illustrated in FIGS. 7E and 7F. The physician may use the clamp 110 to indicate placement of the envelope enclosing the sling 10. During placement of the sling 10, the clamp 110 is positioned directly under the patient's urethra 999. The clamp 110 may further include the spacer 100. As described above, in relation to, for example, FIGS. 5H and 5I, the spacer 100 may include the thickness 105 of the first member 120 of clamp 110, alternatively or in addition, the thickness of the spacer 100 on the clamp 110 may include the thickness 103 of a balloon 111 or the thickness 103 of the bulk material 112. The operator may use the spacer 100 to adjust the tension of the sling 10 during its placement. In another embodiment, the clamp 110 further includes a pressure sensor, for example, the pressure sensors 101 described above in conjunction with FIGS. 5B, 5F, 5G and 5H. The pressure sensor 101 is used by the operator to aid in positioning the sling 10 and applying the proper tension to the sling 10.

In one embodiment of the method according to the invention, the operator positions the envelope 20, shown in FIGS. 7E and 7F, including first sleeve 20A, and second sleeve 20B, the sling 10, and the clamp 110, at the anatomical site in the body of the patient. In one embodiment according to the invention, when the operator is satisfied with the position and/or tension of the sling 10, clamp 110 may be uncoupled, released from the envelope 20, and removed from the body of the patient. Thereafter, the operator may remove second sleeve 20B and first sleeve 20A from the body of the patient by grasping and pulling sleeve sections 174 and 172, respectively. The removal of the clamp 110 and sleeves 20A and 20B are completed with care to maintain the sling 10 placement and tension and to avoid stretching the sling 10 material. Thus, according to a particular embodiment of the invention, the removal of first sleeve 20A and second sleeve 20B causes no change in sling 10 position. Thus, the placement and/or tension of the sling 10 remains the same as the placement and tension of the sling 10 when the operator placed the sling 10 at the anatomical site in the body, prior to removal of first sleeve 20A and second sleeve 20B.

In yet another embodiment according to the invention, the envelope 20 including first sleeve 20A, second sleeve 20B, the sling 10, and the clamp 110, shown in FIG. 7G also includes an outer surface coating 45 disposed on the outer surface of envelope 20. The envelope 20 including sleeves 20A, 20B and the clamp 110, may further include one or more drugs and/or one or more coatings as described above (see FIGS. 1A, 1B, 2A, 2B, 3A, and 3B and corresponding text).

In another aspect, the invention includes a system for delivering an envelope and an implant. In one embodiment, shown in FIG. 8A, the system includes the envelope 20 including two or more sleeves 20A, 20B and one or more tabs 188, 198, 208, 218. The tabs 188, 198, 208, and 218 simplify placement and/or removal of the envelope 20 from inside the body of the patient.

Figure 8A:
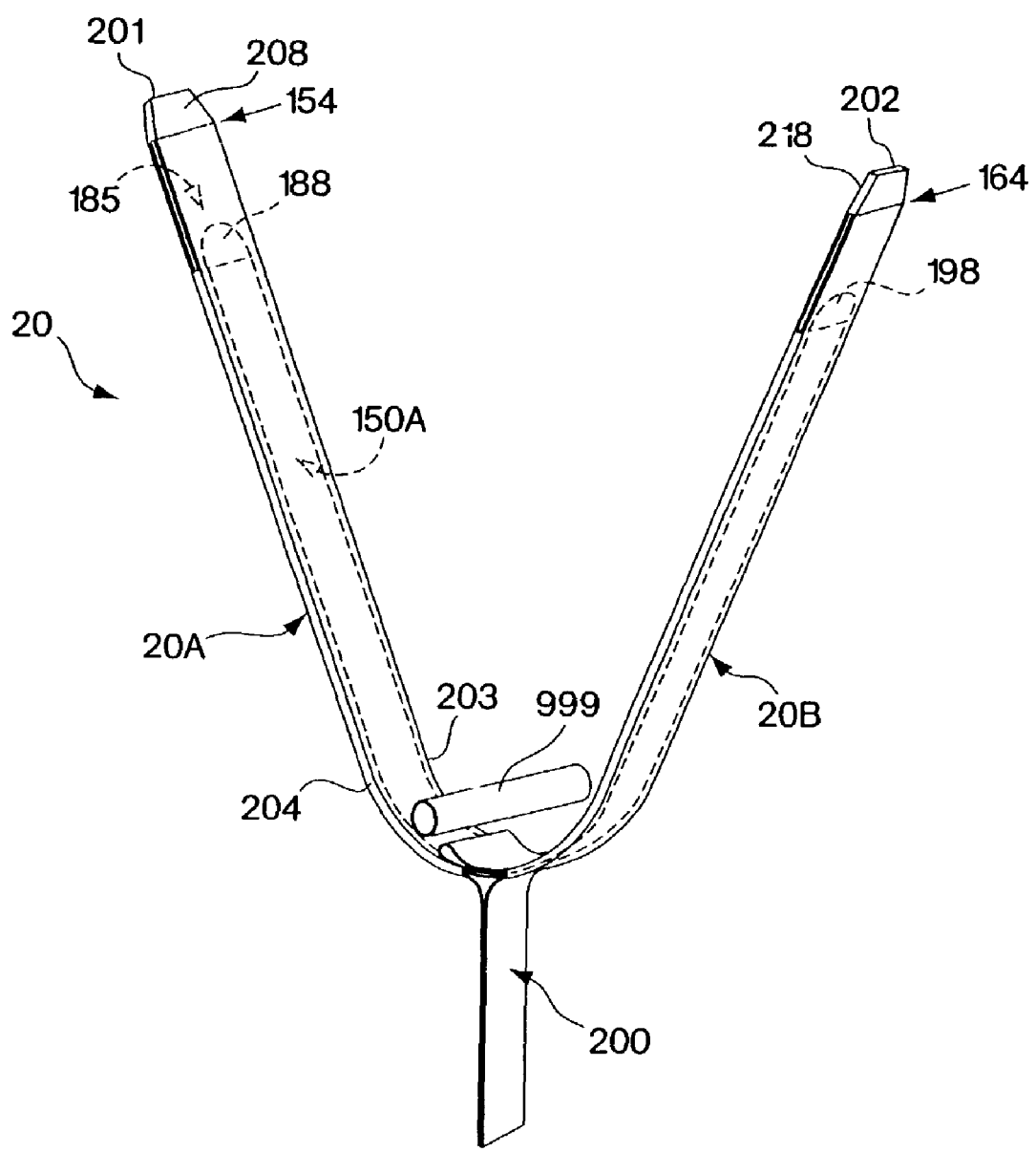
FIG. 8A illustrates one embodiment of a system for implanting an implant in a body.
Figure 8B:
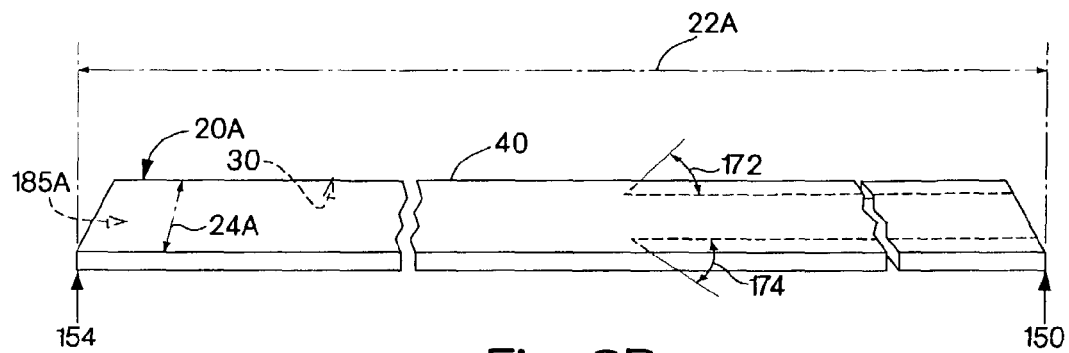
FIG. 8B illustrates a sleeve for use in the system illustrated in FIG. 8A for implanting an implant in a body.

Referring to FIG. 8A, in one embodiment according to the invention, the system includes an envelope 20 including the first sleeve 20A, the second sleeve 20B, tabs 188, 198 and an envelope hinge 200. The envelope 20 encloses the implant 10. For example, FIG. 8B illustrates the first sleeve 20A of the envelope 20 shown in FIG. 8A. The first sleeve 20A includes an inner surface 30, an outer surface 40, a proximal end 154, and a distal end 150. The first sleeve 20A has a first lumen 185A. The length of the first sleeve 20A between the proximal end 154 and the distal end 150, along the longitudinal axis 22A, is between about 4.0 inches and about 28.0 inches, preferably about 20.0 inches. The perpendicular axis 24A of first sleeve 20A measures between about 0.2 inches to about 2.0 inches, preferably between about 0.4 inches and about 0.8 inches, preferably about 0.6 inches.

Figure 8C:
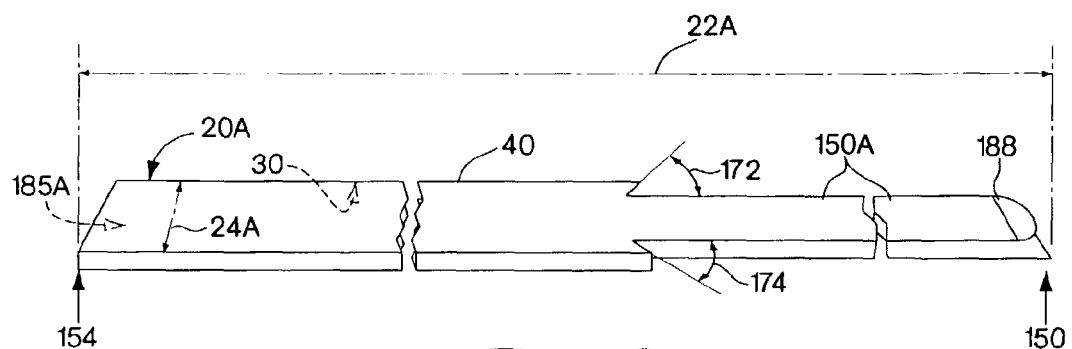
FIG. 8C illustrates another embodiment of the sleeve for use in the system illustrated in FIG. 8A for implanting an implant in a body.
Figure 8D:
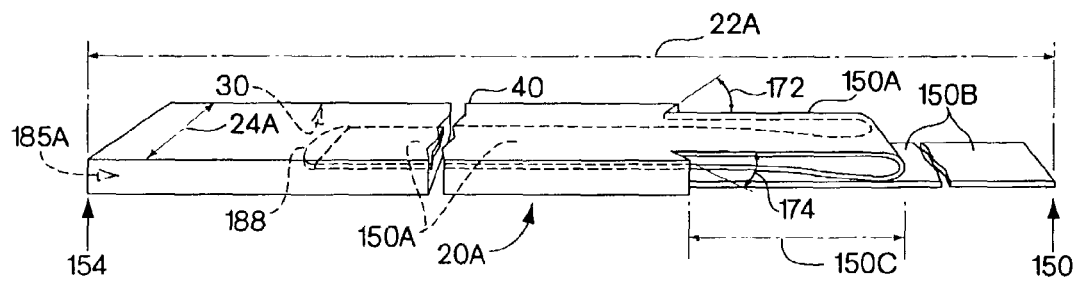
FIG. 8D illustrates another embodiment of the sleeve for use in the system illustrated in FIG. 8A for implanting an implant in a body.

Referring still to FIG. 8B, in an embodiment of the invention, two angles are cut into the first sleeve 20A, as indicated by the arrow 172 and arrow 174. The angles 172 and 174 are cut in the range of from about 20° to about 100°, or about 30° to about 70°, preferably about 60°, from the longitudinal axis 22A of the sleeve 20A illustrated in FIG. 8B. In one embodiment, the two angles 172 and 174 are cut into the first sleeve 20A at a distance of between about 0.01 inch and about 0.05 inch, preferably about 0.04 inch. In one embodiment, the distance cut into the first sleeve 20A is equivalent to the thickness of the sleeve 20A material. The angles 172 and 174 and the placement therefore may simplify tearing the envelope 20 with the tab 188, as described below, by, for example, providing a starting point for the tear. The distal end 150 portion of sleeve 20A is trimmed along the longitudinal axis 22A from the distal end 150 to angle 172 and from the distal end 150 to the angle 174. In general, the amount of the first sleeve 20A that is trimmed along the longitudinal axis 22A from the distal end 150 to each respective angle is substantially the same. Because the first sleeve 20A has a first lumen 185A, and its structure is tube-like, after the first sleeve 20A is trimmed, the distal end 150 portion has a top section 150A and a bottom section 150B as illustrated in FIGS. 8C and 8D. The longitudinal axis 22A of first sleeve 20A from the angle 174 to the end 150 of top section 150A, may measure between about 2.0 inches to about 14.0 inches, preferably about 10.0 inches. The width of top section 150A is sized so that it is equal to or smaller then the inner diameter of a first lumen 185A of the first sleeve 20A of envelope 20. For example, the width of top section 150A may measure between about 0.1 inches and about 2.0 inches.

Referring still to FIG. 8C, a tab 188 may be joined to the end of top section 150A. The tab 188 may be shaped to complement the width of the end 150 of top section 150A. Tab 188 may include, for example, adhesive that is adhered to the end 150 of the top section 150A. In another embodiment, the tab 188 may include a paperboard that is joined to the top section 150A by an adhesive, staple, heat bonding or other means known to the skilled person. It is contemplated that tab 188 may include various medical grade materials that may be joined to the top section 150A of first sleeve 20A, such as, for example TYVEK®. Alternatively, the end 150 of top section 150A may be shaped into a tab 188. In this embodiment, the tab 188 may have a texture embossed on the material of sleeve 20A or 20B, or an additional layer of the sleeve 20A or 20B material may be joined to the end 150 to form tab 188. In one embodiment, the additional layer may be tinted.

As shown in FIG. 8D, in one embodiment the top section 150A, coupled to tab 188, is pulled into a first lumen 185A of first sleeve 20A toward the proximal end 154 of first sleeve 20A. Accordingly, to ensure that the envelope can lay flat, the width of top section 150A is preferably sized so that is equal to or smaller then the inner diameter of the first lumen 185A, so that sleeve 20A lays flat when the top section 150A is pulled inside the first lumen 185A.

In a particular embodiment, the top section 150A is not fully pulled into the sleeve 20A, such that an overlap region 150C of the top section 150A remains on the outer surface 40 of the first sleeve 20A. The overlap region 150C ranges between about 0.04 inches to about 1.2 inches, preferably about 0.3 inches. The length of the bottom section 150B, measured from the angle 172 and the angle 174 along the longitudinal axis 22A to the distal end 150 of the bottom section 150B, may measure between about 2.0 inches to about 14.0 inches, preferably about 10.0 inches.

Figure 8E:
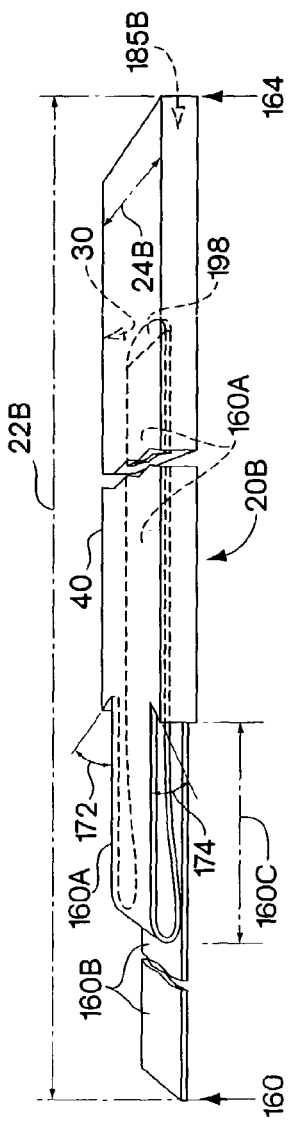
FIG. 8E illustrates another sleeve for use in the system illustrated in FIG. 8A for implanting an implant in a body.

FIG. 8E illustrates the second sleeve 20B of the envelope 20 shown in FIG. 8A. The second sleeve 20B has an inner surface 30, an outer surface 40, a proximal end 160, and a distal end 164. The second sleeve 20B includes a second lumen 185B. The length of the second sleeve 20B between the proximal end 160 and the distal end 164, along the longitudinal axis 22B, is between about 4.0 inches and about 28.0 inches, preferably about 20.0 inches. The perpendicular axis 24B of second sleeve 20B measures between about 0.2 inches to about 2.0 inches, preferably between about 0.4 inches and about 0.8 inches, preferably about 0.6 inches.

Still referring to FIG. 8E, two angles represented by the arrow 172 and the arrow 174, are cut into the second sleeve 20B at the range of from about 20° to about 100°, or about 30° to about 70°, preferably about 60°, from the longitudinal axis 22B of second sleeve 20B. In one embodiment, the two angles 172 and 174 are cut into the second sleeve 20B at a distance of between about 0.01 inch and about 0.05 inch, preferably about 0.04 inch. The second sleeve 20B is trimmed along the longitudinal axis 22B from the proximal end 160 to the angle 172 and from the proximal end 160 to the angle 174. In general, the amount of the second sleeve 20B that is trimmed along the longitudinal axis 22B from the proximal end 160 to each respective angle, 172 and 174, is substantially the same. The second sleeve 20B second lumen 185B includes a tube-like structure. After the tube-like second sleeve 20B is trimmed, the proximal end 160 includes a top section 160A and a bottom section 160B, as illustrated in FIG. 8E. The longitudinal axis 22B of second sleeve 20B from the angle 172 and the angle 174 to the end of top section 160B may measure between about 2.0 inches to about 14.0 inches, preferably about 10.0 inches. The width of top section 160A is preferably sized so that is equal to or smaller then the inner diameter of the second lumen 185B, so that sleeve 20B lays flat when the top section 160A is pulled inside the second lumen 185B. The width of top section 160A may measure between about 0.1 inch and about 2.0 inches.

Referring still to FIG. 8E, a tab 198 is coupled to the end of top section 160A. The tab 198 may be shaped to complement the width of the end 160 of top section 160A and tab 198 may be constructed as described above with reference to tab 188.

Top section 160A, coupled to tab 198, is pulled into the second lumen 185B of second sleeve 20B toward the distal end 164 of sleeve 20B. In a particular embodiment, the top section 160A is not fully pulled into the second sleeve 20B, such that an overlap region 160C of top section 160A remains on the outer surface 40 of the second sleeve 20B. The overlap region 160C ranges between about 0.04 inches to about 1.2 inches, preferably about 0.3 inches. The length of bottom section 160B, measured from the angle 172 and the angle 174 along the longitudinal axis 22B to the proximal end 160 of the bottom section 160B may measure between about 2.0 inches to about 14.0 inches, preferably about 10.0 inches.

Figure 8F:
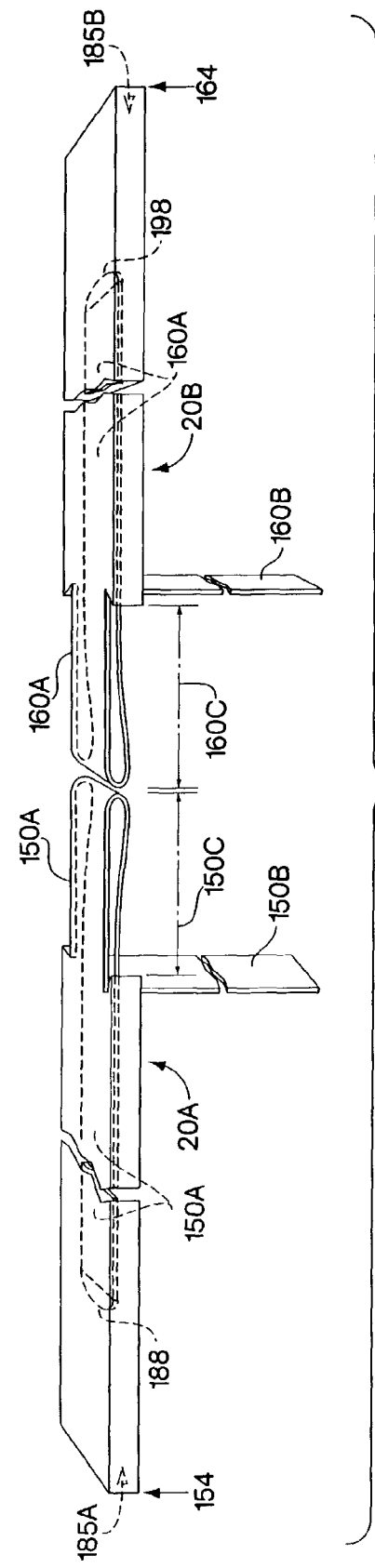
FIG. 8F illustrates making a system for implanting an implant in a body illustrated in FIG. 8A.

As shown in FIGS. 8F and 8G, the bottom section 150B of the first sleeve 20A is placed at about a 90° angle relative to the longitudinal axis 22A of the first sleeve 20A. Similarly, the bottom section 160B of the second sleeve 20B is placed at about a 90° angle relative to longitudinal axis 22B of the second sleeve 20B. The sleeves 20A and 20B are aligned in proximity to one another such that the bottom sections 150B and 160B of sleeves 20A and 20B, respectively, face one another.

Figure 8I:
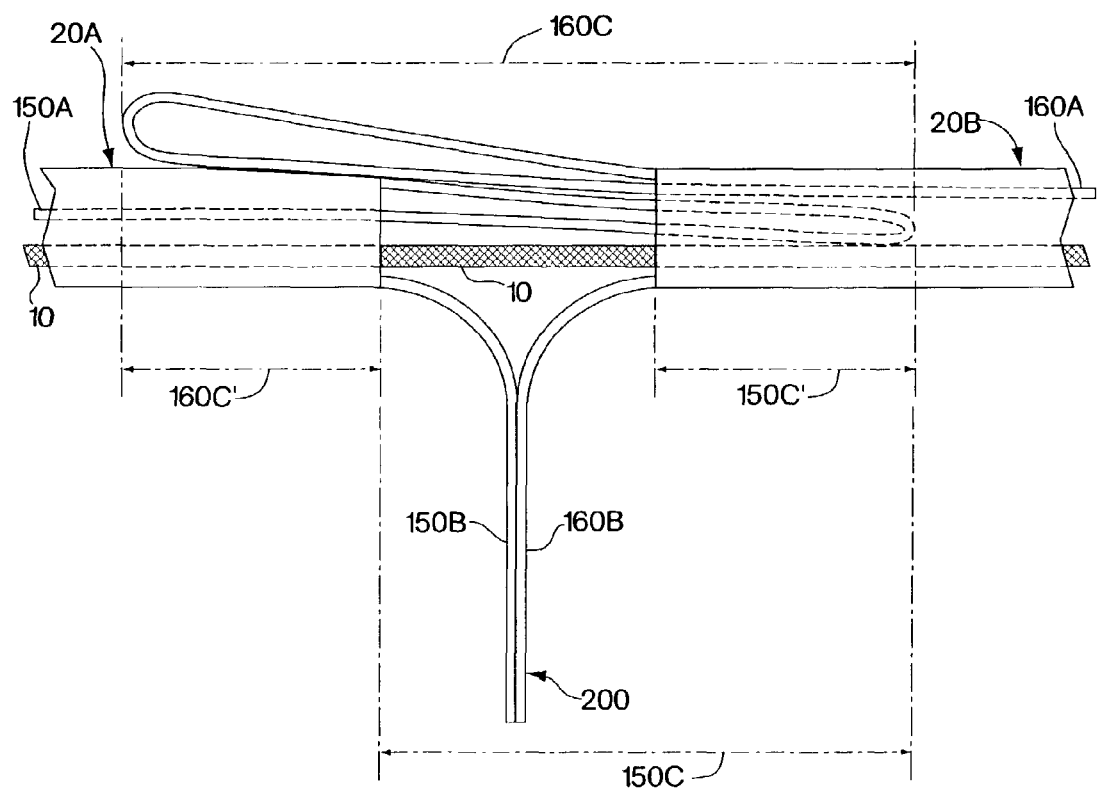
FIG. 8I illustrates another view of the system for implanting an implant in a body illustrated in FIG. 8H.

Referring now to FIGS. 8H and 8I, the bottom sections 150B and 160B are joined to one another by adhesive, staples, heat bonding or other means known to the skilled person to form hinge 200. As shown in FIGS. 8F and 8G, the proximal end 154 of first sleeve 20A and the distal end 164 of the second sleeve 20B are positioned on opposite ends of the envelope 20 formed by sleeve 20A and sleeve 20B. Referring again to FIGS. 8H and 8I, the bottom sections 150B and 160B of sleeve 20A and sleeve 20B form the hinge 200 of the envelope 20. The envelope 20 has a proximal end 154 and a distal end 164, formed by the proximal end 154 and distal end 164 of sleeve 20A and 20B, respectively. Referring again to FIG. 8G, the length of envelope 20, measured along the longitudinal axis 22 from proximal end 154, which is equivalent to the first end 201, to distal end 164, which is equivalent to the second end 202, ranges between about 4.0 inches to about 28.0 inches, or between about 12.0 inches and about 24.0 inches, most preferably 20.0 inches.

Referring to FIGS. 8G-8I, the overlap region 160C of sleeve 20B of envelope 20 may lay on top of the overlap region 150C of sleeve 20A of envelope 20. The length of overlap region 160C that is adjacent the remaining tube-like portion of the first sleeve 20A, i.e., 160C', may range between about 0.02 inches to about 0.06 inches, preferably 0.04 inches. Referring again to FIG. 8A, the overlap regions protect the implant 10 inside of envelope 20, the envelope 20 including sleeves 20A and 20B. For example, in embodiments where the envelope 20 is employed to implant a mid-urethral sling, the overlap regions 150C and 160C of the envelope 20 prevents sling stretching caused by, for example, a hemostat used in the surgery.

In another embodiment, illustrated in FIG. 8J, the angles represented by the arrow 212 and the arrow 214, are cut into the proximal end 154 of first sleeve 20A, and sleeve 20A is trimmed substantially as illustrated to form a narrow portion at the end of sleeve 20A. After the tube-like proximal end 154 of sleeve 20A is trimmed, the proximal end 154 has a top section 154A and a bottom section 154B (not shown). The top section 154A and the bottom section 154B are separated from one another. The longitudinal axis of first sleeve 20A from the angle 212 to the proximal end 154 of top section 154A, may measure between about 0.6 inches to about 4.0 inches, preferably between about 1.2 inches and about 2.0 inches. The perpendicular axis of top section 154A may measure between about 0.1 inch and about 2.0 inches. In a preferred embodiment, the perpendicular axis of top section 154A is equal to the width of the top section 150A of sleeve 20A, this enables the top section 150A to easily tear apart from the envelope. Referring to FIGS. 8J and 8K, when the proximal end 154 is trimmed forming the proximal top section 154A and the proximal bottom section 154B (not shown), pulling the top section 150A coupled to tab 188 through the first lumen 185A of first sleeve 20A toward the proximal end 154 is simplified. The opening between the sections 154A and 154B simplify accessing tab 188 to pull it and top section 150A through first sleeve 20A toward the proximal end 154. In some embodiments, the tab 188 is pulled in between the sections 154A and 154B. Thereafter, as shown in FIG. 8J, in one embodiment, a tab 208 may be used to join the proximal top section 154A and the proximal bottom section 154B. The tab 208 may include adhesive tape, glued paperboard, or other materials, as described above with reference to tab 188, that are capable of coupling together the top and bottom sections, 154A and 154B respectively. In one embodiment, after tab 208 joins the proximal top and bottom sections, at about end 154 and an opening still remains in the sleeve 20A between the top and bottom sections 154A and 154B. The tab 188 may be accessed and pulled through this opening, while the tab 208 remains at the end 154 of sleeve 20A.

Similarly, referring to FIG. 8K, the distal end 164 of sleeve 20B is trimmed at angles 212, 214 substantially as illustrated in FIG. 8J to form a narrow portion at each end of envelope 20. Thus, a distal top section 164A and a distal bottom section 164B (not shown) are formed. Because the distal top section 164A and the distal bottom section 164B are separated, pulling the top section 160A coupled to tab 198 through the inner surface of sleeve 20B through the second lumen of sleeve 20B toward the distal end 164 is simplified. In one embodiment, a tab 218 is employed to couple the distal top section 164A and the distal bottom section 164B to one another. As described above with reference to sleeve 20A, the tab 218 may be placed at the end 164 of sleeve 20B to leave an opening between the distal top and bottom sections, 154A and 164B, where tab 198 may be accessed and pulled.

As shown in FIGS. 8F and 8G, sleeves 20A and 20B are joined to form envelope 20. The first lumen 185A and the second lumen 185B form the single lumen 185 of the envelope 20. Referring now to FIG. 8H, the joined bottom sections 150B and 160B of sleeves 20A and 20B form hinge 200 of envelope 20. Various methods may be employed to join bottom sections 150B and 160B, for example, heat bonding, adhesives, or staples. Alternative medical grade materials capable of coupling the sections together such as, for example, TYVEK® may be employed. The length of hinge 200 may range between about 2.0 inches to about 14.0 inches in length. The hinge 200 may be trimmed to a shorter length that may be grasped by the operator during the method of implanting the implant, described below in accordance with FIGS. 9B-9D.

Figure 9A:
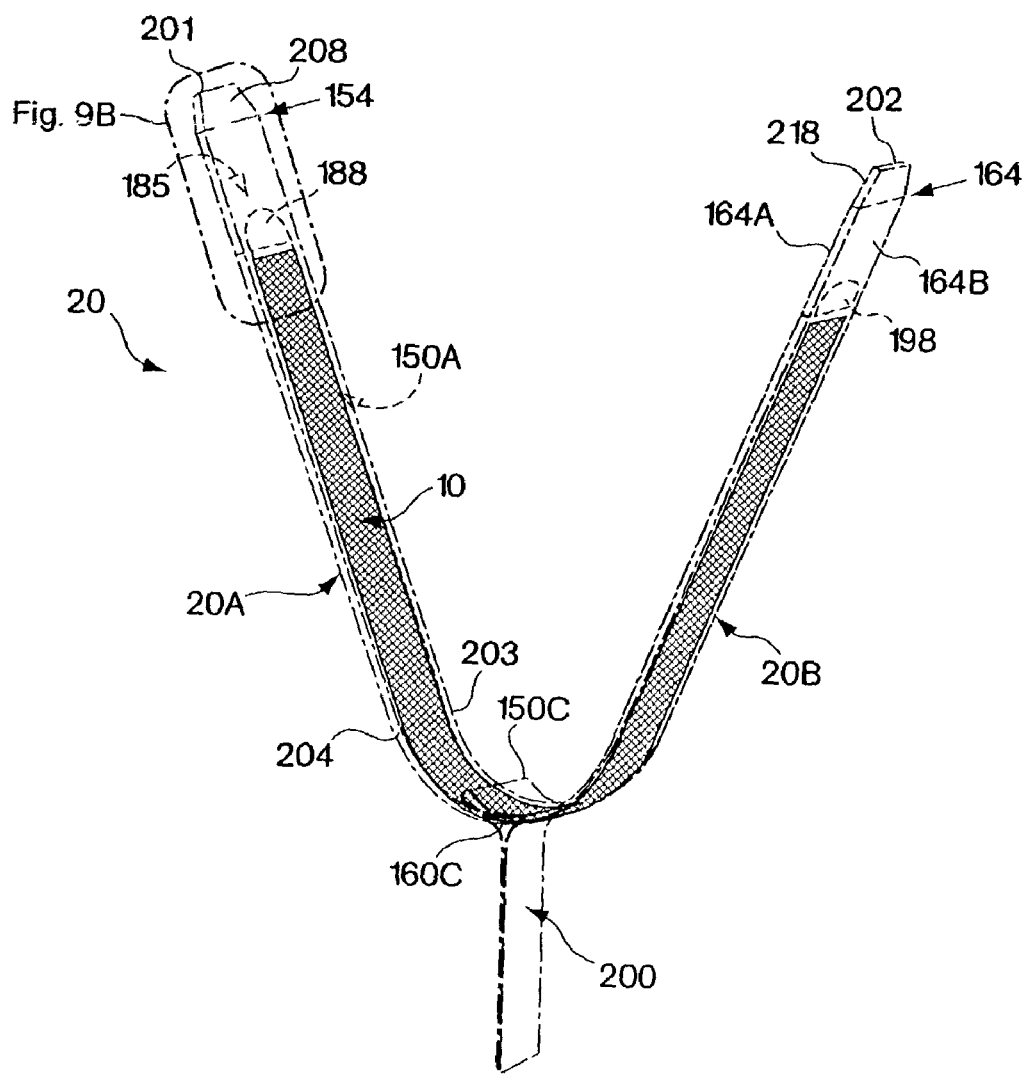
FIG. 9A illustrates another embodiment of the system for implanting an implant in a body illustrated in FIG. 8A, where the implant is a sling.

FIG. 9A illustrates one embodiment of the implant 10 positioned within the lumen 185 of the envelope 20. In this embodiment, the overlap regions 150C and 160C, cover the implant 10 enclosed within envelope 20.

In another embodiment according to the invention, referring to FIGS. 8F, 8G and 8H, the implant 10 is placed within the envelope 20 after sleeves 20A and 20B are joined at hinge 200, but prior to tabs 208 and 218 being joined to the envelope 20. The implant, for example a sling 10, may be manually inserted into lumen 185 of envelope 20. In another embodiment, the sling 10 is placed within the first lumen 185A of the first sleeve 20A manually and/or with the aid of a grasping device. Thereafter, sleeve 20B is joined with sleeve 20A to form envelope 20, with the hinge 200. The remaining portion of sling 10 may be placed within the second lumen 185B of sleeve 20B prior to or after forming hinge 200.

Figure 9B:
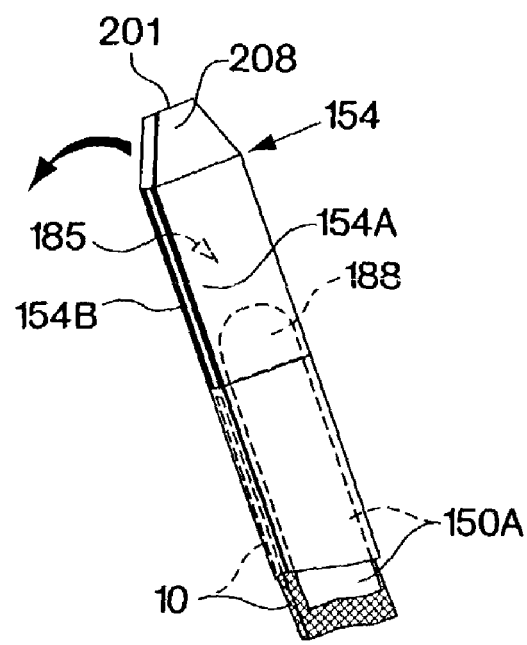
FIG. 9B illustrates another embodiment of the system for implanting an implant in a body illustrated in FIG. 9A.
Figure 9C:
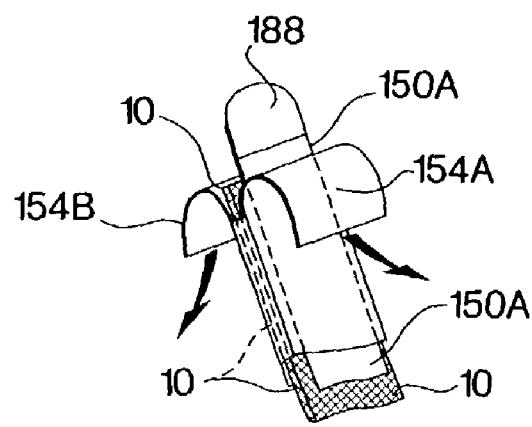
FIG. 9C illustrates another embodiment of the system for implanting an implant in a body illustrated in FIG. 9A.

With reference to FIGS. 8A and 9A-9D, in another aspect the invention includes a method for positioning the implant at an anatomical site in the body of a patient. According to one embodiment of this method of the invention, the operator positions the envelope 20 enclosing sling 10, illustrated for example in FIG. 9A, at the anatomical site, for example, the W urethra 999 or bladdemeck. Referring to FIGS. 9A and 9B, the operator accesses the tab 208 coupled to proximal top section 154A of envelope 20. Referring to FIG. 9C, tab 208 coupled to the proximal end 154 is removed by the operator thereby uncoupling proximal top section 154A from the proximal bottom section 154B.

Figure 9D:
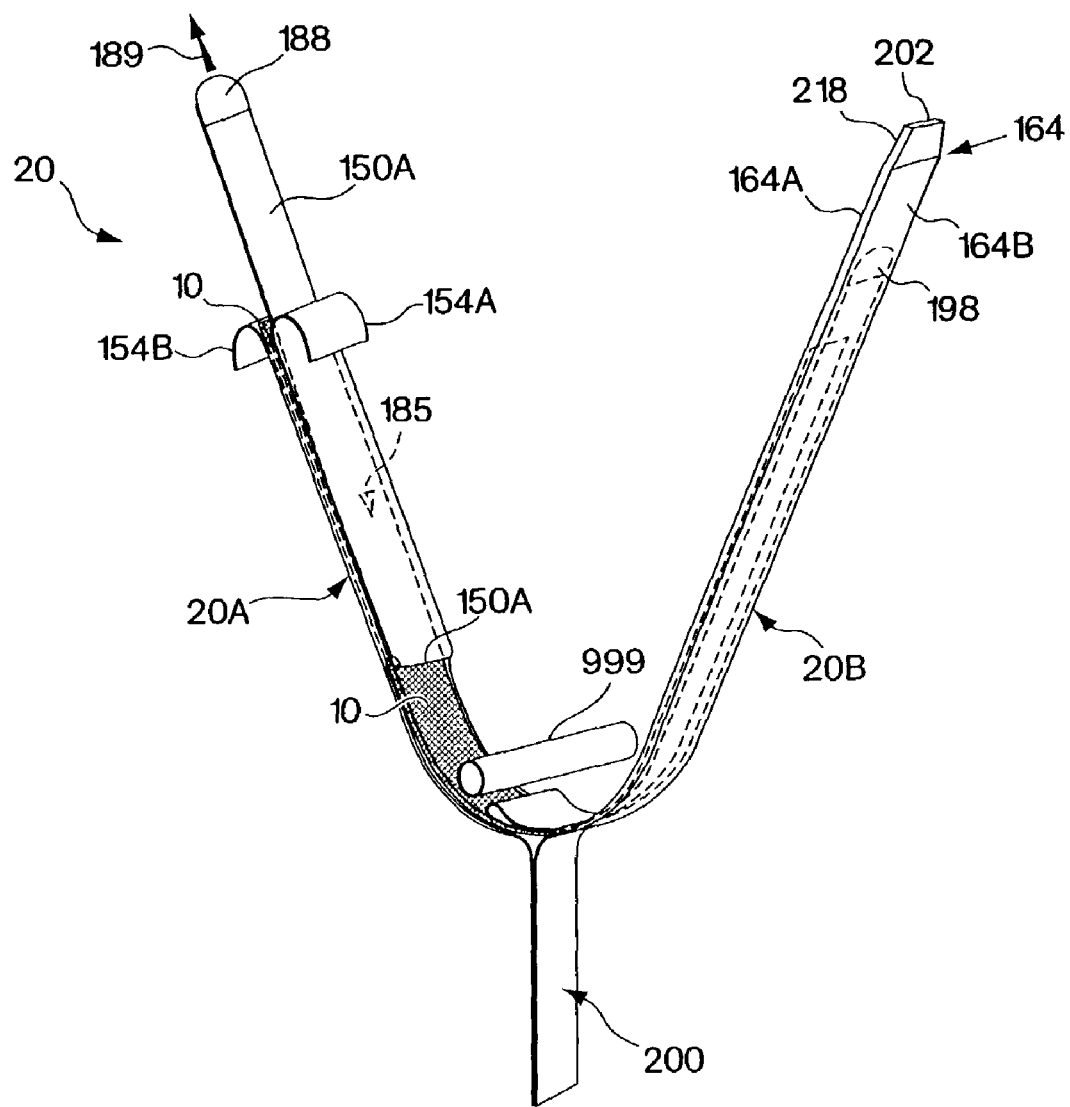
FIG. 9D illustrates another embodiment of the system for implanting an implant in a body illustrated in FIG. 9A.

Referring now to FIG. 9D, the operator grasps hinge 200 and simultaneously pulls the tab 188 in the direction indicated by arrow 189. The force on tab 188 coupled to the top section 150A tears the envelope 20 along the top portion of the first sleeve 20A. Thereafter, the top section 150A of sleeve 20A is torn away from the envelope 20 in a single piece to expose the implant sling 10. Tab 188, the top section 150A, the top of sleeve 20A, and the proximal top section 154A are torn away from the envelope 20 and the implant sling 10 is exposed. The exposed portion of the sling 10 is adjacent the urethra 999.

Still Referring to FIG. 9D, the distal end 164 coupled to tab 218 is similarly removed (not shown) and the distal top section 164A and the distal bottom section 164B are uncoupled. The operator grasps hinge 200 and simultaneously pulls tab 198. The force exerted on tab 198 coupled to the top section 160A tears these portions of sleeve 20B away from the envelope 20. Thus, tab 198, the top section 160A, the top of sleeve 20B, and the distal top section 164A are removed from envelope 20. The portion of the sling 10 previously enclosed is thereby exposed. Finally, the hinge 200 is removed along with the remainder of envelope 20, and the sling 10 remains inside the body of the patient at the anatomical site where the sling 10 was positioned by the operator, for example, at the anatomical site of the urethra 999.

Figure 9E:
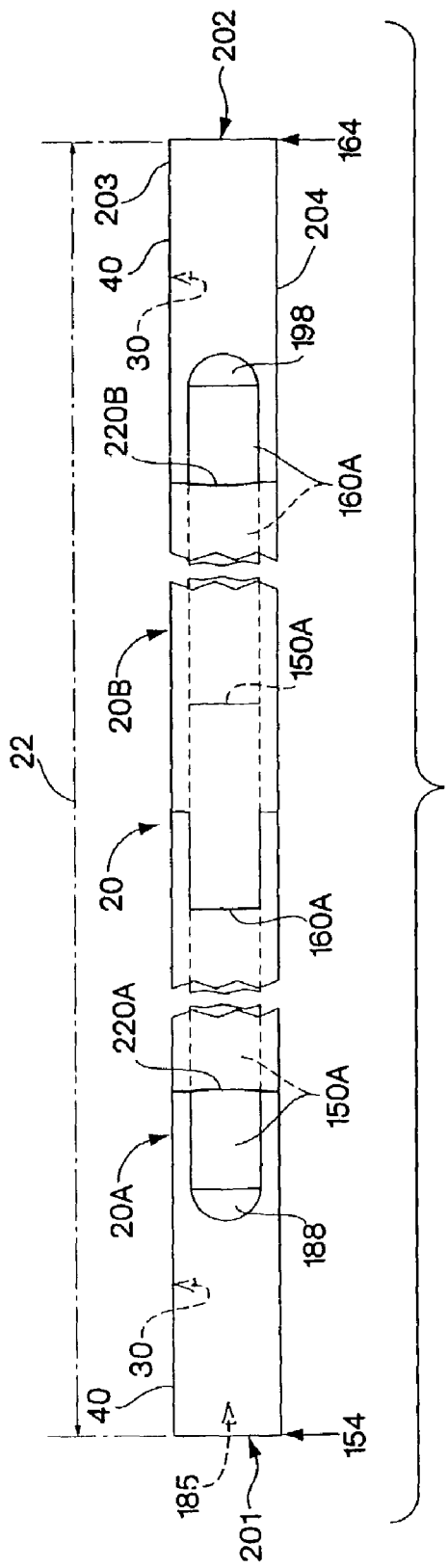
FIG. 9E illustrates another embodiment of the system for implanting an implant in a body illustrated in FIG. 8G.

In other embodiment, illustrated in FIG. 9E, the sleeves 20A and 20B described in accordance with FIGS. 8D and 8E, further include a cut 220A and a cut 220B disposed along the perpendicular axis of, the first sleeve 20A and the second sleeve 20B respectively. The cuts 220A and 220B may be disposed upon the top surface of sleeve 20A, 20B. The cut 220A may be sized so that it is equal to or longer then the perpendicular axis of the tab 188 and equal to or longer then the perpendicular axis of the top section 150A, enabling the tab 188 and top section 150A to be easily pulled through cut 220A. The tab 188 coupled to the top section 150A may be pulled through the cut 220A so that the tab 188 or the tab 188 and at least a portion of top section 150A is adjacent the outer surface 40 of envelope 20. The cut 220B may similarly be sized with respect to the perpendicular axis of the tab 198 and the top section 160A. Similarly, the tab 198 coupled to the top section 160A may be pulled though the cut 220B so that the tab 198 or the tab 198 and at least a portion of top section 160A is adjacent the outer surface 40 of envelope 20. Thus, because the tabs 188 and 198 are readily accessible from the proximal end 154 and the distal end 164 of envelope 20, the tabs 188 and 198 may be pulled to expose the implant 10 housed inside envelope 20 as described above with reference to FIG. 9D. In this embodiment of the invention, the ends 154 and 164 do not need to be removed from envelope 20 prior to pulling the tabs 188 and 198.

Figure 10A:
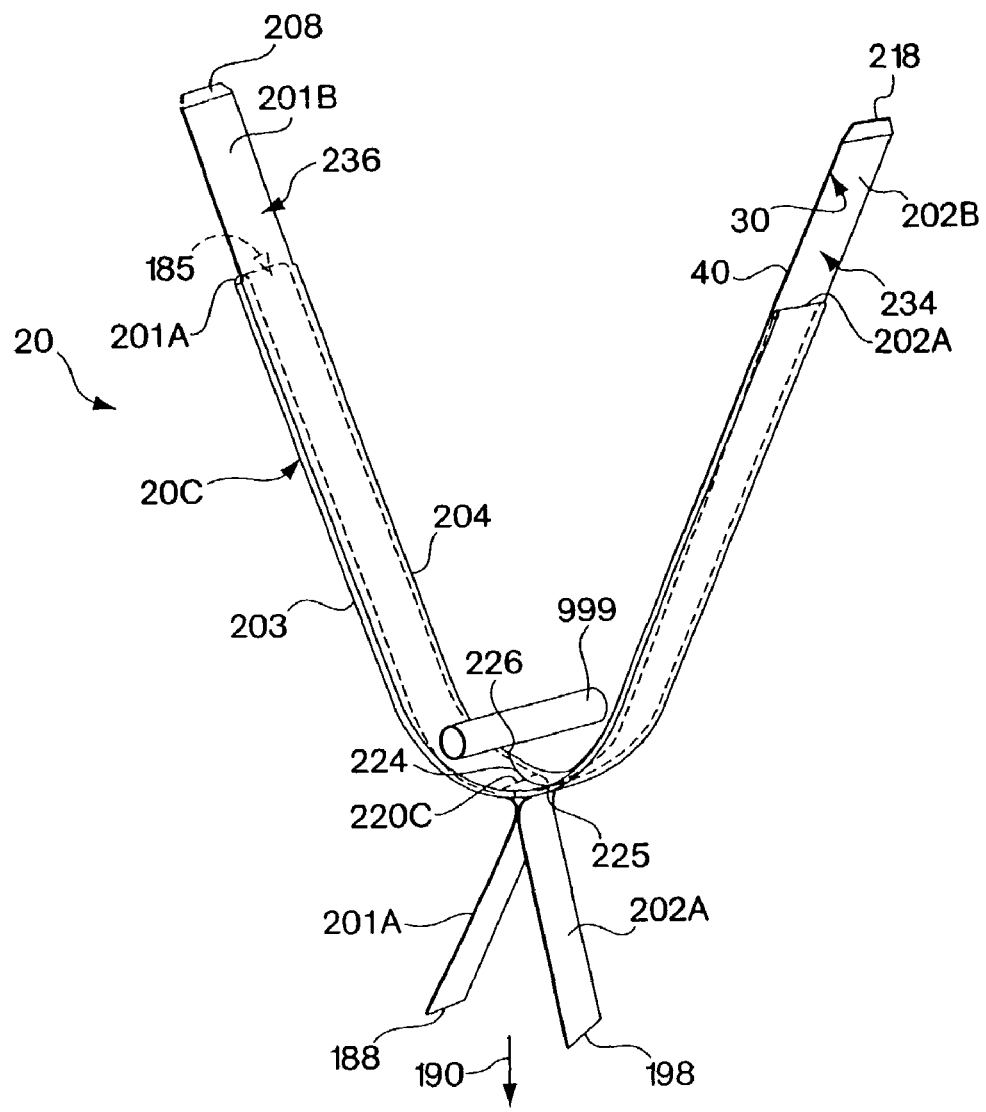
FIG. 10A illustrates one embodiment of a system for implanting an implant in a body.

In yet another aspect, the invention provides an envelope 20 illustrated in FIG. 10A. The envelope 20 includes a sleeve 20C, and tabs 188 and 198, that are adjacent the outer surface 40 of the envelope 20. Referring now to FIG. 10B, the sleeve 20C is provided, the longitudinal axis 22C of sleeve 20C, from the first end 201 to the second end 202, measures from about 12.0 inches to about 84.0 inches in length, and is preferably about 50.0 inches in length. The sleeve 20C width 24C, as measured between the side 203 and the side 204, may have a range from about 0.2 inches to about 2.0 inches, preferably between about 0.5 inches and about 0.8 inches in length, and most preferably 0.6 inches. Sleeve 20C includes a lumen 185. Also, sleeve 20C includes a top side 234 and a bottom side 236.

As illustrated in FIG. 10C, at about the mid point of the top side 234 of sleeve 20C, a cut 220C is made about perpendicular to the longitudinal axis 22C of sleeve 20C. Cut 220C has a first side 221C and a second side 222C. The length of cut 220C, measured from the first side 221C to the second side 222C, is preferably equal to or less then the width of sleeve 20C. In some embodiments, cut 220C ranges from approximately 0.2 inches to about 2.0 inches in length. A diagonal cut 224 may be made through the bottom side 236 of sleeve 20C. Cut 224 has a top side 225 and a bottom side 226. The diagonal cut 224 is made at an angle of between about 85° and about 5°, preferably about 45° relative to cut 220C. The length between the diagonal cut 224 top side 225 and the first side 221 C of cut 220C will vary according to the width 24C of sleeve 20C and the angle of diagonal line 224, in one embodiment this length ranges from about 0.1 inches to about 1.5 inches, and is preferably 0.3 inches. The distance between the diagonal cut 224 bottom side 226 and the second side 222C of cut 220C will similarly vary, and in one embodiment this length ranges from about 0.1 inches to about 1.5 inches, and is preferably 0.3 inches. In one embodiment, diagonal cut 224 is perforated along its length.

Referring still to FIG. 10C, the first end 201 of sleeve 20C is trimmed to form a first top 201A and a first bottom 201B of sleeve 20C, such that where trimmed the lumen 185 has two separate pieces, 201A and 201B. Similarly, the second end 202 of sleeve 20C is trimmed to form two separate pieces, namely, the second top 202A and second bottom 202B. The first top 201A is trimmed such that its width is equal to or less then the inner diameter of sleeve 20C, i.e. the lumen 185. Similarly, the second top 202A is trimmed to a width that is equal to or less then the diameter of lumen 185.

In some embodiments, the free end of the first top 201A includes a tab 188. Similarly the free end of the second top 202A includes a tab 198. Tabs 188 and 198, that are connected to the first top 201A and the second top 202A respectively, may be constructed as described above with reference to tab 188 and FIG. 8C.

Figure 10D:
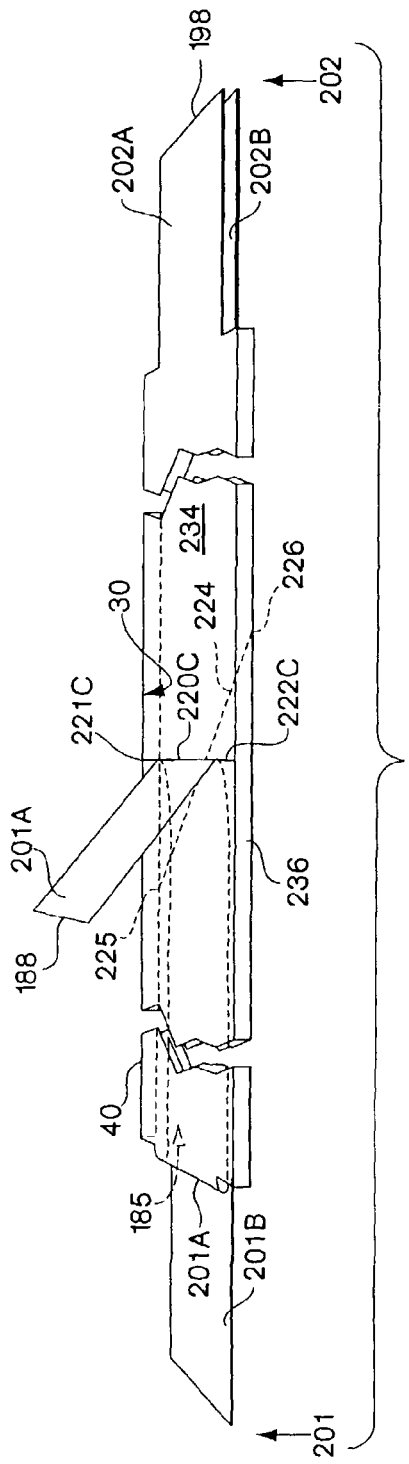
FIG. 10D illustrates a sleeve for use in the system illustrated in FIG. 10A for implanting an implant in a body.

Referring now to FIG. 10D, the tab 188 joined to the end of the first top 201A is folded into the lumen 185 and laced through lumen 185. The tab 188 joined to the first top 201A are pulled through cut 220C, so that the tab 188 and/or a portion of the first top 201A is exposed on the outer surface 40 of sleeve 20C.

Figure 10E:
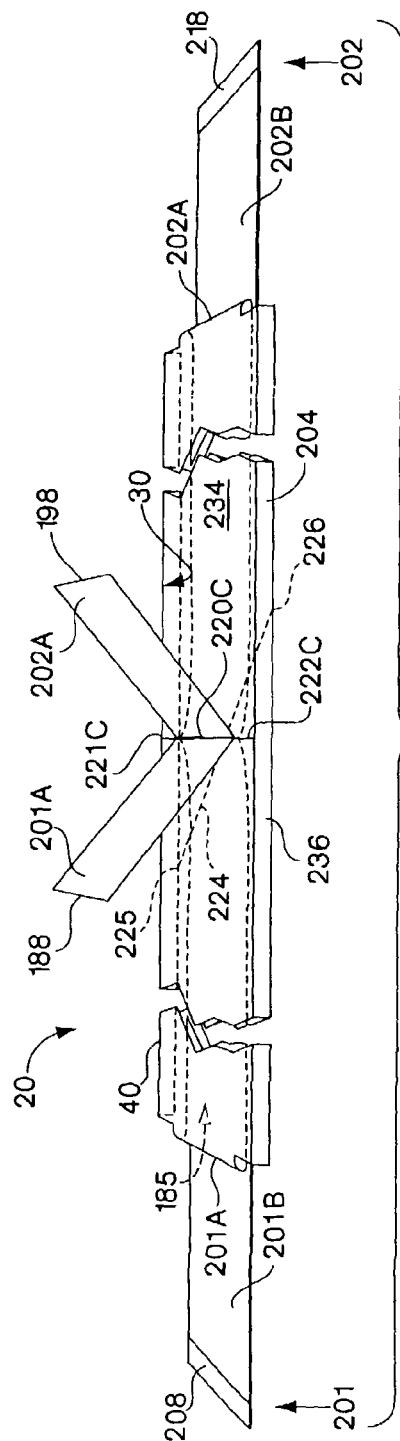
FIG. 10E illustrates a sleeve for use in the system illustrated in FIG. 10A for implanting an implant in a body.

As shown in FIG. 10D, the tab 198 joined to the end of the second top 202A is folded into the lumen 185 and laced through lumen 185. Thereafter, the tab 198 joined to the second top 202A is folded into lumen 185 and laced through lumen 185, where finally it is pulled through cut 220C, such that tab 198 and/or a portion of the second top 202A is also exposed on the outer surface 40 of sleeve 20C. After both tabs adjacent to top sections are laced through lumen 185 and pulled out cut 220C, the first top 201A is adjacent the second top 202A and both are enclosed within cut 220C. In one embodiment, as illustrated in FIGS. 10B-10E, a diagonal cut 224 is placed on the sleeve 20C. The diagonal cut 224 may simplify lacing the tab 188 and first top 201A and the tab 198 and second top 202A through lumen 185 and into cut 220C. In another embodiment, a single cut, for example a diagonal cut 224 or a cut 220C, is disposed through only one side, i.e., either the top side 234 or the bottom side 236 of the sleeve 20C. In one embodiment according to the invention, as shown in FIG. 10E, a tab 208 is placed at the free end of the first bottom 201B, similarly, a tab 218 is placed at the free end of the second bottom 202B. The tabs 208 and 218 may be made of adhesive tape, glued paperboard, or other materials as described above with reference to tab 188 and FIG. 8C. The tabs 208 and 218 may be employed in positioning the envelope inside the body of a patient.

Figure 10F:
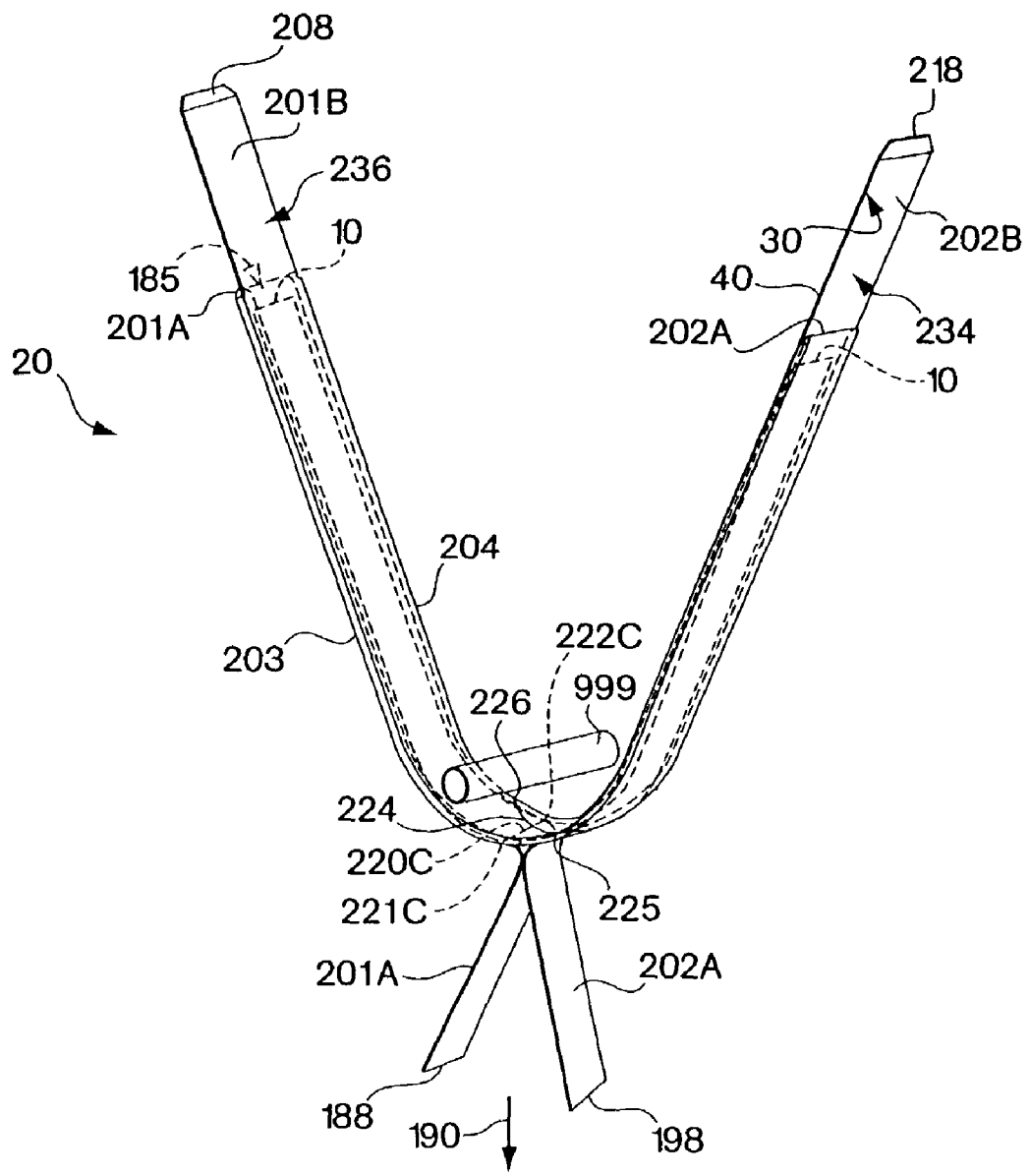
FIG. 10F illustrates another embodiment of a system for implanting an implant in a body illustrated in FIG. 10A, where the implant is a sling.

FIG. 10F illustrates one embodiment of the implant 10 positioned within lumen 185 of the envelope 20, described above with reference to FIGS. 10A-10E. In one embodiment, the envelope includes a material that is easily torn includes a material that is easily torn. Such easily torn materials are described above with reference to FIGS. 1A, 1B, 2A, 2B, 3A, and 3B and may include, for example, a material with a molecular orientation, such as a linear low density polyethylene. The implant 10 may be placed within lumen 185 of envelope 20 manually or with the aid of a grasping device. In one embodiment, the implant 10 is placed into the lumen 185 after both tabs 188 and 198 and/or both the first top 201A and the second top 202A are laced through cut 220C of sleeve 20C.

As illustrated in FIG. 10F the envelope 20 encloses the implant 10, for example, a mid-urethral sling. In another aspect, the invention includes a method for positioning the implant at an anatomical site in the body of a patient. In one embodiment (not shown), the length of the first top 201A and the length of the first bottom 201B align to enable tabs 188 and 208 to lie about adjacent when envelope 20 lays flat. Eyelets or holes positioned through the first top 201A and the first bottom 201B of envelope 20 align to form a coupling ring 355, described below with reference to FIGS. 23D and 23F, which may be attached to the delivery assembly 650 cannula 600 for implantation in the patient's body. Similarly, eyelets positioned through the second top 202A and second bottom 202B align to form a coupling ring 355 that may be employed to implant the envelope 20 in the patient's body.

According to one embodiment of the method of the invention, the operator positions the envelope 20 enclosing sling 10 at the anatomical site, for example as illustrated in FIGS. 10A and 10F, the urethra 999. In one embodiment, when the envelope 20 enclosing sling 10 is positioned adjacent the urethra 999, the bottom side 236 of the envelope 20 is adjacent the urethra. Thus, the tabs 188 and 198 and the associated portions of the first top 201A and the second top 202A, respectively, are visible from the patients vagina. In one embodiment, during the placement procedure, the operator positions the tabs 208 and 218 so that they are on the external part of the patient's body, for example, the tabs 208 and 218 are external to the patient's pelvis or abdomen.

Once positioned, the operator accesses the tab 188 joined to the first top 201A and tab 198 joined to the second top 202B, which are located in the area of the patients vagina. The operator grasps tab 188 coupled to the first top 201A and pulls the tab 188 in the direction of 190. The force on tab 188 coupled to the first top 201A tears a portion of the top side 234 of envelope 20. Thereafter the operator grasps tab 198 coupled to the second top 202A and pulls the tab 198 in the direction of 190. Similarly the force on tab 198 coupled to the second top 202A tears the remaining portion of the top side 234 of envelope 20. Finally the operator pulls the tab 208 to remove the bottom side 236 of envelope 20 from the body of the patient. In some embodiments, the bottom side 236 may be split into two pieces, for example, in the area of diagonal cut 224, accordingly, in such cases both the tab 208 coupled to the first bottom 201B and the tab 198 coupled to the second bottom 202B will be pulled away from the direction of the patients body.

In another embodiment, the implant 10 longitudinal axis is at least equal to the length of the envelope 20. In this embodiment, the implant 10 may be held within the envelope 20 by the tabs 208 and 218, for example, where the tabs are adhesive, the implant may be held within the envelope 20 by the tabs 208 and 218 disposed at each end of the envelope 20. In such embodiments, during the placement procedure, after the tabs 208 and 218 are external to the patient's body, the operator may uncouple the tabs 208 and 218, freeing implant 10. According to this method of the invention, the tabs 208 and 218 are uncoupled prior to removing the envelope 20 from the body of the patient.

In another aspect, the invention relates to an attachment piece 350 for attaching the sling 10 or the envelope 20 enclosing the sling 10, to a delivery assembly 650. In one embodiment of the invention illustrated in FIG. 11A, the attachment piece 350 includes a first member 400, such as a cylinder member 400. The cylinder member 400 of attachment piece 350 is engageable with a dilator tube member 500 of a delivery assembly 650, as described below.

Figure 11C:
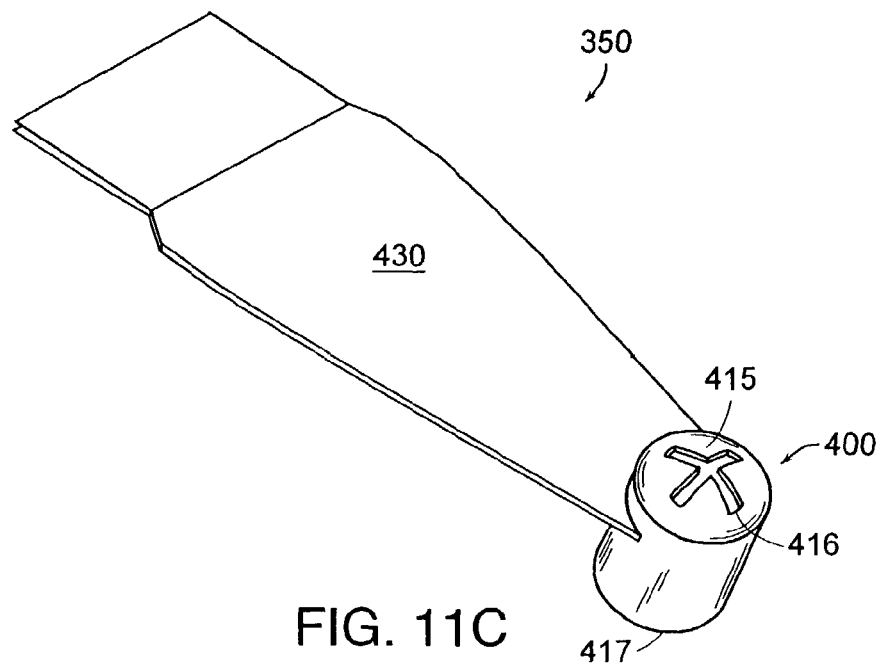
FIG. 11C illustrates a perspective view of an embodiment of an implant-delivery member such as an attachment piece for delivering an implant to a body.
Figure 11D:
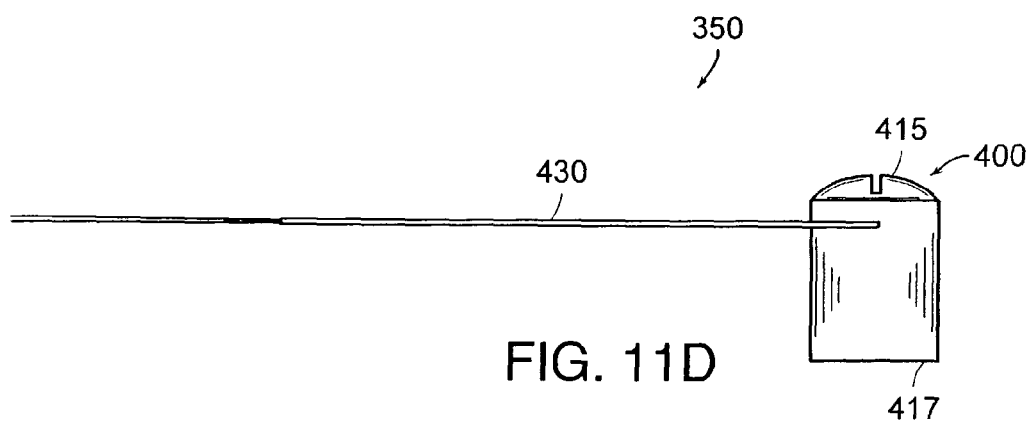
FIG. 11D illustrates a side view of the embodiment of FIG. 11C.
Figure 11I:
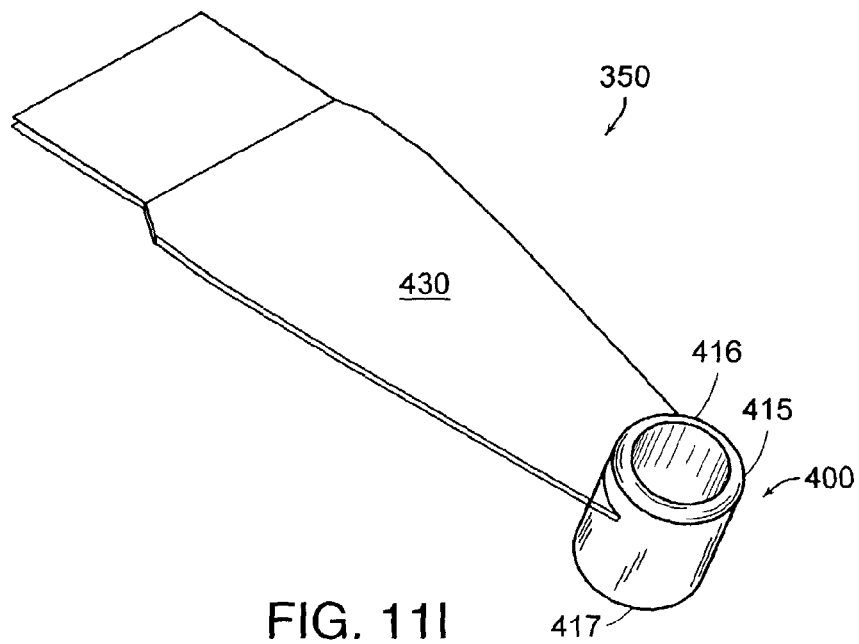
FIG. 11I illustrates a perspective view of another embodiment of an implant-delivery member such as an attachment piece for delivering an implant to a body.
Figure 11J:
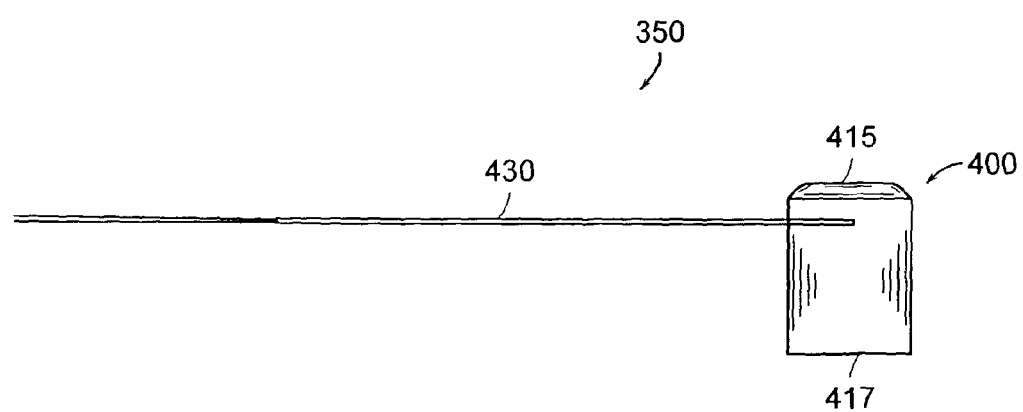
FIG. 11J illustrates a side view of the embodiment of FIG. 1.
Figure 11K:
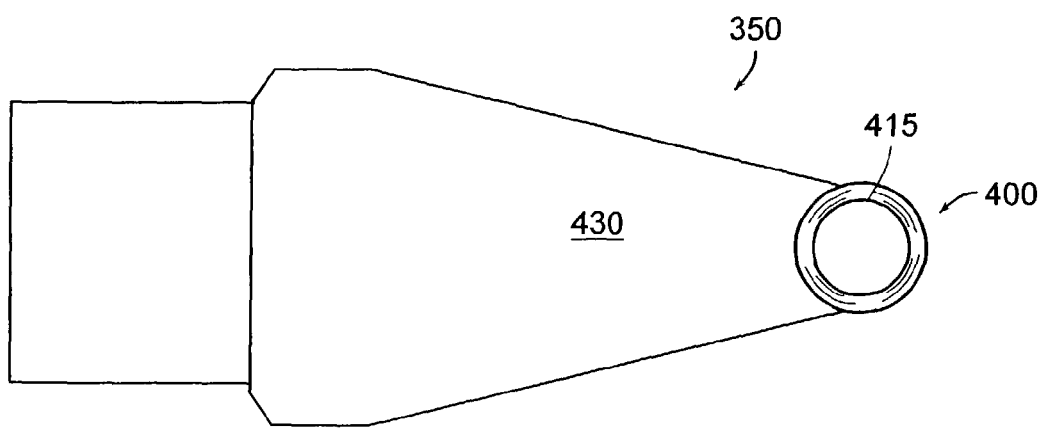
FIG. 11K illustrates a top plan view of the embodiment of FIG. 11.
Figure 11L:
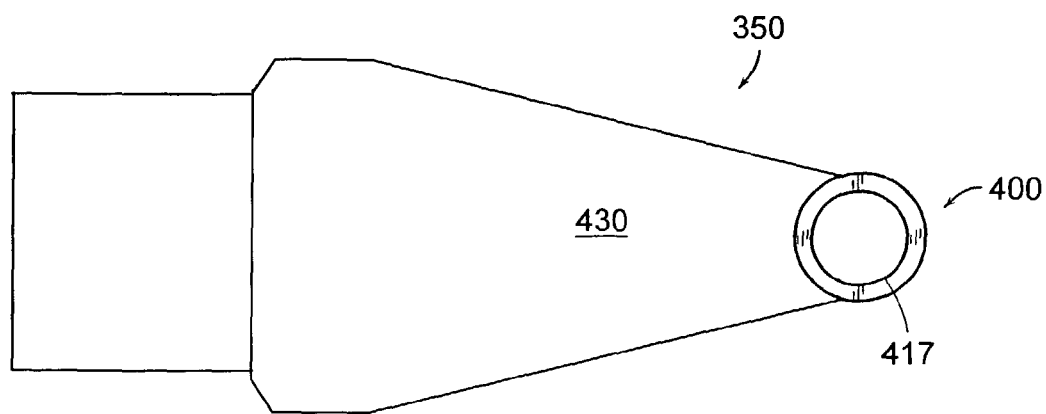
FIG. 11L illustrates a bottom plan view of the embodiment of FIG. 11.
Figure 11M:
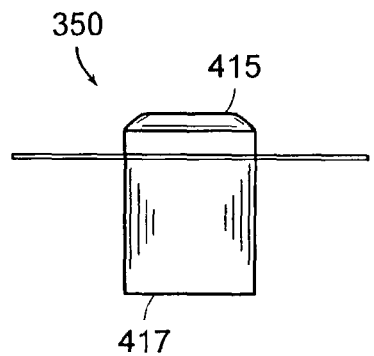
FIG. 11M illustrates a rear view of the embodiment of FIG. 11I.

Referring still to FIG. 11A, the cylinder member 400 is hollow having a least one lumen 418 and is substantially cylindrical surrounded by a wall 414. The cylinder member 400 further includes a first portion 410 at one end of the cylinder, and a second portion 420 at the opposite end of the cylinder. The height of cylinder member 400 is in the range of 0.1 to 1.0 inches, preferably 0.3 inches, and has an outer diameter in the range of 0.1 inches to 0.6 inches, preferably 0.19 inches. Cylinder member 400 is manufactured from materials such as, for example, polyethylene/ethylene vinyl acetate (EVA) blend, polyethylene, nylon, polypropylene, and thermoplastic FEP.

The cylinder member 400 is divided into a first portion 410 at one end of the cylinder and a second portion 420 at the end opposite to the first portion 410. The length of the first portion 410 is 20-40% and the length of the second portion 420 at the opposite end of the cylinder is 60-80% of the total length of the cylinder member 400. In one embodiment of the invention, an appendage 430 extends laterally outward from the wall 414 of the cylinder member 400 at the interface 412 of the first portion 410 of the cylinder member 400 and the second portion 420 of the cylinder member 400 as shown in FIG. 11A.

Referring still to FIG. 11A, in one embodiment according to the invention, cylinder member 400 further includes an appendage 430 which extends from the side of the cylinder member 400 at about one-third of the distance along the long axis of the cylinder member 400 from a first end 415 to a second end 417. Appendage 430 is substantially flat. The shape of appendage 430 permits appendage 430 to flex up or down, depending on which direction it is moved through the body of the patient. Appendage 430 conforms to the shape of the delivery assembly dilator tube when the cylinder member 400 is moved through the patient's tissue, described below. Appendage 430 is bonded, such as molded or otherwise securely attached, to the cylinder member 400. Appendage 430 measures in the range of about 0.2 to 1.0 inches in width and 0.5 to 2.0 inches in length, preferably 0.6 inches by 1.0 inches. Materials used in the manufacture of appendage 430 include, but are not limited to, polyethylene/ethylene vinyl acetate blend, polyethylene, nylon, polypropylene, and thermoplastic FEP. The appendage 430 is manufactured from materials that are sufficiently flexible to pass through the patient's tissue without tearing, or otherwise traumatizing the tissue. The appendage 430 is bonded to the cylinder member 400 by an adhesive, heat sealing, or other means known to the skilled person. In one embodiment, the cylinder member 400 is heat bonded to the envelope 20 material. Alternatively, appendage 430 and cylinder member 400 are manufactured as a single piece, for example, by injection molding.

Referring now to FIG. 11B, a free end 435 of appendage 430 is attachable to the free end 436 of an envelope or sleeve 20 enclosing the implant 10, for example, an implantable sling 10 used for treatment of female urinary incontinence. Alternatively, the free end 435 of appendage 430 is attachable to, for example, a free end 434 of the implantable device 10. In yet another embodiment, according to the invention, the free end 434 is bonded, or otherwise securely attached, to the cylinder member 400.

Thus, accordingly to the invention, the implantable device 10 is bonded, or otherwise securely attached, to the cylinder member 400. The implantable device 10 is not clamped, clipped, or pierced. Accordingly, the implantable device 10 other than being bonded to a member 400, is free to be manipulated in a plurality of planes when it is introduced into the patient's body.

The free end 435 of the appendage 430 and the free end 436 of the envelope 20, are attached by, for example, heat bonding, suturing or adhesive bonding. If heat is used to bond the appendage 430 to the envelope 20, the glass transition range of the materials used to manufacture the appendage 430 and the envelope 20 must be similar to permit a satisfactory bond joint. In a particular embodiment of the invention, the appendage 430 and the envelope 20 are manufactured from the same materials, for example, the material used to manufacture appendage 430 and envelope 20 may be polyethylene.

Referring now to FIG. 12A, a dilator tube 500 includes an elongated hollow member 510 and a tip 520, for example, a conical tip. The elongated hollow member 510 is 4.0 to 14.0 inches, preferably 8.0 inches in length, and 0.2 to 0.4 inches, preferably 0.25 inches, in outer diameter. The lumen of the elongated hollow member 510 is 0.1 to 0.7 inches in diameter, preferably 0.19 inches in diameter and is enclosed by tube wall 516. Tube wall 516 is 0.01 to 0.08 inches thick, preferably 0.03 inches. The hollow elongated member 510 terminates at end 560 where it abuts the conical tip 520. Materials used to manufacture dilator tube 500 include, but are not limited to, polyethylene, polypropylene, and nylon.

Referring to FIG. 12B, the conical tip 520 is hollow and cone-shaped. The base 514 of the conical tip 520 is configured to abut the end 560 of the elongated hollow member 510. In one embodiment, referring again to FIG. 12A, the conical tip 520 includes an aperture 402.

Figure 13:
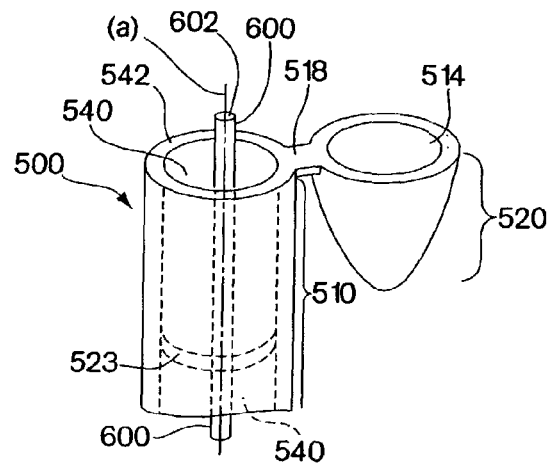
FIG. 13 illustrates an embodiment of the dilator tube and cannula according to the invention.

Illustrated in FIG. 12A, in one embodiment, according to the invention, the wall 516 of dilator tube 500 includes a cut 512 which is substantially perpendicular to the long axis of elongated hollow member 510 and is positioned near or substantially adjacent to the base 514 of the conical tip 520. The cut 512 forms the distal end 560 of the elongated member 510 and extends through nearly the entire circumference of the wall of dilator tube 500 but stops short of severing the conical tip 520 from the elongated hollow member 510 of the dilator tube 500. Accordingly, a flap 518 of wall 516 remains joining the conical tip 520 to the elongated member 510. The flap 518 thus acts as a hinge, as illustrated in FIG. 13, permitting at least 90°, preferably 180° of articulation of the conical tip 520 relative to the long axis of the elongated member 510. Other means of attaching the conical tip 520 to the wall 516 other than those illustrated are also contemplated by the invention and are not limited to those illustrated.

Referring to FIG. 13, in one embodiment of the invention, a cannula 600, described in greater detail below, is inserted into the lumen 540 of the elongated hollow member 510 of the dilator tube 500. The cannula 600 may be advanced in the lumen 540 of the hollow member 510 until the end 602 of the cannula 600 emerges from an opening 542 formed at the end of the elongated hollow member 510 substantially adjacent the hinge 518.

Figure 11N:
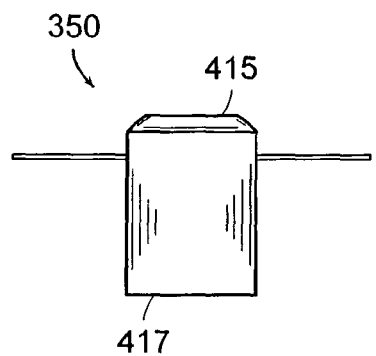
FIG. 11N illustrates a front view of the embodiment of FIG. 11I.

Referring now to FIGS. 11A-11N, in one embodiment of the invention, the top 415 of the cylinder member 400 includes one or more slits 416 which extend through the top 415 into the lumen 418 of the cylinder member 400. As illustrated in FIG. 11 A, in one embodiment of the invention, the slits 416 through the top 415 of cylinder member 400 may be in the shape of an "X." Embodiments of the slits 416 are not limited to those illustrated and may include, for example, Y-shape, V-shape, O-shape, or curvilinear. In one embodiment, the top 415 of the cylinder has a conical shape, which is slit by the one or more slits 416. The shape of the top 415 and/or the slits 416 provide the cylinder member 400 with a shape that assures that there is one way to place the cylinder member 400 into the lumen 540 of dilator tube 500. Additional means or shapes that ensure one way placement of member 400 may be employed. In the illustrated embodiment, the member 400 is shaped as a cylinder so that it mates with the lumen 540 of the hollow member 510 of dilator tube 500. Accordingly, other suitable mating dilator tube 500 lumen 540 and cylinder member 400 shapes may be selected, such as, for example, square, triangle, rectangle, or star. In one embodiment, the slits 416 permit one-way assembly of cylinder member 400 over the cannula 600, described below.

The second portion 420 of the cylinder member 400 is cylindrical in shape and hollow. The height of the second portion 420 is 0.07 to 0.7 inches, preferably 0.2 inches, or 2-3 times the height of the first portion 410 of the cylinder member 400. The dimensions of the second portion 420 are configured to enable the second portion 420 to be seated within the lumen 540 of the dilator tube 500, described below. The dimensions of the first portion 410 and the second portion 420 of cylinder member 400 may be configured to permit the cylinder member 400 to enter the lumen 540 of dilator tube 500 one way, i.e., so that the second portion 420 is inserted into the dilator tube 500 lumen 540. These dimensions are selected to prevent inadvertent introduction of the first portion 410 of cylinder member 400 into the lumen 540 of the dilator tube 500. This one way configuration of the cylinder member 400 with the lumen 540 of dilator tube 500 assures proper positioning of the implant 10 inside the patient's body. In one embodiment of the invention, the free end 417 of the second portion 420 of cylinder member 400 has a chamfered edge to permit its ease of location in the lumen 540 of dilator tube 500.

Figure 14:
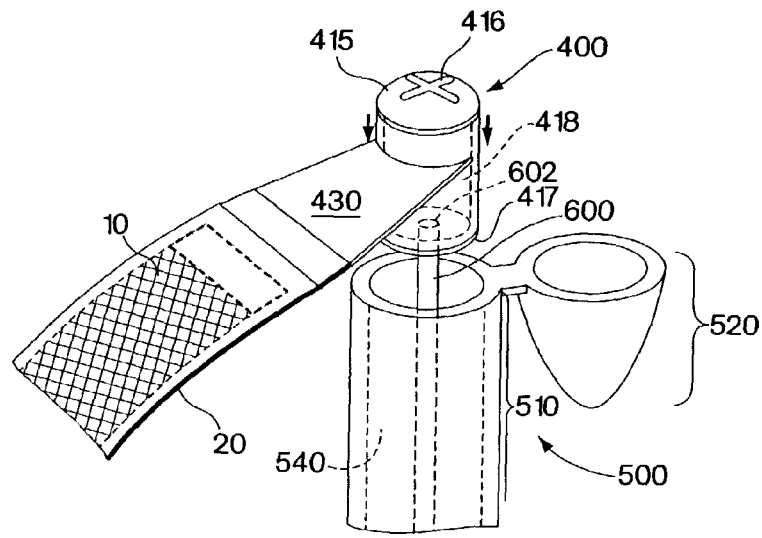
FIGS. 14-17 illustrate an embodiment of the steps according to the method of the invention for seating and securing the attachment piece to the dilator tube.
Figure 15:
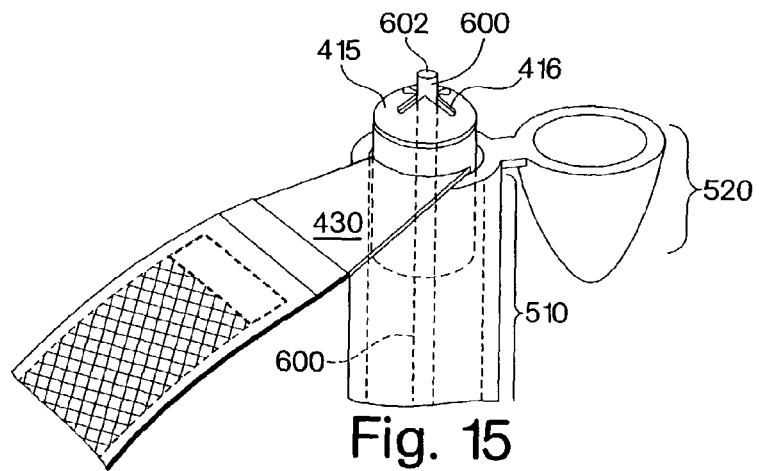

Referring now to FIG. 14, the cylinder member 400 attached by appendage 430 to an implant device such as the envelope 20 enclosing the sling 10, is introduced into the lumen 540 of the elongated member 510 of the dilator tube 500. The cylinder member 400 is seated into the lumen 540 of the elongated member 510 of dilator tube 500 thereby anchoring the cylinder 400 to the dilator tube 500. The cannula 600 is introduced from the lumen 540 of the dilator tube 500 into the lumen 418 of the hollow cylinder member 400 until the end 602 of the cannula 600 emerges from the top 415 of the cylinder member 400 through the slit 416 as illustrated in FIG. 15.

Figure 16:
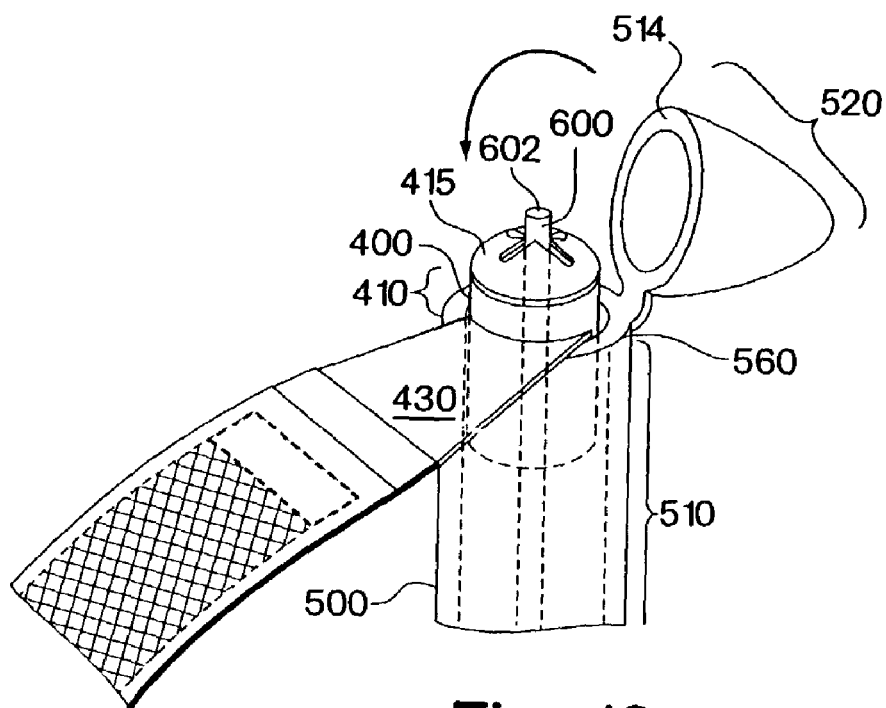
Figure 17:
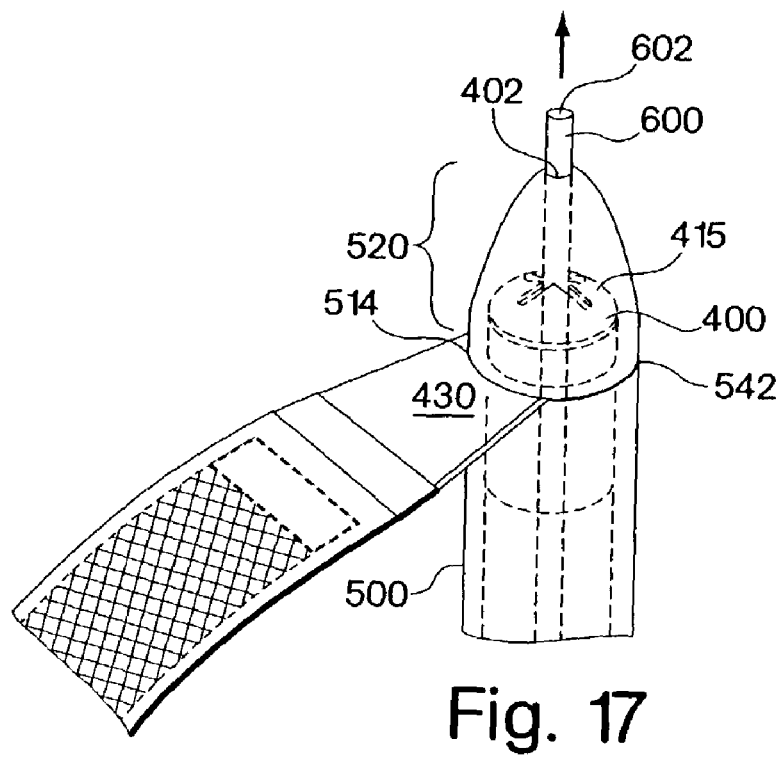

Referring now to FIG. 16, with the end 602 of the cannula 600 extended beyond the end 415 of the cylinder member 400, the conical tip 520 of the dilator tube 500 is rotated over the top of the first portion 410 of the cylinder member 400. Thus, as illustrated in FIG. 17, the appendage 430 of the cylinder member 400 is trapped between the distal end 542 of the elongated member 510 of dilator tube 500 and the bottom 514 of the conical tip 520 of dilator tube 500. In this position, the conical tip 520 encloses the first portion 410 of the cylinder member 400 thereby joining the sling 10, or the envelope 20 and the sling 10, by the appendage 430 to the dilator tube 500 of the delivery assembly 650.

Referring still to FIG. 17, the cannula 600 can be further extended through the slits 416 in the top 415 of the cylinder member 400, and through the aperture 402 at the end of conical tip 520. When the end 602 of cannula 600 emerges through the aperture 402 at the end of the conical tip 520, the conical tip 520 is fixed in position and can not move laterally thereby locking the sling 10 to the dilator tube 500 of the delivery assembly 650.

Figure 18A:
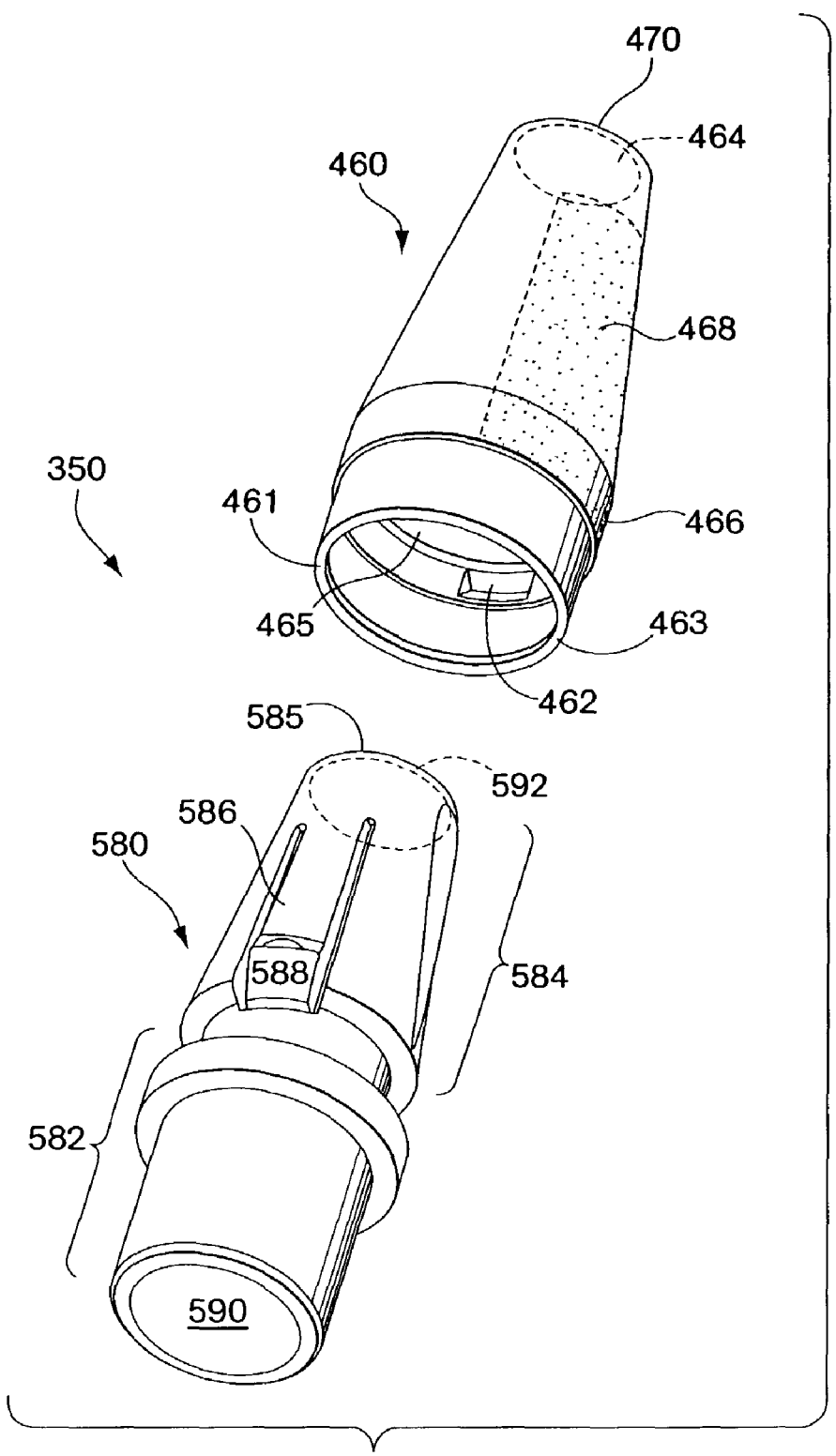
FIG. 18A illustrates another embodiment of the attachment piece according to the invention.

Referring now to FIG. 18A, in another embodiment according to the invention, the attachment piece 350, includes a cone 460 and a collet 580. The cone 460 is bonded to the implant 10 or envelope 20 by adhesive bonding, heat bonding, suturing, or any other bonding means known to the skilled person. In one embodiment, referring now to FIGS. 1A and 18A, the width 24 of the first end 201 of envelope 20 is heat bonded about a portion of the outer diameter of cone 460 at attachment site 466. In one particular embodiment, width 24 of the first end 201 of envelope 20 covers about one half of the outer circumference of cone 460 at attachment site 466. The cone 460 and collet 580 are manufactured from materials such as polypropylene, nylon, acrylonitrile butadiene styrene (ABS), polycarbonate, preferably polyethylene or polyethylene/ethylene vinyl acetate blend to permit heat bonding to the sleeve. The cone 460 and collet 580 may be manufactured by injection molding.

With continued reference to FIG. 18A, the collet 580 is generally cylindrical, includes a lumen 590 and measures about 0.3 inches to 0.9 inches, preferably about 0.6 inches in length and 0.1 inches to 0.7 inches, preferably 0.3 inches in diameter at the widest point. A first end portion 582 of the collet 580, illustrated in FIG. 18A, is a hollow cylinder and occupies about 25-50% of the length of the collet 580. The second end portion 584 of the collet 580, illustrated in FIG. 18A, is tapered from the first end portion 582 to the second end 585 of the collet 580. In one embodiment, the first end portion 582 of the collet 580 is inserted into the lumen 540 of the elongated hollow member 510 of the dilator tube 500 and bonded into the dilator tube. In embodiments where the collet 580 is bonded into the distal end 560 of the elongated hollow member 510 of the dilator tube 500, the cone 520 may be removed from the dilator tube 500. An aperture 592 is positioned at end 585 of the collet 580. The tapering of the collet 580 enables ease of passage through tissues in the patient's body when the attachment piece 350 is advanced without the cone 460 in place.

Referring still to FIG. 18A, a pair of cantilever locking tabs 586 are positioned on the outside surface of the tapered second portion 584 of the collet 580. The cantilever locking tabs 586 deflect inward when an exterior force is applied and the tabs 586 return to their original position to provide a snap engagement with a corresponding locking receptacle 462 on the cone 460, described below.

Referring still to FIG. 18A, a stabilizing bump 588 is provided on the cantilever locking tab 586 to stabilize the cantilever locking tabs 586 when the tabs 586 are engaged with the cone 460. The stabilizing bump 588 locks the collet 580 onto the cone 460.

With continued reference to FIG. 18A, in one embodiment, the cone 460 of the attachment piece 350 includes a substantially rectangular locking receptacle 462 positioned in the wall 463 in the lumen 465 side near the first end 461 of the cone 460. The cantilever locking tabs 586 in the collet 580 engage the locking receptacle 462 to secure the collet 580 to the cone 460. The number of locking receptacles 462 on the collet 580 are at least as many as the number of cantilever locking tabs 586 positioned on the cone 460. In another embodiment of the invention, the locking receptacle 462 is a continuous receptacle (not shown) that encircles the wall 463 on the lumen 465 side of the cone 460.

The cone 460 tapers from the cone first end 461 to a cone second end 464. In one embodiment, an aperture 470 is positioned at the second end 464. The taper of the cone 460 parallels the taper of the second portion 584 of the collet 580. The similar tapers of the cone 460 and the second portion 584 of the collet 580 enable the second end 584 of the collet 580 to fit snugly within the lumen 465 of the cone 460. The cone 460 includes a surface 468 on the outside surface of the cone 460 for attachment of the implant 10 or sleeve 20.

Figure 18B:
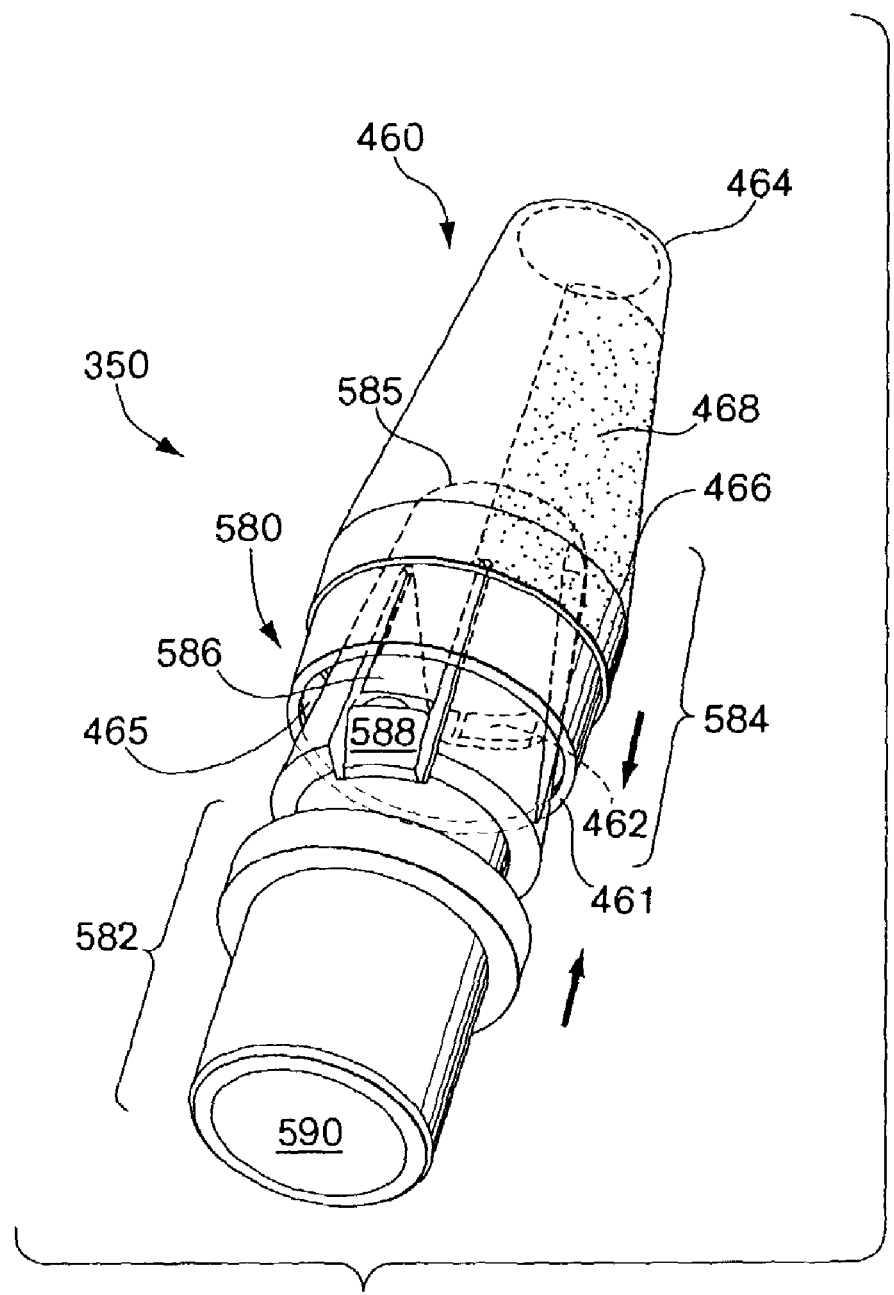
FIG. 18B illustrates assembly of the attachment piece illustrated in FIG. 18A.

Referring to FIG. 18B, to lock the cone 460 with the implant attached at surface 468 to the collet 580, the second end portion 584 of collet 580 is introduced into the lumen 465 of the cone 460. The cantilever locking tabs 586 and stabilizing bump 588 fit into the corresponding locking receptacles 462 on the cone 460 to secure the collet 580 to the cone 460. The interface between the cone 460 and collet 580 must be sufficiently secure to withstand between about a 0.5 pound to about a 10 pound, preferably a four pound separation force. A cannula 600 may be introduced through the lumen 590 of the collet 580, the lumen 465 of the cone 460, the aperture 592 of the collet 580, and the aperture 470 of the cone 460. In one embodiment, cannula 600 is sized to fit snugly inside lumen 590 of the collet 580. The presence of cannula 600 in lumen 590 of the collet 580 prevents locking tabs 586 from deflecting inward. The cannula 600 and the attachment piece 350 including the cone 460 and the collet 580 may be used to introduce the implant 10 or envelope 20 joined to the cone 460 into the body of the patient. With the collet 580 locked to the cone 460, the collet 580 can not be removed from the cone 460 without deflecting the locking tabs 586. The cone 460 provides a smooth transition from the leading cannula 600 to the dilatation feature of the collet 580. With the cannula 600 inserted in the attachment piece 350, the cantilever tabs 586 are fully engaged in the receptacle 462 of the cone 460 locking the cone and collet of the attachment piece 350 together preventing the cantilever tabs 586 from deflecting until the attachment piece 350 is removed from the cannula 600.

In another embodiment of the invention, the cone 460 includes an orientation key to permit assembly of the cone 460 to a predetermined orientation on the collet 580 during assembly of the attachment piece 350.

In another aspect, referring again to FIG. 11 A, the invention is a method for attaching a medical device 10, such as a sling implant 10 for the treatment of female urinary incontinence, to a delivery assembly 650. According to one embodiment of the method of the invention, the cylinder member 400 is pre-attached via appendage 430 to the implant 10 or to the envelope 20 enclosing the implant 10. An operator, such as a physician, seats the second portion 420 of the cylinder member 400 into the lumen 540 of the elongated hollow member 510 of the dilator tube 500 to anchor the cylinder member 400 in the dilator tube 500. Conical tip 520 is rotated about hinge 518 until the conical tip 520 is seated over the first portion 410 of the cylinder member 400. The cannula 600 is advanced towards the top 415 of the cylinder member 400 until the end 602 of the cannula 600 emerges through slits 416 in the top 415 of the cylinder member 400. The cannula 600 is further advanced until the end 602 of the cannula 600 emerges through the aperture 402 in the conical tip 520.

Figure 19A:
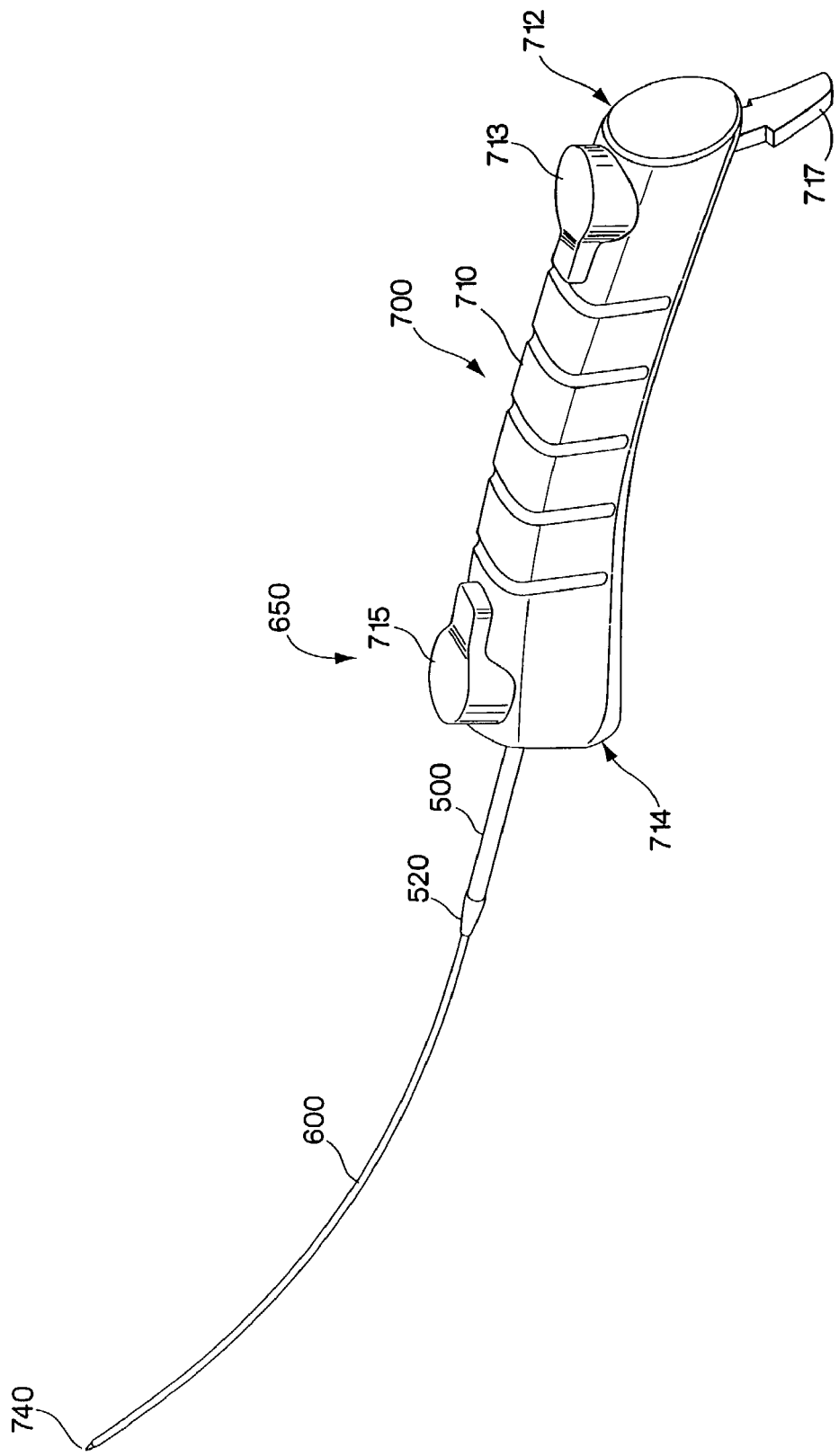
FIG. 19A illustrates an embodiment of the delivery assembly according to the invention.
Figure 19G:
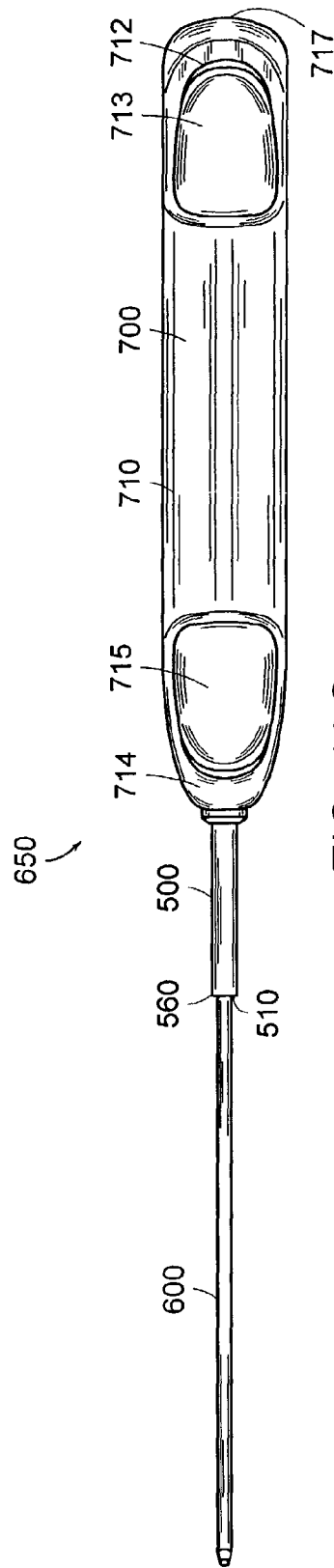
FIG. 19G illustrates a top plan view of the embodiment of FIG. 19B.
Figure 19H:
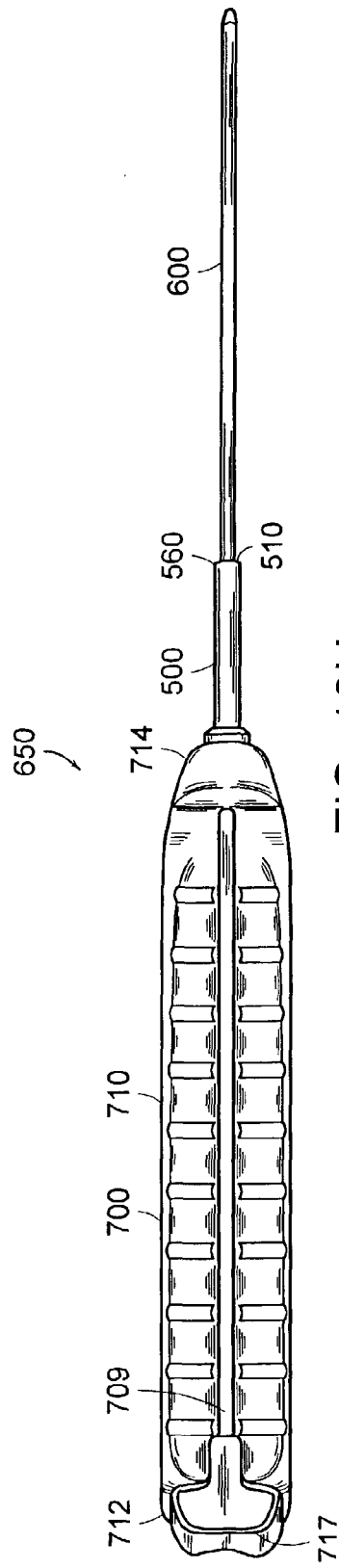
FIG. 19H illustrates a bottom plan view of the embodiment of FIG. 19B.

In another embodiment of the invention, the delivery system 2 of the invention includes a delivery assembly 650. Referring now to FIG. 19A, in one embodiment, the delivery assembly 650 includes the dilator tube 500, the cannula 600, a retractable point 740, and a delivery handle 700. The retractable point 740 is operatively joined through the distal end 714 of the handle 700 to button 713 and button 715, described below, on the handle 700. The dilator tube 500 is operatively joined to an extender button 717 positioned on an elongated member 710 of the handle 700.

Referring now to FIGS. 19A-19H, in one embodiment according to the invention, handle 700 includes the elongated member 710 having a proximal end 712 that is furthest from the conical tip 520 of the dilator tube 500, and a distal end 714 that is closest to the conical tip 520 of the dilator tube 500. Elongated member 710 of the handle 700 has at least one lumen 709, illustrated in FIG. 20D, which parallels the long axis of the handle 700. Elongated member 710 is about 4.0 inches to 14.0 inches, preferably 8.0 inches in length and about 0.5 inches to 5.0 inches, preferably 1.5 inches in diameter. Handle 700 has a proximal button 713, a distal button 715, and an extender button 717.

In one embodiment of the invention, the proximal button 713 is positioned on the surface of the elongated member 710 at the proximal end 712 on one side of the handle 700. In a particular embodiment according to the invention, the distal button 715 is positioned on the elongated member 710 at the distal end 714 of the elongated member 710 on the same side of the handle 700 as the proximal button 713. In one embodiment according to the invention, the extender button 717 is positioned on a side other than the side of the handle 700 on which the proximal button 713 and distal button 715 are positioned. For example, referring to FIG. 19A, the extender button 717 is positioned on the side of the elongated member 710 of the handle 700 opposite to the side of the elongated member 710 on which the proximal button 713 and the distal button 715 are positioned. In another embodiment, the extender button 717, proximal button 713, and the distal button 715 are positioned on the same side of the handle 700.

Figure 20A:
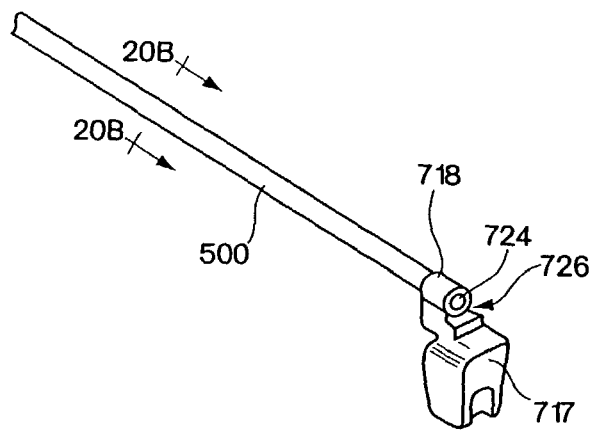
FIG. 20A illustrates an embodiment of the dilator tube and bushing according to the invention.
Figure 20B:
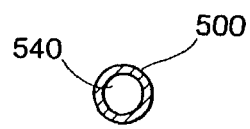
FIG. 20B illustrates a cross-section at 20B-20B of the embodiment of the dilator tube illustrated in FIG. 20A

Referring again to FIG. 19A, the dilator tube 500, described above, slides in and out of and extends outwardly from the distal end 714 of the elongated member 710 of the handle 700. The conical tip 520 of the dilator tube 500 is positioned at the distal end of the dilator tube 500. Referring now to FIGS. 20A and 20B, a bushing 724 is inserted into the proximal end 726 of the dilator tube 500. A cuff 718 is attached to the extender button 717 and rings the exterior of the proximal end 726 of dilator tube 500. In one embodiment, extender button 717 and cuff 718 are manufactured as a single unit by, for example, injection molding. In one embodiment, the bushing 724 is sized so that the dilator tube 500 fits snugly inside cuff 718. The bushing 724 maintains dilator tube 500 inside cuff 718 and retains dilator tube 500 inside the handle 700.

Figure 20C:
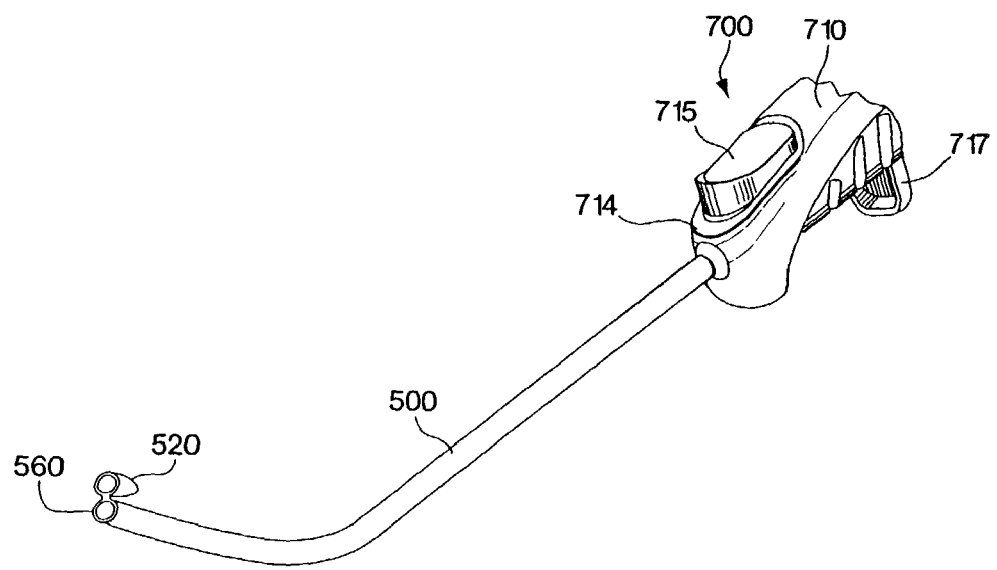
FIG. 20C illustrates an embodiment of the dilator tube illustrated in FIG. 19A in an extended position from the handle.
Figure 20D:
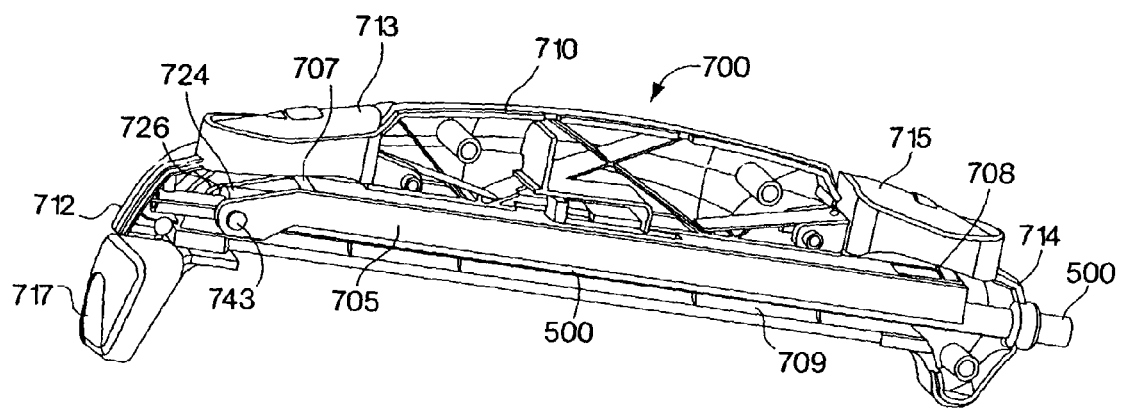
FIG. 20D illustrates an embodiment of the dilator tube illustrated in FIG. 19A with the dilator tube in a retracted position in the lumen of the handle.

Referring now to FIGS. 20C and 20D, the dilator tube 500 is manually slideably moveable by the extender button 717 from a first position, illustrated in FIG. 20C, in which the dilator tube 500 is in a first or extended position from the distal end 714 of the elongated member 710 of the handle 700, to a second or retracted position, illustrated in FIG. 20D, in which the proximal end 726 of the dilator 500 is withdrawn into the lumen 709 of the elongated member 710 of the handle 700 to a position substantially adjacent the proximal end 712 of the elongated member 710 of the handle 700.

Figure 20E:
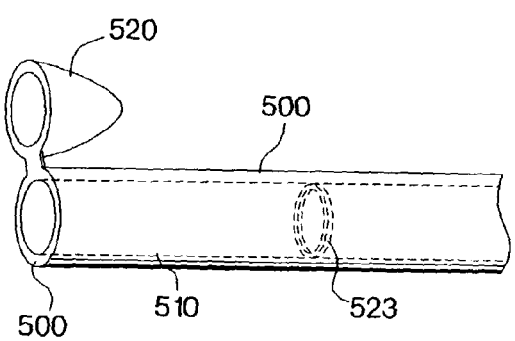
FIG. 20E illustrates an embodiment of the dilator tube illustrated in FIG. 13.
Figure 21A:
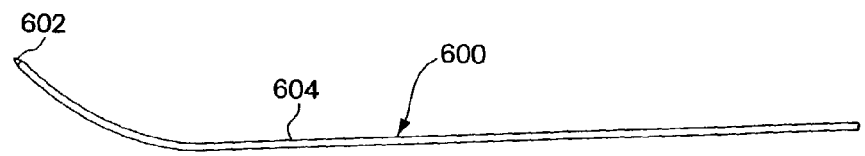
FIG. 21A illustrates an embodiment of the cannula according to the invention.
Figure 21B:
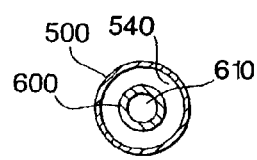
FIG. 21B illustrates a cross-section at 21B-21B of the embodiment of the cannula illustrated in FIG. 21C.
Figure 21C:
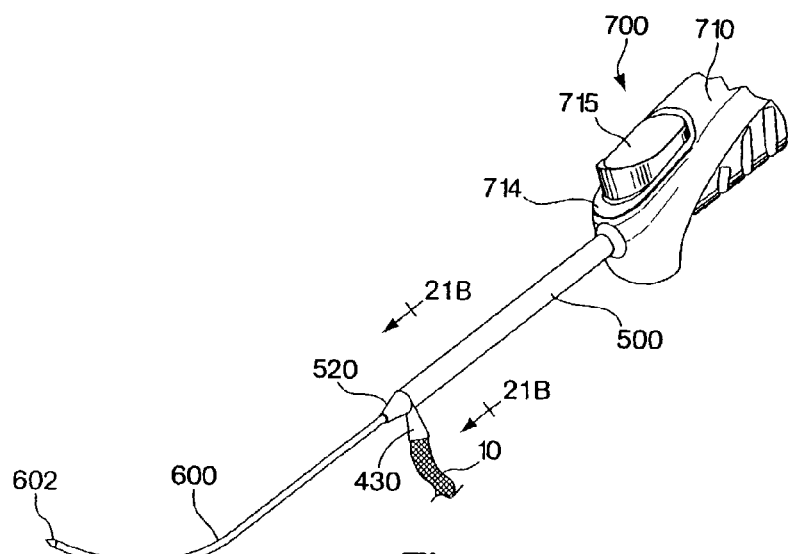
FIG. 21C illustrates an embodiment of the cannula with the dilator tube retracted.

In another embodiment of the dilator tube 500, illustrated in FIG. 20E, a rigid ring 523 is attached to the inside wall in the lumen 540 of the dilator tube 500 approximately 0.5 to 3.0 inches, preferably 1.3 inches from the end 542 of the elongated hollow member 510. The rigid ring 523 serves as a guide for passage of the cannula 600 in the lumen 540 of the dilator tube 500. In another embodiment, more than one rigid ring 523 is present in the elongated member 510 of dilator tube 500 and/or within conical tip 520 of dilator tube 500. The rigid rings 523 guide and stabilize cannula 600 placement within the lumen of dilator tube 500 and the rigid ring 523 may be placed to direct cannula 600 into the center of dilator tube 500. In one embodiment, the rigid rings 523 are tapered to an angle and become gradually flush with the inner diameter of the dilator tube 500 lumen, to assist in positioning cannula 600 within dilator tube 500. In yet another embodiment, the rigid ring 523 is an insert such as a tubular insert that may be inserted into, for example, the elongated member 510 and/or the conical tip 520 of dilator tube 500. The outer diameter of such an insert may closely correspond to the inner diameter of the elongated member 510 in one embodiment, the outer diameter of the insert is about 0.2 inches and the inner diameter is about 0.14 inches. In one embodiment, the insert is joined to the elongated member 510 by, for example, heat bonding. Referring now to FIGS. 21A, 21B, and 21C, the cannula 600 is a second hollow elongated tube 604. The cannula 600 is inserted within the lumen 540 of the dilator tube 500, illustrated in FIG. 21B. In a particular embodiment, according to the invention, the tube 604 of cannula 600 forms an arc from the cannula tip 602 at the distal end of the cannula 600, to about 10-75% of the length of tube 604. For example, referring to FIG. 19A, cannula 600 forms an arc with the concave surface of the arc on the same side of the cannula 600 as buttons 713 and 715 of the handle 700. The arc of the cannula 600 is selected to optimize the ease of insertion of the delivery system through the patient's tissues to position the implant 10 at the appropriate anatomical site. Cannula 600 is about 4.0 inches to about 14.0 inches, preferably 8.0 inches in length, and about 0.05 inches to about 0.3 inches, preferably 0.13 inches in diameter. Cannula 600 is approximately the same length as the dilator tube 500. In the most extended first position of dilator tube 500, substantially the entire length of the cannula 600 is surrounded by the dilator tube 500 as illustrated in FIG. 20C. When the dilator tube 500 is in its most retracted second position, approximately 20-50% of the cannula 600 is surrounded by the dilator tube 500 as illustrated in FIG. 21C. Cannula 600 is rigid and is manufactured from materials, such as stainless steel, plated carbon steel, or coated carbon steel.

Figure 22A:
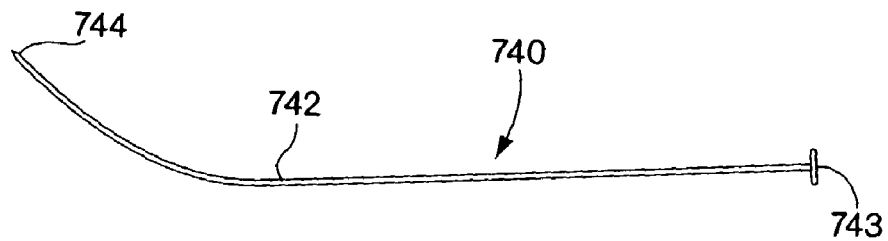
FIG. 22A illustrates an embodiment of the retractable point according to the invention.
Figure 22B:
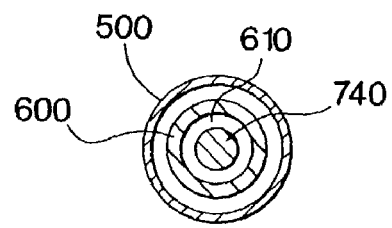
FIG. 22B illustrates a cross-section of the retractable point according to the invention.
Figure 22C:
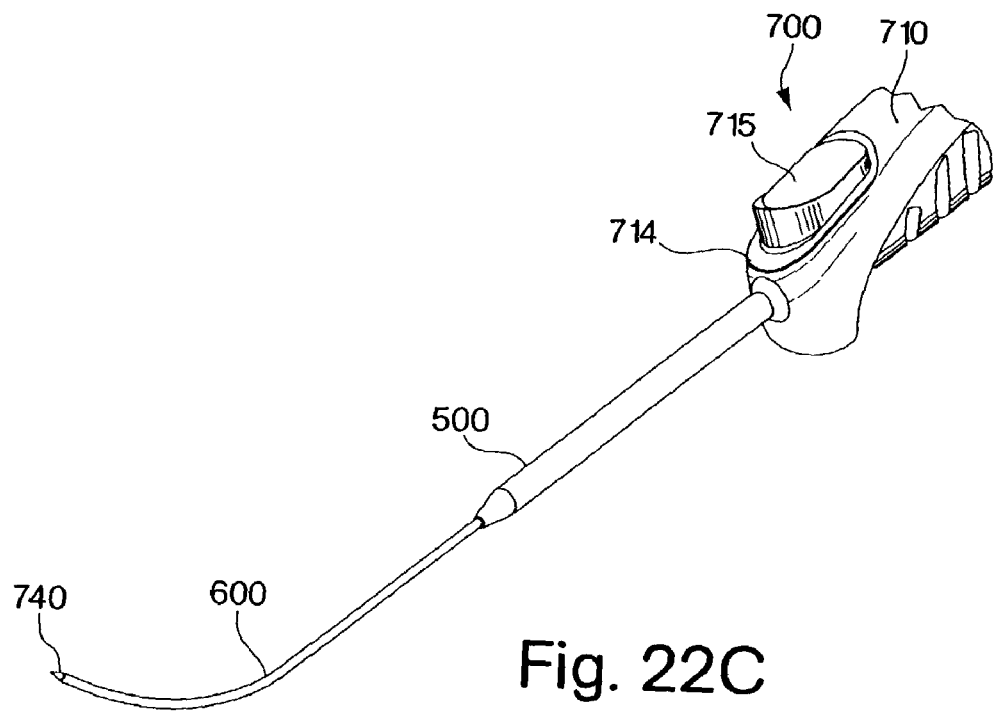
FIG. 22C illustrates the retractable point, illustrated in FIG. 22A, extended from the cannula.

Referring now to FIGS. 22A, 22B and 22C, the retractable point 740 according to the invention includes an elongated member 742 with a tapered end 744 at the distal end 741 of the elongated member 742. The elongated member 742 of the retractable point 740 is about 4.0 inches to about 14.0 inches, preferably 8.0 inches in length and 0.03 inches to about 0.1 inches, preferably 0.06 inches in diameter. The elongated member 742 of the retractable point 740 traces an arc corresponding to the arc of the cannula 600. The retractable point 740 is positioned in the lumen 610 of the cannula 600 as illustrated in FIG. 22B. The retractable point 740 is moveable from an extended first position illustrated in FIG. 22C to a retracted second position illustrated in FIG. 20C.

Figure 23A:
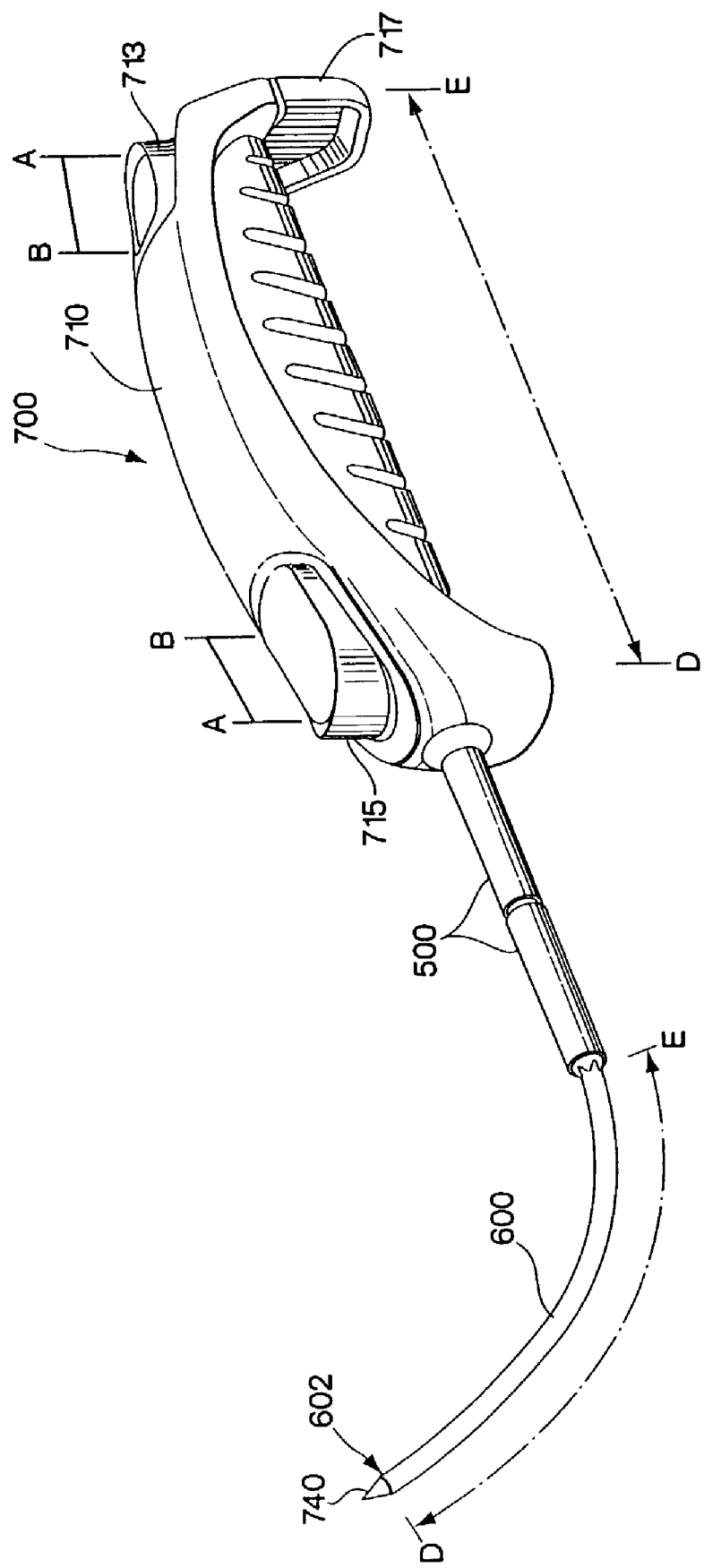
FIG. 23A illustrates two positions of an embodiment of the proximal and distal buttons and two positions of the cannula retractor button on the handle according to the invention.

Referring now to FIG. 23A, the proximal button 713 and the distal button 715 on the handle 700 are each operatively joined to the retractable point 740 and are moveable through two positions, a first position A and second position B. Referring now to FIGS. 22A and 22C, in the first position A, the tapered end 744 of the retractable point 740 is retracted into the cannula 600. In the second position B, the tapered end 744 of the retractable point 740 is extended from the distal end 602 of the cannula 600, for example, as illustrated in FIG. 22C. The buttons 713 and 715 are spring biased to the first position from the second position requiring the operator to manually hold the button 713 or 715 to maintain the button in the second position to extend the tapered end 744 from the distal end 602 of the cannula 600. Referring again to FIGS. 20D, 22A and 22C, when the proximal button 713 is held down a projection 707, located under button 713, is pushed toward the distal end 714 of delivery handle 700, which moves bar 705 forward toward distal end 714. Retractable point 740 is housed inside bar 705 and is secured inside bar 705 by bolt 743. When proximal button 713 is held down pushing projection 707 toward the distal end 714 of handle 700, the bar moves toward the distal end 714 of handle 700. Accordingly, point 744 extends in the distal direction and outside cannula 600. Similarly, because projection 708, seated under distal button 715, is inclined in the same direction as projection 707, when button 715 is held down, point 744 extends in the distal direction and outside cannula 600.

Figure 23B:
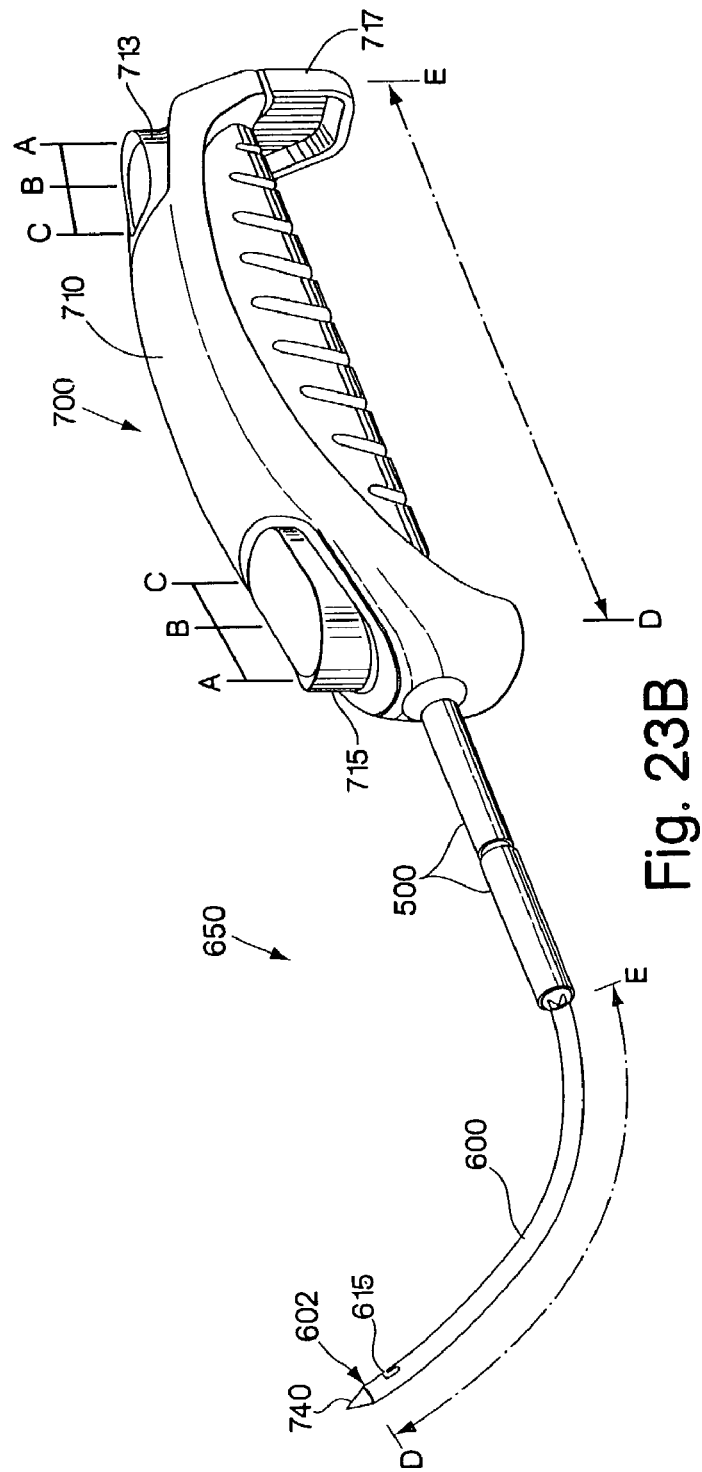
FIG. 23B illustrates three positions of an embodiment of the proximal and distal buttons and two positions of the cannula notch and two positions of the cannula retractor button on the handle according to the invention.
Figure 23C:
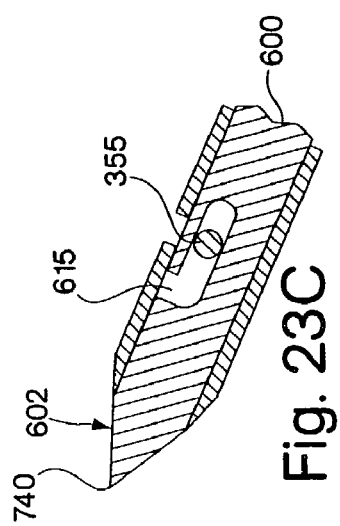
FIG. 23C illustrates another embodiment of the cannula notch illustrated in FIG. 23B.
Figure 23D:
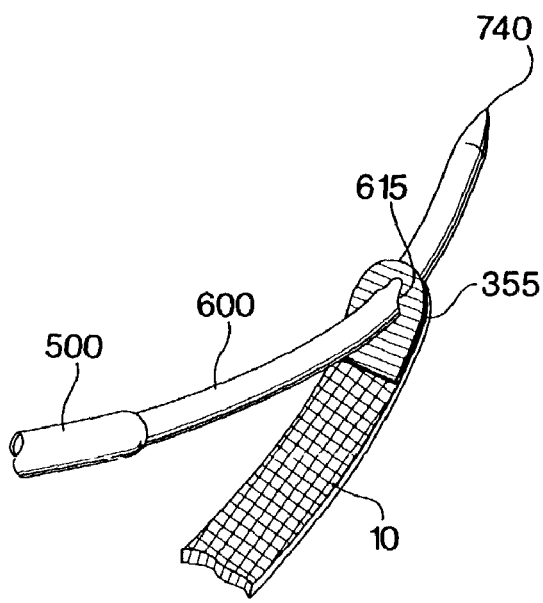
FIG. 23D illustrates an embodiment of an implant with a coupling ring.
Figure 23E:
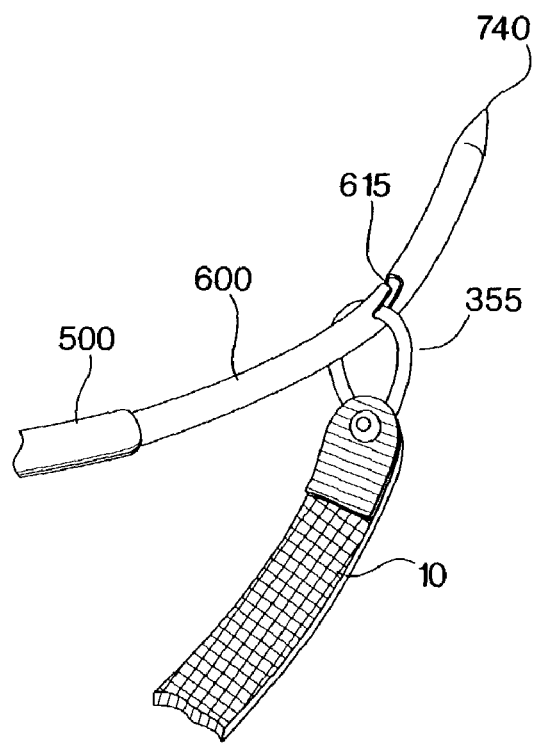
FIG. 23E illustrates another embodiment of an implant with a coupling ring.

In another embodiment of the delivery assembly 650, the cannula 600, illustrated in FIG. 23B, the portion of the cannula 600 near the distal end 602 of the cannula 600 includes a locking notch 615 to permit attachment of a coupling ring 355 to the cannula 600. The coupling ring, illustrated in FIGS. 23D and 23F, is a loop attached to an end of the implant 10, or a hole or an eyelet positioned in the end of the implant 10, for coupling to the cannula notch 615. The loop may be formed by, for example, a suture or a wire, and a loop may be anchored to the end of the implant 10 by, for example, adhesive, heat sealing, being bolted to the end of the implant 10, being threaded through the implant 10, or by other available attachment means. In another embodiment (not shown), a coupling ring 355 is positioned through one or more ends of an envelope 20 to permit joining the envelope 20 to the locking notch 615 of cannula 600.

As illustrated in FIG. 23B, in this embodiment of the invention, button 713 and button 715 have three position buttons, position A, position B and position C. In position A of button 713 and button 715, the notch 615 is in the open, unlocked position ready to receive a coupling ring 355. In position B of button 713 and button 715, the notch 615 is in the closed, locked position, as illustrated in FIG. 23C. In position B, the coupling ring 355 is locked in the notch. In position C of button 713 and button 715, the retractable point 740 is extended from the distal end 602 of the cannula 600. Position C of the button 713 and button 715 is spring-biased to position B such that the operator must hold the button in position C to extend the retractable point 740.

In another embodiment, the cannula 600 or the distal end portion of the cannula 600 is detachable from the delivery assembly 650.

Another aspect of the invention includes a method for delivering an implantable device 10 to an anatomical site in the body using the delivery assembly 650 according to the invention. An anatomical site includes, for example, the mid-urethra, prostate or neck of the urinary bladder. According to one embodiment of the method, a transvaginal approach is used with the envelope 20 enclosing implant 10, such as, for example, a PINNACLE Sling manufactured by Boston Scientific Corporation, Natick, Mass. The sling 10 is secured to the delivery assembly 650 by first bonding the sling 10 to the cylinder member 400 by heat bonding, adhesive or by other methods known to the skilled person. The dilator tube 500 is placed in the extended position illustrated in FIG. 20C by moving extender button 717 on the delivery handle 700 from position E to position D illustrated in FIG. 23A. The conical tip 520 of the dilator tube 500 is manually opened to the position illustrated in FIG. 20C (also see FIG. 11A). The second portion 420 of the cylinder member 400 is seated in the lumen 540 of the hollow elongated member 510 of the dilator tube 500, as illustrated in FIGS. 14 and 15. Conical tip 520 is manually rotated over the first portion 410 of the cylinder member 400, as shown in FIG. 16. Thus, the sling 10 is attached by attachment piece 350 to the delivery assembly 650 as shown in FIG. 17. After the sling 10 is secured to the dilator tube 500, the dilator tube 500 is moved from the extended position illustrated in FIG. 20C to the retracted position illustrated in FIG. 21C, by moving button 717 from position D to position E illustrated in FIG. 23A. The operator grasps the handle 700 and, in the transvaginal approach, advances the distal end 602 of the cannula 600 transvaginally to emerge through the rectus fascia, abdominal fasica and the abdominal wall in the region of the pubic tubercle of the patient. After confirming the correct position for placement of the sling 10 in the area of the mid-urethra, the dilator tube 500 is advanced over the cannula 600 by moving extender button 717 from the first position E to the second position D thereby advancing the dilator tube 500 distally over the cannula 600. The cannula 600 and dilator tube 500 are further advanced in the patient's tissues until the sling 10 extends through the rectus fascia. The sling 10 is disconnected from the attachment piece 350 by, for example, cutting, and the cannula 600 and dilator tube 500 are withdrawn from the patient. The procedure is repeated on the opposite side of the patient.

In another embodiment, the lumen 709 of delivery handle 700 has one or more locking regions in which dilator tube 500 may be locked in place as the operator moves dilator tube 500 from the first position E to the second position D. According to this embodiment, the operator may use both cannula 600 and dilator tube 500 to push through the rectus fascia, abdominal fascia and the abdominal wall when traversing from the vagina to the region to the pubic tubercle of the patient during the procedure. According to this embodiment, the sling 10 may be attached to the delivery assembly 650 prior to moving the dilator 500 and cannula 600 through the patient's tissue. Alternatively, the sling 10 may be attached to the delivery assembly 650 only after the tissue has been initially penetrated.

In an alternative approach to this method, the mid-urethra is approached percutaneously through the abdominal wall, abdominal fascia, and the rectus fascia rather than transvaginally as described above. In this method according to the invention, the dilator tube 500 is advanced over the cannula 600 by moving extender button 717 on the handle 700 from first position E to the second position D. In one embodiment, the extender button 717 is reversibly moveable through a plurality of positions from the first position E to the second position D. As shown in FIG. 23A, the proximal button 713 is moved from position A to position B to extend the tapered end 744 of the retractable point 740 beyond the distal end 602 of the cannula 600. By firmly grasping the handle 700, the cannula 600, with retractable point 740 extended and dilator tube 500 extended, is advanced through the rectus fascia in the region of the pubic tubercle. The cannula 600 and dilator tube 500 are advanced until they emerge from an incision in the vaginal wall. The sling 10, attached to the attachment piece 350, is secured to the delivery assembly 650 as described above. The cannula 600 and dilator tube 500 with the attached sling 10 are pulled back into the incision until the sling 10 is placed in the correct position in the region of the mid-urethra. Once positioning of the sling 10 is confirmed, the sling 10 is disconnected from the attachment piece 350 and stabilized with forceps. The cannula 600 and the dilator tube 500 are withdrawn from the body. The same steps are repeated on the opposite side of the vagina.

Another embodiment of the method for implanting an implant 10 at an anatomical site in the body of a patient includes the steps of providing an implant 10 enclosed in an envelope 20. The method further includes coating the envelope 20 with at least one drug, such as an antibiotic, on the inner surface, the outer surface, or both the inner and outer surface of the envelope. The method according to the invention may further include the step of providing a therapeutic drug dispersed on the envelope to the patients tissues.

In another embodiment, the method of the invention may further include the steps of positioning the implant 10 enclosed within the envelope 20 at the anatomical site in the body, and removing the envelope 20 while the implant 10 remains positioned at the anatomical site in the body of the patient. In yet another embodiment, the method of the invention may further include tearing the envelope 20 at the tearable region 50 of the envelope 20, and removing the envelope 20 from the body.

In another embodiment, the method of the invention includes the step of providing a spacer 100 to position the implant 10 at the target anatomical site in the patient's body. The method may further include the step of measuring the tension applied to the sling 10 by a pressure sensor 101.

Variations, modifications, and other implementations of what is described herein will occur to those of ordinary skill in the art without departing from the spirit and the scope of the invention as claimed. Accordingly, the invention is to be defined not by the preceding illustrative description but instead by the spirit and scope of the following claims.

What is claimed is:

1. A system comprising:
   an implantable sling:
   a substantially flexible envelope; said envelope comprising at least two sleeves, said sleeves enclosing at least partially said sling; and
   a clamp located near a mid portion of the envelope, wherein at least a portion of said clamp is sized to encircle the envelope and comprises two or more flat surfaces that are positionally adjustable to move toward one another such that the flat surfaces compress and couple said sleeves together between said flat surfaces;
   wherein said clamp releasably couples said sleeves, and wherein said clamp further comprises a spacer,
   wherein said spacer comprises a balloon.

2. The system of claim 1, wherein said system further comprises at least one tab.

3. The system of claim 1, wherein said system further comprises at least one attachment piece.

4. The system of claim 1, wherein at least one of said sleeves comprises a composite of two or more materials.

5. The system of claim 1, wherein a portion of said sleeves overlap.

6. The system of claim 1, wherein each sleeve is substantially the same length.

7. The system of claim 1, wherein said clamp further comprises a pressure sensor.

8. The system of claim 1, wherein said spacer further comprises a bulk material.

9. The system of claim 1, wherein said envelope comprises at least one attachment piece.

10. The system of claim 1, wherein said envelope is greater in length than the sling.

11. The system of claim 1, wherein said envelope includes first and second ends and a lumen that is closed at both of said first and second ends of the envelope.

12. The system of claim 1, wherein said sling includes first and second ends and said envelope encloses both the first and second ends of the sling.

13. The system of claim 12, wherein each sleeve encloses an end of the sling.

14. The method of implanting a sling at an anatomical site in the body of a patient, comprising:
   providing a system comprising:
      an implant sling,
      a substantially flexible envelope, said envelope comprising at least two sleeves, said sleeves enclosing at least partially said sling, and
      a clamp, said clamp is sized to encircle the envelope and comprises two or more flat surfaces that are positionally adjustable to move toward one another such that the flat surfaces compress and couple said sleeves together between said flat surfaces, wherein said clamp releasably couples said sleeves, and wherein said clamp further comprises a spacer, wherein said spacer comprises a balloon;
   coupling said sleeves between said rigid flat surfaces with said clamp; and
   implanting said sling at said anatomical site in the patient's body.

15. The method of claim 14 further comprising the steps of:
   unfastening said clamp and uncoupling said sleeves; and
   removing said clamp and said sleeves from the patient's body, said sling positioned at said anatomical site in the patient's body.

16. The method of claim 14, wherein said envelope is greater in length that the sling.

* * * * *